(12) United States Patent
Taylor et al.

(10) Patent No.: US 10,363,298 B2
(45) Date of Patent: Jul. 30, 2019

(54) IMMUNOMODULATORY COMPOUNDS

(71) Applicant: University Court of the University of St Andrews, St. Andrews (GB)

(72) Inventors: Garry Taylor, St. Andrews (GB); Helen Connaris, St. Andrews (GB)

(73) Assignee: University Court of the University of St. Andrews (GB)

( * ) Notice: Subject to any disclaimer, the term of this patent is extended or adjusted under 35 U.S.C. 154(b) by 0 days.

(21) Appl. No.: 15/113,672

(22) PCT Filed: Jan. 23, 2015

(86) PCT No.: PCT/GB2015/050161
§ 371 (c)(1),
(2) Date: Jul. 22, 2016

(87) PCT Pub. No.: WO2015/110831
PCT Pub. Date: Jul. 30, 2015

(65) Prior Publication Data
US 2017/0007692 A1 Jan. 12, 2017

(30) Foreign Application Priority Data

Jan. 24, 2014 (GB) .................................. 1401228.0
Mar. 25, 2014 (GB) .................................. 1405306.0

(51) Int. Cl.
| | | |
|---|---|---|
| *A61K 39/07* | (2006.01) | |
| *A61K 39/09* | (2006.01) | |
| *A61K 39/104* | (2006.01) | |
| *A61K 39/39* | (2006.01) | |
| *A61K 38/16* | (2006.01) | |
| *A61K 39/02* | (2006.01) | |
| *G01N 33/68* | (2006.01) | |
| *A61K 39/00* | (2006.01) | |

(52) U.S. Cl.
CPC ............ *A61K 39/107* (2013.01); *A61K 38/16* (2013.01); *A61K 39/092* (2013.01); *A61K 39/104* (2013.01); *A61K 39/39* (2013.01); *G01N 33/6854* (2013.01); *A61K 2039/543* (2013.01); *A61K 2039/572* (2013.01); *A61K 2039/575* (2013.01); *A61K 2039/58* (2013.01); *C12N 2760/16171* (2013.01); *G01N 2333/11* (2013.01); *G01N 2333/115* (2013.01); *G01N 2333/21* (2013.01); *G01N 2400/00* (2013.01); *G01N 2500/04* (2013.01)

(58) Field of Classification Search
None
See application file for complete search history.

(56) References Cited

U.S. PATENT DOCUMENTS

| | | | | |
|---|---|---|---|---|
| 6,551,795 | B1 * | 4/2003 | Rubenfield | ............ C07K 14/21 435/253.3 |
| 2002/0025320 | A1 | 2/2002 | Boyaka et al. | |
| 2002/0054880 | A1 | 5/2002 | Heerze et al. | |
| 2004/0072256 | A1 | 4/2004 | Mandelboim et al. | |
| 2005/0084903 | A1 | 4/2005 | Kim et al. | |

FOREIGN PATENT DOCUMENTS

| | | |
|---|---|---|
| EP | 2799086 | 11/2014 |
| WO | 1994/07517 | 4/1994 |
| WO | 00/10388 | 3/2000 |
| WO | 02/094869 | 11/2002 |
| WO | 2007075921 | 7/2007 |
| WO | 2008053486 | 5/2008 |
| WO | WO 2008/143676 | * 11/2008 |
| WO | WO 2009/049234 | * 4/2009 |
| WO | 2010005737 | 1/2010 |
| WO | WO 2010/029312 A1 | 3/2010 |
| WO | 2010052492 | 5/2010 |
| WO | 2010102112 | 9/2010 |
| WO | 2014052621 | 4/2014 |
| WO | 2015110831 | 7/2015 |

OTHER PUBLICATIONS

Belser et al. "DAS181, A Novel Sialidase Fusion Protein, Protects Mice from Lethal Avian Influenza H5N1 Virus Infection", *The Journal of Infectious Diseases*, 196:1493-1499, 2007.
Connaris et al. "Enhancing the Receptor Affinity of the Sialic Acid-Binding Domain of *Vibrio cholerae* Sialidase through Multivalency", *The Journal of Biological Chemistry*, vol. 284, No. 11, pp. 7339-7351, Mar. 13, 2009.
Connaris et al. "Prevention of Influenza by Targeting Host Receptors Using Engineered Proteins", *PNAS*, vol. 111, No. 17, pp. 6401-6406, Apr. 29, 2014.
Govorkova et al. "Sialic Acid-Binding Protein Sp2CBMTD Protects Mice Against Lethal Challenge with Emerging Influenza A (H7N9) Virus" *Antimicrobial Agents and Chemotherapy*, vol. 59, No. 3, pp. 1495-1504, Mar. 2015.
Xu et al. "Structural Studies on the *Pseudomonas aeruginosa* Sialidase-Like Enzyme PA2794 Suggest Substrate and Mechanistic Variations", *J. Mol. Biol.* 386, pp. 828-840, 2009).
Xu et al. "Structure of the Catalytic Domain of *Streptococcus pneumoniae* Sialidase NanA", *Acta Cryst*, F64, pp. 772-775 (2008).
PCT International Search Report and Written Opinion dated Apr. 10, 2015, PCT International Application No. PCT/GB2015/050161 (14 pages).

(Continued)

*Primary Examiner* — Oluwatosin A Ogunbiyi
(74) *Attorney, Agent, or Firm* — Myers Bigel, P.A.

(57) ABSTRACT

The present invention is based on the finding that in addition to interfering with or blocking, preventing and/or inhibiting the interaction between a pathogen and, for example, a sialic acid containing cell surface receptor, certain sialic acid binding molecules have immunomodulatory properties. The invention provides methods and uses which exploit sialic acid binding molecules in the treatment and/or prevention of disease by modulation and/or priming of the host immune response.

2 Claims, 28 Drawing Sheets

Figure 1:
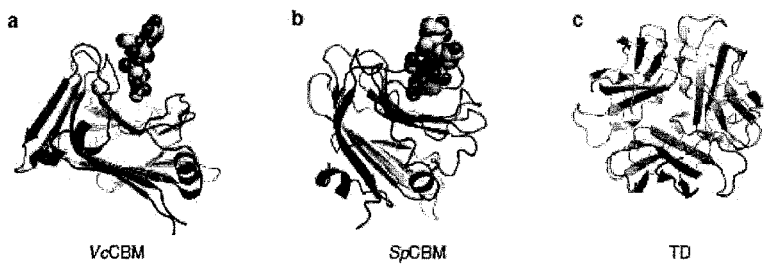

Specification includes a Sequence Listing.

(56) References Cited

OTHER PUBLICATIONS

Alias N. Multivalent sialic acid for binding proteins as novel therapeutics for influenza and parainfluenza infection. A Thesis Submitted for the Degree of PhD at the University of St Andrews. University of St Andrews, Scotland, UK. Feb. 27, 2014. 252 pages. http://hdl.handle.net/10023/4479.
Banerjee et al. "Activation of brain endothelium by Pneumococcal neuraminidase NanA promotes bacterial internalization" *Cellular Microbiology* 12(11):1576-1588 (2010).
Baranovich et al. "The Neuraminidase Inhibitor Oseltamivir Is Effective Against A/Anhui/1/2013 (H7N9) Influenza Virus in a Mouse Model of Acute Respiratory Distress Syndrome" *The Journal of Infectious Diseases* 209:1343-1353 (2014).
Baz et al. "Emergence of Oseltamivir-Resistant Pandemic H1N1 Virus during Prophylaxis" *The New England Journal of Medicine* 361(23):2296-2297 (2009).
Belser et al. "Pathogenesis and transmission of avian influenza A (H7N9) virus in ferrets and mice" *Nature* 501:556-559 (2013).
Boltz et al. "Drugs in Development for Influenza" *Drugs* 70(11):1349-1362 (2010).
Cantarel et al. "The Carbohydrate-Active EnZymes database (CAZy): an expert resource for Glycogenomics" *Nucleic Acids Research* 37:D233-D238 (2009).
Cantor et al. "Therapeutic enzyme deimmunization by combinatorial T-cell epitope removal using neutral drift" *Proceedings of the National Academy of Sciences* 108(4):1272-1277 (2011).
Chan et al. "Tropism and innate host responses of a novel avian influenza A H7N9 virus: an analysis of ex-vivo and in-vitro cultures of the human respiratory tract" *The Lancet Respiratory Medicine* 1(7):534-542 (2013) (Abstract Only).
ClinicalTrials.gov "Single Dose Escalating Study of DAS181 in Adults" http://www.clinicaltrials.gov/ct2/show/NCT00527865?term=Fludase&rank=2 (5 pages) (last updated: Jan. 6, 2009).
Connaris et al. "Enhancing the Receptor Affinity of the Sialic Acid-binding Domain of *Vibrio cholerae* Sialidase through Multivalency" *The Journal of Biological Chemistry* 284(11):7339-7351 (2009).
Connaris et al. "Prevention of influenza by targeting host receptors using engineered proteins" *Proceedings of the National Academy of Sciences* 111(17):6401-6406 (2014).
De Groot et al. "Low immunogenicity predicted for emerging avian-origin H7N9: Implication for influenza vaccine design" *Human Vaccines & Immunotherapeutics* 9(5):950-956 (2013).
Efstathiou et al. "Murine herpesvirus 68 is genetically related to the gammaherpesviruses Epstein-Barr virus and herpesvirus saimiri" *Journal of General Virology* 71:1365-1372 (1990).
Ekiert et al. "Broadly neutralizing antibodies against influenza virus and prospects for universal therapies" *Current Opinion in Virology* 2(2):134-141 (2012).
Gao et al. "Human Infection with a Novel Avian-Origin Influenza A (H7N9) Virus" *The New England Journal of Medicine* 368:1888-1897 (2013).
Guan et al. "Molecular characterization of H9N2 influenza viruses: Were they the donors of the "internal" genes of H5N1 viruses in Hong Kong?" *Proceedings of the National Academy of Sciences USA* 96:9363-9367 (1999).
Herfst et al. "Airborne Transmission of Influenza A/H5N1 Virus Between Ferrets" *Science* 336(6088):1534-1541 (2012).
Hu et al. "Association between adverse clinical outcome in human disease caused by novel influenza A H7N9 virus and sustained viral shedding and emergence of antiviral resistance" *Lancet* 381:2273-2279 (2013).
Hu et al. "Limited human-to-human transmission of avian influenza A(H7N9) virus, Shanghai, China, Mar. to Apr. 2013" *Eurosurveillance* 19(25):1-10 (2013).
Ilyushina et al. "Combination chemotherapy, a potential strategy for reducing the emergence of drug-resistant influenza A variants" *Antiviral Research* 70:121-131 (2006) (Abstract Only).

Ilyushina et al. "Adaptation of Pandemic H1N1 Influenza Viruses in Mice" *Journal of Virology* 84(17):8607-8616 (2010).
IMAI et al. "Experimental adaptation of an influenza H5 HA confers respiratory droplet transmission to a reassortant H5 HA/H1N1 virus in ferrets" *Nature* 486:420-428 (2012).
Li et al. "Epidemiology of Human Infections with Avian Influenza A(H7N9) Virus in China" *The New England Journal of Medicine* 370:520-532 (2014).
Liu et al. "One family cluster of avian influenza A(H7N9) virus infection in Shandong, China" *BMC Infectious Diseases* 14(98):1-6 (2014).
Ludwig, Stephan "Disruption of virus-host cell interactions and cell signaling pathways as an anti-viral approach against influenza virus infections" *Biological Chemistry* 392:837-847 (2011).
Malakhov et al. "Sialidase Fusion Protein as a Novel Broad-Spectrum Inhibitor of Influenza Virus Infection" *Antimicrobial Agents and Chemotherapy* 50(4):1470-1479 (2006).
Mammen et al. "Polyvalent Interactions in Biological Systems: Implications for Design and Use of Multivalent Ligands and Inhibitors" *Angewandte Chemie International Edition* 37:2755-2794 (1998).
Marjuki et al. "An Investigational Antiviral Drug, DAS181, Effectively Inhibits Replication of Zoonotic Influenza A Virus Subtype H7N9 and Protects Mice From Lethality" *The Journal of Infectious Diseases* 210:435-440 (2014).
Morens et al. "Predominant Role of Bacterial Pneumonia as a Cause of Death in Pandemic Influenza: Implications for Pandemic Influenza Preparedness" *The Journal of Infectious Diseases* 198(7):962-970 (2008).
Moss et al. "A Phase II Study of DAS181, a Novel Host Directed Antiviral for the Treatment of Influenza Infection" 206:1844-1851 (2012).
Moustafa et al. "Sialic Acid Recognition by *Vibrio cholerae* Neuraminidase" *The Journal of Biological Chemistry* 279(39):40819-40826 (2004).
Osterhaus et al. "Towards universal influenza vaccines?" *Philosophical Transactions of the Royal Society B* 366:2766-2773 (2011).
Osterholm et al. "Major challenges in providing an effective and timely pandemic vaccine for influenza A(H7N9)" *JAMA* 309:2557-2558 (2013) (Abstract Only).
Qi et al. "Probable person to person transmission of novel avian influenza A (H7N9) virus in Eastern China, 2013: epidemiological investigation" *BMJ* 347(14752):1-8 (2013).
Russell et al. "The potential for respiratory droplet-transmissible A/H5N1 influenza virus to evolve in a mammalian host" *Science* 336(6088):1541-1547 (2012).
Salomon et al. "The influenza virus enigma" *Cell* 136:402-410 (2009).
Sarawar et al. "Cytokine production in the immune response to murine gammaherpesvirus" *Journal of Virology* 70(5):3264-3268 (1996).
Schwegmann-Weßels et al. "Sialic acids as receptor determinants for coronaviruses" *Glycoconjugate Journal* 23:51-58 (2006).
Shinya et al. "Avian flu: influenza virus receptors in the human airway" *Nature* 440:435-436 (2006).
Skehel et al. "Receptor Binding and Membrane Fusion in Virus Entry: The Influenza Hemagglutinin" *Annual Review of Biochemistry* 69:531-569 (2000).
Stewart et al. "Identification and Characterization of Murine Gammaherpesvirus 68 gp150: a Virion Membrane Glycoprotein" *Journal of Virology* 70(6):3528-3535 (1996).
Sunil-Chandra et al. "Murine gammaherpesvirus 68 establishes a latent infection in mouse B lymphocytes in vivo" *Journal of General Virology* 73:3275-3279 (1992).
Sunil-Chandra et al. "Virological and pathological features of mice infected with murine gamma-herpesvirus 68" *Journal of General Virology* 73:2347-2356 (1992).
Sunil-Chandra et al. "Lymphoproliferative Disease in Mice Infected with Murine Gammaherpesvirus 68" *American Journal of Pathology* 145(4):818-826 (1994).
Suzuki et al. "Receptor Specificities of Human Respiroviruses" *Journal of Virology* 75(10):4604-4613 (2001).

(56) References Cited

OTHER PUBLICATIONS

Trappetti et al. "Sialic Acid: A Preventable Signal for Pneumococcal Biofilm Formation, Colonization, and Invasion of the host" *The Journal of Infectious Diseases* 199:1497-1505 (2009).
Van Riel et al. "Novel Avian-Origin Influenza A (H7N9) Virus Attaches to Epithelium in Both Upper and Lower Respiratory Tract of Humans" *The American Journal of Pathology* 183(4):1137-1143 (2013).
Varki, Ajit "Glycan-based interactions involving vertebrate sialic-acid-recognizing proteins" *Nature* 446:1023-1029 (2007).
Varki et al. "Multifarious roles of sialic acids in immunity" *Annals of the New York Academy of Sciences* 1253(1):16-36 (2012).
Walther et al. "Glycomic Analysis of Human Respiratory Tract Tissues and Correlation with Influenza Virus Infection" *PLoS Pathogens* 9(3):e1003223 (2013).
Watanabe et al. "Characterization of H7N9 influenza A viruses isolated from humans" *Nature* 501(7468):551-555 (2013).
Webster et al. "Continuing challenges in influenza" *Annals of the New York Academy of Sciences* 1323(1):115-139 (2014).
World Health Organization "Confirmed human cases of avian influenza A(H7N9) reported to WHO: Report 18—data in WHO/HQ as of Jul. 14, 2014" http://www.who.int/influenza/human_animal_interface/influenza_h7n9/18_reportwebh7n9number_20140714.pdf?ua=1 (4 pages) (2014).
Xiao et al. "Transmission of avian influenza A(H7N9) virus from father to child: a report of limited person-to-person transmission, Guangzhou, China, Jan. 2014" *Eurosurveillance* 19(25):1-9 (2014).
Xiong et al. "Receptor binding by an H7N9 influenza virus from humans" *Nature* 499:496-499 (2013).
Xu et al. "Structure of the catalytic domain of *Streptococcus pneumoniae* sialidase NanA" *Acta Crystallographica Section F* 64:772-775 (2008).
Xu et al. "Structural studies on the *Pseudomonas aeruginosa* sialidase-like enzyme PA2794 suggest substrate and mechanistic variations" *Journal of Molecular Biology* 386:828-840 (2009) (Abstract Only).
Xu et al. "Novel Avian-Origin Human Influenza A(H7N9) Can Be Transmitted Between Ferrets via Respiratory Droplets" *The Journal of Infectious Diseases* 209:551-556 (2014).
Zhang et al. "H7N9 Influenza Viruses Are Transmissible in Ferrets by Respiratory Droplet" *Science* 341(6144):410-414 (2013).
Zhou et al. "Biological features of novel avian influenza A (H7N9) virus" *Nature* 499:500-503 (2013).

Japanese Office Action corresponding to Japanese Patent Application No. 2016-565576, dated Jan. 11, 2019, 25 pages with English Translation.
Guillen et al. "Carbohydrate-binding domains: multiplicity of biological roles" Applied Microbiology and Biotechnology, 86(5):1241-1249 (2010).
Dagher et al. "Heterologous Expression of a Bioactive-Hexosyltransierase, an Enzyme Producer of Prebiotics, from Sporobolomyces singularis" Applied and Environmental Microbiology, 79(4):1241-1249 (2013).
Baradaran et al. "Newcastle Disease Virus Hemmagglutinin Neuraminidase as a Potential Cancer Targeting Agent" Journal of Cancer, 7(4):462-466 (2016).
Chen et al. "Amelioration of sepsis by inhibiting sialidase-mediated disruption of the CD24-SiglecG interaction" Nature Biotechnology, 29(5):428-435 (2011) (Abstract only).
Gasiorowski et al. "The impact of neuraminidase on apoptosis in cultures of blood lumphocytes isolated from rats bearing morris hepatoma" Cellular & Molecular Biology Letters, 9:389-399 (2004).
Grata-Borkowska et al. "Effects of neuraminidase on apoptosis of blood lymphocytes in rats with implanted morris tumor" Journal of Physiology and Pharmacology, 56(Suppl. 5)253-262 (2007).
Knop et al. "Stimulatory effect of Vibrio cholerae neuraminidase on the antibody reponse to verious antigen" Immunology, 34:181-187 (1978).
Manco et al. "Pneumococcal Neuraminidases A and B Both Have Essential Roles during Infection of the Respiratory Tract and Sepsis" Infection and Immunity, 74(7):4014-4020 (2006).
Research Councils UK: Gateway to Research "Exploiting a sialic acid binding domain" (4 pages) (2017).
Rios et al. "Experimental cancer immunotherapy: modification of tumour cells to increase immunogenicity" Annals of the New York Academy of Sciences, 276:45-60 (1976).
Simmons et al. "Immunospecific regression of methycholanthrene fibrosarcoma using neuraminidase" Annals of Surgery, 176(2):188-194 (1972).
Simmons et al. "Immunospecific regression of methylocholantren fibrosarcoma with the use of neuraminidase, II, Intratumor injections of neuraminidase" Surgery, 71(4):556-564 (1972).
Simmons et al. "Regression of Established Methylocholanthrene Tumors by Intratumor Injections of Vibrio Cholarae Neuraminidase" Journal of Surgical Oncology, 4(4):298-305 (1972).
Yang et al. "Structural characterization of the carbohydrate-binding module of NanA sialidase, a pneumococcal virulence factor" BMC Structural Biology, 15:1-10 (2015).

* cited by examiner

| Glycan Number | Glycan Structure |
|---|---|
| 238 | Neu5Acα2-3Galβ1-3(Neu5Acα2-3Galβ1-4)GlcNAcβ-Sp8 |
| 240 | Neu5Acα2-3Galβ1-3(Neu5Acα2-6)GalNAcα-Sp8 |
| 247 | Neu5Acα2-3Galβ1-3GlcNAcβ-Sp8 |
| 227 | Neu5Acα2-3(6-O-Su)Galβ1-4(Fucα1-3)GlcNAcβ-Sp8 |
| 248 | Neu5Acα2-3Galβ1-4[6OSO3]GlcNAcβ-Sp8 |
| 239 | Neu5Acα2-3Galβ1-3[6OSO3]GalNAcα-Sp8 |
| 269 | Neu5Acα2-6Galβ1-4Glcβ-Sp0 |
| 471 | Neu5Acα2-3Galβ1-4GlcNAcβ1-2Manα-Sp0 |
| 241 | Neu5Acα2-3Galβ1-3(Neu5Acα2-6)GalNAcα-Sp14 |
| 220 | Neu5Acα2-3Galβ1-3GalNAcα-Sp8 |
| 45 | Neu5Acα2-3[6OSO3]Galβ1-4GlcNAcβ-Sp8 |
| 54 | Neu5Acα2-6Galβ1-4GlcNAcβ1-2Manα1-3(Neu5Acα2-6Galβ1-4GlcNAcβ1-2Manα1-6)Manβ1-4GlcNAcβ1-4GlcNAcβ-N(LT)AVL |
| 439 | Neu5Acα2-3Galβ1-4GlcNAcβ1-3Galβ-Sp8 |
| 249 | Neu5Acα2-3Galβ1-4(Fucα1-3)[6OSO3]GlcNAcβ-Sp8 |
| 232 | Neu5Acα2-3(Neu5Acα2-6)GalNAcα-Sp8 |
| 246 | Neu5Acα2-3Galβ1-3GlcNAcβ-Sp0 |
| 291 | Neu5Acα2-3Galβ1-3GlcNAcβ1-3Galβ1-3GlcNAcβ-Sp0 |
| 271 | Neu5Acα2-6Galβ-Sp8 |
| 231 | Neu5Acα2-3(Neu5Acα2-3Galβ1-3GalNAcβ1-4)Galβ1-4Glcβ-Sp0 |
| 265 | Neu5Acα2-6Galβ1-4GlcNAcβ-Sp0 |
| 242 | Neu5Acα2-3Galβ1-3Galβ-Sp8 |
| 253 | Neu5Acα2-3Galβ1-4(Fucα1-3)GlcNAcβ1-3Galβ-Sp8 |
| 221 | Neu5Acα2-3Galβ1-3GalNAcα-Sp14 |
| 236 | Neu5Acα2-3Galβ1-3(Fucα1-4)GlcNAcβ-Sp8 |
| 257 | Neu5Acα2-3Galβ1-4GlcNAcβ-Sp8 |
| 476 | Neu5Acα2-3Galβ1-4GlcNAcβ1-2Manα1-6(Neu5Acα2-3Galβ1-4GlcNAcβ1-2Manα1-3)Manβ1-4GlcNAcβ1-4(Fucα1-6)GlcNAcβ-6AA |
| 484 | Neu5Acα2-3Galβ1-3GlcNAcβ1-6GalNAcα-Sp14 |
| 266 | Neu5Acα2-6Galβ1-4GlcNAcβ-Sp8 |
| 9 | Neu5Acα-Sp8 |

Figure 5 continued

Figure 14:
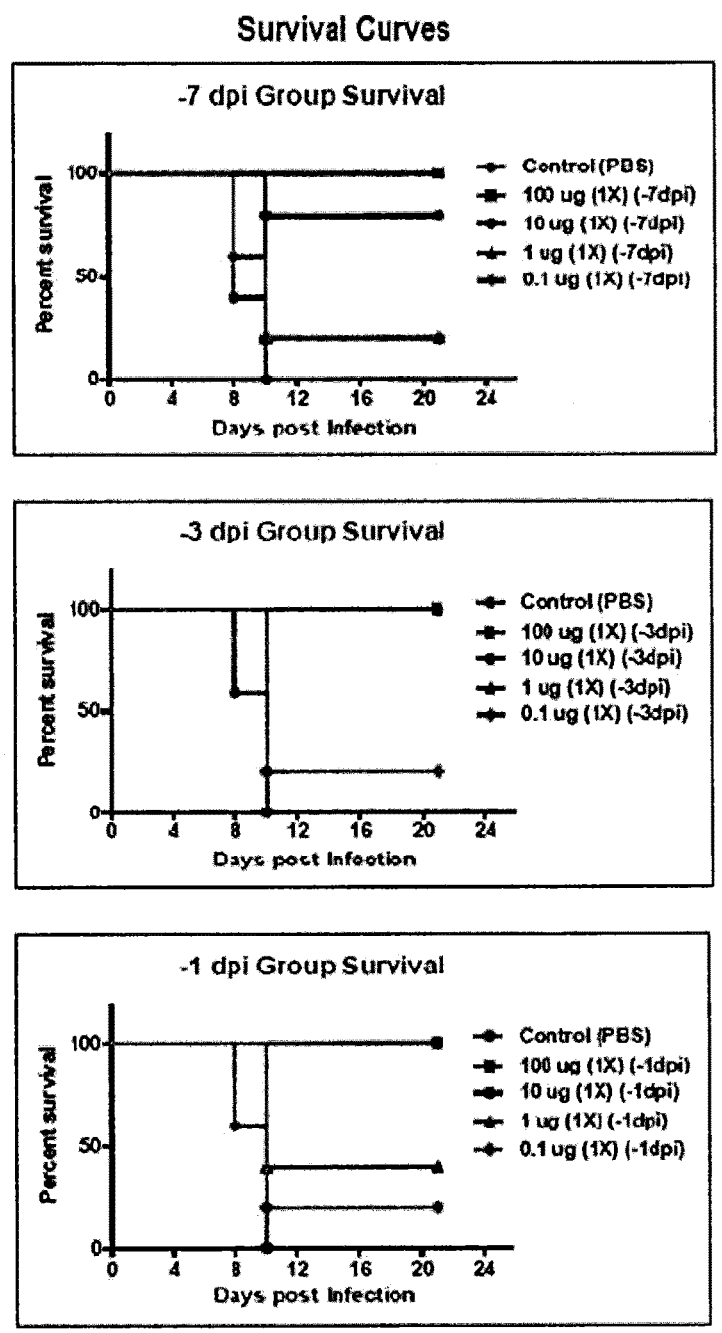

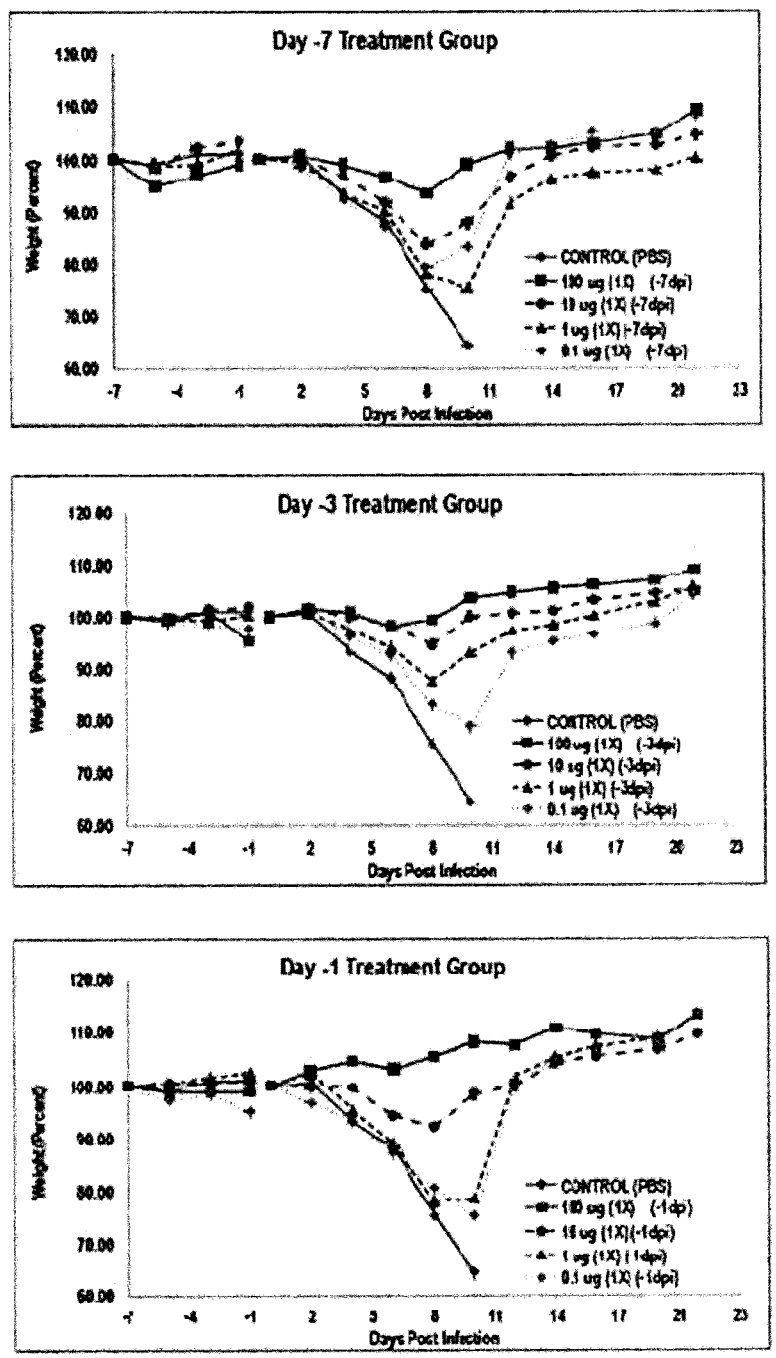
Figure 14 (ctnd)

IMMUNOMODULATORY COMPOUNDS

RELATED APPLICATIONS

This application is a 35 U.S.C. § 371 national phase entry of PCT Application PCT/GB2015/050161, filed Jan. 23, 2015, and published in English on Jul. 30, 2015, as International Publication No. WO 2015/110831 A1, which claims the priority to United Kingdom Application No. 1405306.0, filed Mar. 25, 2014, and United Kingdom Application No. 1401228.0, filed Jan. 24, 2014, the disclosure of each of which is incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 9013-149_ST25.txt, 23,370 bytes in size, generated on Jul. 21, 2016, and filed via EFS-Web, is provided in lieu of a paper copy. This Sequence Listing is hereby incorporated by reference into the specification for its disclosures.

FIELD OF THE INVENTION

The present invention provides sialic acid-binding compounds, which exhibit an immunomodulatory effect. The compounds described herein find application in the treatment and/or prevention of a range of diseases including those caused by pathogens of the upper and/or lower respiratory tract.

BACKGROUND OF THE INVENTION

A great many viral, bacterial and fungal pathogens continue to be a threat to human health and a burden on health services[1]. Of particular concern are the influenza viruses and most notably the emergence of highly pathogenic H5N1 viruses and recent introductions of H7N9 viruses from avian sources'. These viruses exhibit the potential to acquire human transmissibility and thus represent an increased health threat[3-5].

While vaccines remain a cornerstone of prevention, significant time is required to develop effective vaccines against these new pathogens. Antimicrobial drugs (including anti-virals particularly the influenza virus neuraminidase inhibitors and antibiotics), are available but their effectiveness can be compromised by the pathogen's ability to mutate and become drug resistant[6,7]. There is clearly a need for new therapeutic approaches.

A poster entitled "Engineering Multivalent Sialic Acid Recognition using the CBM40 module from *Vibrio cholerae* Sialidase" (published 17 May 2008) describes the development of reagents with increased affinity for sialic acid through multivalency. However, the poster does not disclose that such reagents have any application as immunomodulatory compounds useful in the treatment of diseases and/or conditions caused by pathogens.

US20020054880 (to Amstrong et al) describes peptides capable of binding terminally linked α-sialic acid(2→6)βGal- and/or α-sialic acid(2→3)βGal-groups and theft use in methods of inhibiting immune responses or cellular interactions in mammals. There is no disclosure of the immunostimulatory effect of sialic acid binding molecules.

SUMMARY OF THE INVENTION

The present invention is based on the finding that certain compounds capable of binding sialic acid may find application in the treatment and/or prevention of disease—in particular diseases with a microbial aetiology including, for example, respiratory diseases.

It is known that molecules, which exhibit an ability to bind sialic acid, may be used to neutralise or prevent infection by pathogens that exploit the presence of sialic acid containing receptors on the surface of host cells. For example, respiratory pathogens such as viruses belonging to the Orthomyxoviridae or Paramyxoviridae families and certain *Streptococcus* bacteria utilise cell surface sialic acid containing receptors to bind and gain entry to specific cell types in a variety of mammalian tissues. Compounds, for example proteins and peptides, which bind to sialic acid moieties and/or molecules (for example cell surface receptors) comprising the same, may be used in the treatment and/or prevention of diseases caused or contributed to by pathogens which exploit cell surface sialic acid receptors as a means to bind or adhere to cells. Without wishing to be bound by theory, a sialic acid binding molecule may interfere with and/or inhibit, prevent and/or block the interaction between the pathogen and the cell surface sialic acid receptor, so as to prevent the pathogen from binding and/or adhering.

The inventors have now discovered that in addition to (or perhaps as a consequence of or in combination with) interfering with or blocking, preventing and/or inhibiting the interaction between a pathogen and, for example, a sialic acid containing cell surface receptor, certain sialic acid binding molecules have immunomodulatory properties.

Thus, in a first aspect, the invention provides a sialic acid binding molecule for use in modulating or priming an immune response in a subject. Additionally, the invention provides a sialic acid binding molecule for use in a method of modulating or priming an immune response in a subject.

The invention provides sialic acid binding molecules for the treatment and/or prevention of disease (caused by for example bacterial, fungal and/or viral pathogens), by modulation and/or priming of the host (i.e. the subject at risk of developing a disease or infection or suffering (or suspected to be suffering) therefrom) immune response.

The invention may further provide use of a sialic acid binding protein for the manufacture of a medicament for modulating an immune response in a subject. Moreover, the invention may provide a method of modulating an immune response in a subject, the method comprising administering an immunomodulatory (or immunostimulatory) amount or quantity of a sialic acid binding protein of this invention to a subject in need thereof.

It should be noted that throughout this specification the terms "comprise" and/or "comprising" are used to denote that aspects and/or embodiments of the invention "comprise" the noted features and as such, may also include other features. However, in the context of this invention, the terms "comprise" and "comprising" encompass embodiments in which the invention "consists essentially of" the relevant features or "consists of" the relevant features.

An advantage associated with the sialic acid binding proteins of this invention—in particular the multivalent carbohydrate binding modules described herein (see below), is that they prime the host immune system such that it is better able to cope with an infection and/or a disease caused or contributed to by a pathogen of the type described herein. Without wishing to be bound by any particular theory, the inventors suggest that the sialic acids binding molecules of this invention may be used as prophylactic therapies protecting subjects against not only current infections and/or diseases but also future infections and/or diseases. Additionally or alternatively, the sialic acid binding molecules of this invention may be administered post infection—for example to subjects that have already been infected by a pathogen (such subjects may be asymptomatic or symptomatic). The inventors have shown that even when administered "post-infection", the sialic acid molecules of this invention can facilitate resolution and/or clearance of a disease, infection or pathogen.

The terms "modulation" or "immunomodulation" (or "immunostimulation") as applied to the observed effects of the various sialic acid binding molecules of this invention on host immune responses, encompass any priming of the immune system and/or (immuno)modulation (i.e. increase or decrease) in/of the expression, function and/or activity of immune system processes, pathways and/or any component(s) thereof. The term "priming" as applied to an immune response may encompass the phenomenon of increasing the readiness and/or responsiveness of an immune system to an immunogen, antigen, pathogen, disease or infection. Without wishing to be bound by theory, in addition to any immunomodulatory properties associated with the sialic acid binding molecules of this invention, subjects administered or contacted with sialic acid binding molecules may be rendered better able to cope with the onset of an infection/disease.

For example, the invention may provide sialic acid binding molecules which increase or enhance the expression, function and/or activity of one or more immunoregulatory compounds including, for example, chemokine and/or cytokine molecules and/or any genes/transcription factors encoding and/or associated with the same.

As such, the sialic acid binding molecules described herein may modulate the function, expression and/or activity of one or more cytokine and/or chemokine molecules of the immune system. Specifically, the sialic acid binding molecules may modulate the function expression and/or activity of one or more cytokine or chemokine molecules associated with an immune response to an infection by a pathogen. Such an infection may be caused or contributed to by one or more viral, bacterial and/or fungal pathogens as described in more detail below.

Cytokines and/or chemokines, the function, expression and/or activity of which are modulated by the sialic acid binding proteins described herein, may be collectively referred to as "infection associated cytokines/chemokines". The term "infection associated cytokines/chemokines" may include those cytokine/chemokine molecules, which are normally associated with an immune response, which facilitates the clearance and/or resolution of an infection. For example, the term may embrace pro-inflammatory, anti-viral and/or pro-phagocytic cytokines/chemokines. As such, the sialic acid binding molecules of this invention may be exploited as a means to modulate one or more infection associated cytokines/chemokines and/or one or more pro-inflammatory, anti-viral and/or pro-phagocytic/cytotoxic cytokines/chemokines.

The inventors have noted that the sialic acid binding molecules of this invention may induce increased expression of, for example, interleukin 1-β (IL1-β), interleukin 8 (IL-8: studies identified increases in MIP-2 expression the mouse homologue of IL-8), interferon-γ (IFN-γ) and tumour necrosis factor-α (TNF-α). One of skill will appreciate that molecules capable of modulating, for example increasing, the expression, function and/or activity of IL1-β, will have an effect on, for example, inflammatory responses, which are (at least partially) regulated by this cytokine. Similarly, given that IL-8 is involved in chemotaxis and phagocytosis, modulation of any aspect of the expression, function and/or activity of this cytokine is likely to modulate an immune response in a subject. Interferon-γ and Tumour necrosis factor-α are well known mediators of the innate and adaptive immune response and thus compounds, which modulate (for example) increase the expression, function and/or activity of these cytokines may be regarded as immunomodulatory compounds.

The sialic acid binding molecules of this invention may further modulate (for example induce or increase) the recruitment, proliferation and/or migration of immune cells to the site of an infection. For example, in subjects administered a sialic acid binding molecule of this invention, the process of immune cell recruitment, proliferation and migration may be exacerbated to some degree and/or more rapid.

In view of the above, the invention provides a sialic acid binding molecule for use in stimulating, enhancing or increasing the expression function and/or activity of one or more chemokines and/or cytokines in a subject. Additionally, the invention provides a sialic acid binding molecule for use in a method of stimulating, enhancing or increasing the expression function and/or activity of one or more chemokines and/or cytokines in a subject.

The invention may further provide use of a sialic acid binding protein for the manufacture of a medicament for stimulating, enhancing or increasing the expression function and/or activity of one or more chemokines and/or cytokines in a subject. Moreover, the invention may provide a method of stimulating, enhancing or increasing the expression function and/or activity of one or more chemokines and/or cytokines in a subject, the method comprising administering an immunomodulatory amount or quantity of a sialic acid binding protein of this invention to a subject in need thereof.

A "subject" or "a subject in need thereof" may, for example, be any human or animal (mammalian) subject. Accordingly, the sialic acid binding molecules of this invention may be applied to the modulation of immune responses in human and/or animal subjects.

The immunomodulatory compounds of this invention may find application in the treatment and/or prevention of a disease or infection—in particular, but not limited to, a disease or infection caused or contributed to by a pathogen which is able to bind and/or adhere to sialic acid containing cell surface receptors. The term "pathogens" may include, for example, viral, bacterial, protozoan and/or fungal pathogens, some of which may possess an ability to interact and/or associate with and/or bind to, a host cell sialic acid containing receptor. Thus the invention may find application in the treatment and/or prevention of respiratory diseases/infections caused or contributed to by viral, bacterial, protozoan and/or fungal pathogens, some of which may exploit the presence of sialic acid containing receptors on the surface of epithelial cells lining the surface of the upper and lower respiratory tracts.

Thus, the "subject" (whether animal or human), may be symptomatic and/or (suspected of) suffering from an infection or disease, for example a respiratory infection or disease. Alternatively, the subject may be asymptomatic and/or predisposed/susceptible to an infection or disease, for example, a respiratory infection or disease. In all cases, the infection or disease may have a microbial (for example bacterial, viral, protozoan and/or fungal aetiology.

For example, the immune response of a subject may be modulated by the immunomodulatory (sialic acid binding) compounds of the invention, so as to prime the immune system of that subject (by inducing or stimulating the expression, function and/or activity of one or more chemokines and/or cytokines) such that it is better able to cope with an infection and/or a disease caused or contributed to by a pathogen of the type described herein.

A respiratory disease and/or infection may be caused or contributed to by respiratory pathogens such as viruses belonging to the Orthomyxoviridae or Paramyxoviridae families and certain *Streptococcus* bacteria which utilise cell surface sialic acid containing receptors to bind and/or gain entry to specific cell types. For example, a respiratory disease may be caused or contributed to by viral respiratory pathogens such as, for example the Influenza virus and/or Parainfluenza virus and bacterial pathogens such as, for example, *Haemophilus* sp and *Streptococcus* pneumoniae. Thus, the invention provides sialic acid binding molecules, which may be used to modulate (enhance, stimulate and/or increase) an immune response which facilitates the clearance and/or resolution of a respiratory disease with a viral, bacterial, protozoan and/or fungal aetiology. For example, the invention may be exploited so as to stimulate, enhance and/or increase immune responses which are beneficial to and/or facilitate the treatment and/or prevention of diseases and/or conditions caused or contributed to by, for example, viruses belonging to the Orthomyxoviridae or Paramyxoviridae families and certain *Haemophilus* and/or *Streptococcus* bacteria. These diseases and/or conditions may include, but are not limited to, influenza and viral and/or bacterial respiratory diseases such as croup, pneumonia and bronchitis.

As stated, the present invention should not be regarded as limited to the treatment and/or prevention of infections and/or diseases which are caused or contributed to by respiratory pathogens; rather, the invention provides compounds which modulate immune responses such that they are better able to cope with diseases and/or infections caused or contributed to by a variety of different pathogens. For example, the invention may find application in the treatment and/or prevention of diseases and/or infections caused or contributed to by microbial pathogens which do not necessarily exploit the presence of cell surface sialic acid moieties—but which may still cause infection and/or disease in a host. For example, the inventors have discovered that the sialic acid binding molecules of this invention may be used to modulate (enhance, stimulate or improve) immune responses which facilitate the clearance of viruses belonging to the Herpesviridae family and/or resolution of diseases caused or contributed to thereby. For example, the invention may be applied to the treatment and/or prevention of infections or diseases caused or contributed to by, for example, gammaherpesvirina.

Additionally, the inventors have discovered that in addition to priming the immune system to provide protection against the development of clinically significant disease following infection, a degree of pathogen (for example viral) replication may still occur within the host. This "baseline" level of pathogen replication ensures that following administration of a sialic acid binding protein of this invention (which administration modulates the host immune response) the host remains able to mount an immune response, which may offer protection against future pathogen exposure. Indeed, the data shows that in the case of a viral infection, the administration of a sialic acid binding molecule prior to infection not only prevents subsequent infection (by priming and/or modulating the immune system to the benefit of the host) there remains a detectable viral titre and antibodies specific for the pathogen are generated by the host which antibodies offer protection against subsequent infections.

As such, when administered to a subject in advance of any infection occurring, the immunomodulatory compounds of this invention may, through modulation of the immune system and immune system priming, facilitate reducing the pathogen load which in turn helps clear the infection and reduce clinical symptoms.

The term "sialic acid" as used herein, embraces all forms of N- or O-substituted neuraminic acid and includes all synthetic, naturally occurring and/or modified forms thereof.

Sialic acids may be found as components of cell surface molecules, glycoproteins and glycolipids. Most often, sialic acids are present at the end (terminal regions) of sugar chains connected to cell membranes and/or proteins. The sialic acid family encompasses a number (approximately 50) of derivatives that may result from acetylation, glycolylation, lactonisation and methylation at C4, C5, C7, C8 and C9. All such derivatives are to be embraced by the term "sialic acid".

Furthermore, sialic acids are found linked α(2,3) or α(2,6) to Gal and GalNAc or α(2,8) or α(2,9) to another sialic acid. Accordingly, it is important to understand that while the term "sialic acid" is used throughout this specification, it encompasses all derivatives, analogues or variants (either naturally occurring or synthetically generated) thereof as well as monomers, dimers, trimers, oligomers, polymers or concatamers comprising the same.

A sialic acid binding molecule of this invention exhibits an affinity for sialic acid—including all forms of sialic acid described above and in particular sialic acid present on the surface of mammalian cells. For example, the molecules of this invention may exhibit an affinity for cell membrane receptors, which comprise sialic acid. Cell receptors of this type may be present on the surface of epithelial cells—including epithelial cells of the mucosal and respiratory tracts. A number of pathogens, including viral and/or bacterial pathogens may express molecules, which exhibit an affinity for sialic acid. Pathogens of this type have evolved to exploit cell surface sialic acid moieties as a means to bind to host cells. Once bound to a cell via, for example a host cell surface bound sialic acid moiety, a pathogen may colonise the cell surface and/or infect/enter the cell.

The sialic acid binding molecules of this invention may exhibit an affinity for α-2,6-linked sialic acid receptors predominantly present on cells of the human upper respiratory tract. Additionally or alternatively, the sialic acid binding receptors may exhibit an affinity for α-2,3-linked sialic acid receptors present on cells of the upper and lower respiratory tracts. It should be understood that molecules, which exhibit an affinity for sialic acid, bind to or otherwise couple to or associate with sialic acid moieties. Thus the term "sialic acid binding molecule" may encompass any fragment, which retains an ability to bind to or otherwise couple or associate with a sialic acid moiety.

A sialic acid binding molecule of this invention may comprise a single molecule capable of binding sialic acid (a monomeric or monovalent molecule, for example) or, alternatively, two or more sialic acid binding molecules (which may all be the same or different—a polymeric or multivalent molecule, for example).

A sialic acid binding molecule of this invention may comprise one or more molecules known as "carbohydrate binding modules" (CBMs). Suitable CBMs may exhibit an affinity for sialic acid. Exemplary carbohydrate binding modules for use in this invention may comprise the sialic acid binding domain of *Vibrio cholerae* NanH sialidase (VcCBM) and/or the equivalent (or homologous) domain from *Streptococcus pneumoniae* NanA sialidase (SpCBM).

Of course similar or homologous sialic acid binding modules present in other organisms are to be encompassed within the scope of the term "CBM".

An exemplary *Vibrio cholerae* NanH sialidase amino acid sequence is deposited under accession umber A5F7A4 and is reproduced below as SEQ ID NO: 1 (781 amino acids).

```
MRFKNVKKTA LMLAMFGMAT SSNAALFDYN ATGDTEFDSP
AKQGWMQDNT NNGSGVLTNA DGMPAWLVQG IGGRAQWTYS
LSTNQHAQAS SFGWRMTTEM KVLSGGMITN YYANGTQRVL
PIISLDSSGN LVVEFEGQTG RTVLATGTAA TEYHKFELVF
LPGSNPSASF YFDGKLIRDN IQPTASKQNM IVWGNGSSNT
DGVAAYRDIK FEIQGDVIFR GPDRIPSIVA SSVTPGVVTA
FAEKRVGGGD PGALSNTNDI ITRTSRDGGI TWDTELNLTE
QINVSDEFDF SDPRPIYDPS SNTVLVSYAR WPTDAAQNGD
RIKPWMPNGI FYSVYDVASG NWQAPIDVTD QVKERSFQIA
GWGGSELYRR NTSLNSQQDW QSNAKIRIVD GAANQIQVAD
GSRKYVVTLS IDESGGLVAN LNGVSAPIIL QSEHAKVHSF
HDYELQYSAL NHTTTLFVDG QQITTWAGEV SQENNIQFGN
ADAQIDGRLH VQKIVLTQQG HNLVEFDAFY LAQQTPEVEK
DLEKLGWTKI KTGNTMSLYG NASVNPGPGH GITLTRQQNI
SGSQNGRLIY PAIVLDRFFL NVMSIYSDDG GSNWQTGSTL
PIPFRWKSSS ILETLEPSEA DMVELQNGDL LLTARLDFNQ
IVNGVNYSPR QQFLSKDGGI TWSLLEANNA NVFSNISTGT
VDASITRFEQ SDGSHFLLFT NPQGNPAGTN GRQNLGLWFS
FDEGVTWKGP IQLVNGASAY SDIYQLDSEN AIVIVETDNS
NMRILRMPIT LLKQKLTLSQ N
```

The CBM region of SEQ ID NO: 1 is from amino acid residue 25 to 216—this sequence may be SEQ ID NO: 2.

An exemplary *Streptococcus pneumoniae* NanA sialidase amino acid sequence has been deposited under accession number P62575 and is reproduced below as SEQ ID NO: 3 (1035 amino acids).

```
MSYFRNRDID IERNSMNRSV QERKCRYSIR KLSVGAVSMI
VGAVVFGTSP VLAQEGASEQ PLANETQLSG ESSTLTDTEK
SQPSSETELS GNKQEQERKD KQEEKIPRDY YARDLENVET
VIEKEDVETN ASNGQRVDLS SELDKLKKLE NATVHMEFKP
DAKAPAFYNL FSVSSATKKD EYFTMAVYNN TATLEGRGSD
GKQFYNNYND APLKVKPGQW NSVTFTVEKP TAELPKGRVR
LYVNGVLSRT SLRSGNFIKD MPDVTHVQIG ATKRANNTVW
GSNLQIRNLT VYNRALTPEE VQKRSQLFKR SDLEKKLPEG
AALTEKTDIF ESGRNGKPNK DGIKSYRIPA LLKTDKGTLI
AGADERRLHS SDWGDIGMVI RRSEDNGKTW GDRVTITNLR
DNPKASDPSI GSPVNIDMVL VQDPETKRIF SIYDMFPEGK
GIFGMSSQKE EAYKKIDGKT YQILYREGEK GAYTIRENGT
```

-continued

```
VYTPDGKATD YRVVVDPVKP AYSDKGDLYK GNQLLGNIYF
TTNKTSPFRI AKDSYLWMSY SDDDGKTWSA PQDITPMVKA
DWMKFLGVGP GTGIVLRNGP HKGRILIPVY TTNNVSHLNG
SQSSRIIYSD DHGKTWHAGE AVNDNRQVDG QKIHSSTMNN
RRAQNTESTV VQLNNGDVKL FMRGLTGDLQ VATSKDGGVT
WEKDIKRYPQ VKDVYVQMSA IHTMHEGKEY IILSNAGGPK
RENGMVHLAR VEENGELTWL KHNPIQKGEF AYNSLQELGN
GEYGILYEHT EKGQNAYTLS FRKFNWDFLS KDLISPTEAK
VKRTREMGKG VIGLEFDSEV LVNKAPTLQL ANGKTARFMT
QYDTKTLLFT VDSEDMGQKV TGLAEGAIES MHNLPVSVAG
TKLSNGMNGS EAAVHEVPEY TGPLGTSGEE PAPTVEKPEY
TGPLGTSGEE PAPTVEKPEY TGPLGTAGEE AAPTVEKPEF
TGGVNGTEPA VHEIAEYKGS DSLVTLTTKE DYTYKAPLAQ
QALPETGNKE SDLLASLGLT AFFLGLFTLG KKREQ
```

The CBM region of SEQ ID NO: 3 is from amino acid residue 121 to 305—this sequence may be SEQ ID NO: 4.

A suitable CBM may comprise a proteinaceous moiety encoded by the sialic acid binding domain of the nanH gene (encoding sialidase) of *V. cholerae* or an equivalent or homologous gene present in another organism (for example the equivalent/homologous nanA sialidase gene of *S. pneumoniae*). For example, a sialic acid binding molecule of this invention may comprise from about residue 1, 5, 10, 15, 25 or 30 (i.e. from 1-30 or from any amino acid residue there between) to about residue 150, 175, 200, 210, 216, 220-781 (to any residue from 150 to 781 including any residue therebetween) of the *V. cholerae* sialidase. The sialic acid binding domain may comprise from about residue 25 to about residue 216.

A further suitable CBM may comprise a proteinaceous moiety encoded by the sialic acid binding domain of the *Streptococcus pneumoniae* nanA gene (encoding sialidase). For example a sialic acid binding molecule of this invention may comprise from about residue 80, 90, 100, 110, 120, 121 to 130 (i.e. from any of about residues 80 to 130 including any residue therebetween) to about residue 250, 275, 300, 305, 310, 320-1035 (i.e. to any residue from about 250-1035 including to about any residue therebetween) of the *S. pneumoniae* sialidase. The sialic acid binding domain may comprise from about residue 121 to about residue 305.

A sialic acid binding molecule of this invention may comprise one or more CBMs. For example suitable sialic acid binding molecules may comprise single CBMs—for example a single VcCBM or a single SpCBM. Alternatively, the sialic acid binding molecules may comprise a plurality or multiple (i.e. two or more) CBMs. Sialic acid binding molecules, which comprise a plurality of CBMs may be termed "multivalent sialic acid binding molecules" or "multivalent CBMs". A multivalent CBM may, for example, comprise two or more VcCBMs or two or more SpCBMs. A multivalient CBM may comprise a mixture of different CBMs, for example one or more VcCBMs with one or more SpCBMs.

A multivalent sialic acid binding molecule of this invention may further comprise an oligomerisation domain. Suitable oligomerisation domains may exhibit an ability to self-associate to form multimer structures, for example trimers. For example one or more (for example two) sialic acid binding molecules (for example CBMs) may be bound, coupled or fused to an oligomerisation domain. The oligomerisation domain may comprise any molecule with the above mentioned properties or any functional fragment thereof.

Suitable oligomerisation domains may be derived from, for example, *Pseudomonas aeruginosa* pseudaminidase. An exemplary *Psedomonas aeruginosa* pseudaminidase sequence amino acid sequence has been deposited under accession number PA0579 and is reproduced below as SEQ ID NO: 5 (438 amino acids).

```
MNTYFDIPHR LVGKALYESY YDHFGQMDIL SDGSLYLIYR

RATEHVGGSD GRVVFSKLEG GIWSAPTIVA QAGGQDFRDV

AGGTMPSGRI VAASTVYETG EVKVYVSDDS GVTWVHKFTL

ARGGADYNFA HGKSFQVGAR YVIPLYAATG VNYELKWLES

SDGGETWGEG STIYSGNTPY NETSYLPVGD GVILAVARVG

SGAGGALRQF ISLDDGGTWT DQGNVTAQNG DSTDILVAPS

LSYIYSEGGT PHVVLLYTNR TTHFCYYRTI LLAKAVAGSS

GWTERVPVYS APAASGYTSQ VVLGGRRILG NLFRETSSTT

SGAYQFEVYL GGVPDFESDW FSVSSNSLYT LSHGLQRSPR

RVVVEFARSS SPSTWNIVMP SYFNDGGHKG SGAQVEVGSL

NIRLGTGAAV WGTGYFGGID NSATTRFATG YYRVRAWI
```

The trimerisation domain of SEQ ID NO: 5 is from amino acid residue 333 to 438—this sequence may be SEQ ID NO: 6.

An oligomerisation domain for use in this invention may comprise from about residue 250, 275, 300, 310, 320, 333, 340 to 350 (i.e. from about residue 250 to about residue 350 including from about any residue therebetween) to about residue 400, 410, 420, 430 or 438 (i.e. to about any residue from about residue 400 residue 438 including to about any residue therebetween) of the *P. aeruginosa* pseudaminidase trimerisation domain (PaTD). Suitable trimerisation domains may comprise residues 333 to 438 of SEQ ID NO: 6.

In view of the above, the terms "sialic acid binding molecule" or "carbohydrate binding module" encompass each of the multivalent molecules shown in FIG. 1d.

Without wishing to be bound by theory, the inventors have discovered that while individual sialic acid binding proteins might exhibit a low affinity for sialic acid, multivalent molecules comprising two or more sialic acid binding molecules (for example two or more CBMs) exhibit improved affinity through avidity.

Thus this invention provides multivalent sialic acid binding molecules comprising, for example, one or more VcCBM or SpCBM for use in (a method of) modulating an immune response in a subject. The invention may exploit one or more of the multivalent sialic acid binding proteins described in FIG. 1.

For example, the multivalent sialic acid binding molecule may comprise two or more VcCBMs optionally fused, bound or conjugated to an oligomerisation domain (such as a PaTD or fragment thereof) for use in (a method of) modulating an immune response in a subject. The multivalent sialic acid molecule for use in (a method of) modulating an immune response in a subject may comprise, consist or consist essentially of two fused (or bound) VcCBMs which are in turn fused to an oligomerisation domain (see, for example, molecule Vc2CBMTD shown in FIG. 1).

The invention may further provide a multivalent sialic acid molecule comprising two or more SpCBM optionally fused, bound or conjugated to an oligomerisation domain (such as a PaTD or a fragment thereof) for use in a method of modulating an immune response in a subject. The multivalent sialic acid molecule for use in modulating an immune system may comprise, consist or consist essentially of two fused (or bound) SpCBM which are in turn fused to an oligomerisation domain (see, for example, molecule Sp2CBMTD shown in FIG. 1).

It should be understood that the various multivalent CBMs (including Vc2CBMTD and Sp2CBMTD as shown in FIG. 1) may find application in methods of modulating immune responses in subjects, the methods comprising the administration of an immunomodulatory amount of the multivalent CBM.

The inventors have noted that even when administered to subjects in small doses, the sialic acid binding molecules of this invention induce protection against infection from a subsequent challenge by a respiratory (for example viral and/or bacterial) pathogen. The duration of protection may last anywhere between about 1 and about 21 days—the actual duration may depend on the form of the sialic acid binding molecule and/or the dose at which the molecule is administered (or is intended to be administered). The "duration of protection" may be defined as the period following administration to a subject of a sialic acid binding protein of this invention, during which, following an infection, that subject does not develop disease or substantially no clinical symptoms thereof. The duration of protection may last approximately 14 days, or approximately 7 days. The duration of protection may last from about 1 day to about 2, 3, 4, 5 or 6 days.

The present invention provides compositions, for example pharmaceutical compositions comprising any of the sialic acid binding molecules described herein. The compositions may find application as medicaments for use in modulating immune responses or in the methods of modulating immune responses described herein.

The sialic acid binding proteins of this invention may be formulated and/or prepared for, for example, oral, parenteral, topical and/or mucosal/inhalation administration. For example, the sialic acid binding proteins of this invention may be formulated as sterile pharmaceutical compositions suitable for administration to subjects. Such formulations may comprise pharmaceutically acceptable excipients, carriers or diluents including, for example, water, saline, phosphate buffered saline, dextrose, glycerol, ethanol, ion exchangers, alumina, aluminium stearate, lecithin, serum proteins, such as serum albumin, buffer substances such as phosphates, glycine, sorbic acid, potassium sorbate, partial glyceride mixtures of saturated vegetable fatty acids, water salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycon, sodium carboxymethylcellulose, polyacrylates, waxes, polyethylene-polypropylene-block polymers, polyethylene glycol and wool fat and the like, or combinations thereof.

Compositions formulated for topical administration may be presented as an ointment, solution or a suspension in an aqueous or non-aqueous liquid, or as an oil-in-water liquid emulsion.

Compositions formulated or prepared for parenteral administration (such as by subcutaneous, intradermal, intramuscular and/or intravenous injection), may comprise aqueous or oleaginous suspensions formulated according to the known art using suitable dispersing, wetting and/or suspending agents. In this regard, one of skill will appreciate that an acceptable carrier, diluents and/or excipient may comprise 1,3-butanediol, water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may find use in the preparation of injectable compositions according to this invention.

Compositions suitable (or formulated) for mucosal administration may include compositions, which are intended to be administered intranasally. Such compositions may comprise solutions of the sialic acid binding molecule(s) to be administered and/or particles (comprising the same) for aerosol dispersion, or dispensed in drinking water. When dispensed such compositions should desirably have a particle diameter in the range 10 to 200 microns to enable retention in, for example, the nasal cavity; this may be achieved by, as appropriate, use of a powder of a suitable particle size or choice of an appropriate valve.

Other suitable compositions include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

One of skill will appreciate that the sialic acid binding proteins of this invention—particularly the CBM based (mono/multi-valent molecules of this invention) may be provided in the form of a vector for introduction and expression in a cell.

A composition of this invention (namely a composition comprising a sialic acid binding protein) may further comprise one or more additional components—such as, for example other therapeutic moieties, vaccine components, adjuvants (i.e. any agent which enhances or promotes the immune response of an immunised host) and the like.

The compositions of this invention may be administered as single or multiple dosages of an effective amount. For example, two or more doses may be administered over a predetermined period of time.

By way of example, an initial dose may be administered followed by one or more "booster" doses (secondary doses) given at 1, 2, 3, 4, 5, 6, 7, 8, 9 and/or 10 week intervals after the initial dose.

The sialic acid binding molecules of this invention may be administered to a subject in need thereof (for example administered to mucosal tissues and/or intranasally or by aerosol into the lung) as one or more doses to a healthy subject. A healthy subject being a subject not suffering from a disease or condition caused or contributed to by a microbial pathogen such as, for example, a microbial respiratory pathogen. Sialic acid molecules administered up to about 10 days, for example 1, 2, 3, 4, 5, 6 and/or 7 days prior to an infection have been shown to offer protection against subsequent pathogen challenges.

The various sialic acid binding proteins, CBMs and/or Sp2CBMTD of this invention may be administered at a dose of about 0.1, 1, 10, and 100 µg/subject/day. A sialic acid binding protein, CBM and/or Sp2CBMTD of this invention may be administered to a healthy subject one or more times prior to infection or a likely infection. A sialic acid binding protein, CBM and/or Sp2CBMTD of this invention may be administered parenterally, orally and/or intranasally.

As stated, the inventors have noted that when administered intranasally, a single 1 µg dose of a multivalent sialic acid binding protein of this invention—in particular a Sp2CBMTD molecule as described in FIG. 1, can prime (or stimulate) the immune system to offer up to about up to about 7, 14 or 21 days of protection against challenge with a pathogen, for example a respiratory pathogen. Moreover, a 0.1 µg/subject/day dose of Sp2CBMTD administered prior to an influenza H7N9 infection, was sufficient to offer complete protection against disease and subsequent infection.

The invention provides a sialic acid binding molecule for use in modulating an immune response in a subject, wherein the sialic acid binding molecule is administered to a mucosal tissue and/or intranasally.

Additionally, the invention provides a sialic acid binding molecule for use in a method of modulating an immune response in a subject, wherein the method comprises administering an immunomodulatory amount of the sialic acid binding molecule to a mucosal tissue and/or intranasally.

In view of the above, the invention may provide vaccine compositions comprising one or more of the sialic acid binding molecules described herein. The vaccine compositions of this invention may be formulated for parenteral, mucosal (aerosol/intranasal) and/or oral administration. The sialic acid binding molecules of this invention may be administered separately or concurrent with a vaccine. When administered separately, the sialic acid binding molecules may be administered to a subject before and/or after a vaccine. Thus the invention provides a method of vaccinating a subject, wherein the subject is administered a vaccine together (concurrently or separately) with a sialic acid binding molecule of this invention. The invention may further relate sialic acid binding molecules for use in protecting subjects from disease by vaccination, wherein the sialic acid binding proteins are (to be) administered together (concurrently or separately) with a vaccine.

A composition of this invention (namely a composition comprising a sialic acid binding protein) may further comprise one or more additional components—such as, for example other therapeutic moieties, vaccine components, adjuvants (i.e. any agent which enhances or promotes the immune response of an immunised host) and the like.

In a further aspect, the invention provides nucleic acids encoding any of the sialic acid binding molecules of this invention including, for example the CBMs or sialic acid binding CBM fragments described herein. Moreover, the invention provides oligonucleotide and/or primer sequences, which are complementary to parts of the gene sequences encoding the sialic acid binding molecules of this invention. One of skill will appreciate that oligonucleotides and/or primers of this type are useful in methods for the recombinant production of sialic acid binding molecules for use in this invention.

Additionally, the invention provides nucleic acids, which comprise sequences encoding sialic acid binding molecules. Such sequences may comprise DNA and/or RNA. A nucleic acid sequence of this invention may take the form of a vector or plasmid, for example an expression vector, which is suitable for use in recombinant technologies. A nucleic acid sequence of this invention may be operatively linked to a transcription regulation factor and/or fused (directly or indirectly) to a sequence encoding a tagging moiety. A nucleic acid of this invention may further comprise a sequence encoding an oligomerisation domain.

One of skill in this field will appreciate that any of the sialic acid binding molecules of this invention may be prepared using recombinant technology in which, for example a host cell is transformed with a vector comprising a sialic acid binding molecule encoding nucleic acid sequence. Recombinantly produced sialic acid binding molecules may comprise "tags" or "labels" which may be exploited in affinity purification techniques to achieve the purification and/or isolation of a sialic acid binding molecule from a heterogeneous population of proteins and other material.

In view of the above, the invention provides a host cell transformed with a nucleic acid and/or vector of this invention. The host cell may be a microbial (for example bacterial host cell) or a mammalian cell.

Accordingly, this invention provides a fusion protein comprising a sialic acid binding molecule of this invention fused, joined, bound or conjugated to a heterologous protein, for example a detectable (perhaps optically detectable) moiety and/or an affinity purification moiety (for example a His or GST tag). The fusion proteins of this invention may comprise a CBM (or sialic acid binding fragment thereof) and an oligomerisation domain bound, conjugated, joined or fused thereto. Fusion proteins of this type may find application in the generation of multivalent sialic acid binding molecules (for example multivalent CBMs).

In a further aspect, the invention may provide any of the sialic acid binding proteins of this invention for use in treating or preventing diseases and/or infections caused or contributed to by any of the abovementioned pathogens—including, for example, the sialic acid exploiting, viral, bacterial, protozoan and/or fungal pathogens disclosed herein. For example, any of the sialic acid molecules of this invention may be for use in medicine. Moreover, the CBM molecules disclosed in FIG. 1 may find application as medicaments or compositions for use treating or preventing respiratory diseases or in methods for treating respiratory diseases.

The invention further provides any of the sialic acid binding molecules as described in the description and Figures of this application. For example, the invention provides one or more of the sialic acid binding molecules described in FIG. 1.

The invention also provides any of the sialic acid binding proteins of this invention, including, for example, Sp2CBMTD, for use in treating influenza, including, H7N9 influenza. Also disclosed is the use of the sialic acid binding proteins of this invention, including, for example, Sp2CBMTD, for the manufacture of medicaments for treating influenza, including, H7N9 influenza. The invention also provides a method of treating influenza, including H7N9 influenza, said method comprising administering a subject in need thereof, a therapeutically effective amount of a sialic acid binding protein of this invention and/or Sp2CBMTD. Without wishing to be bound by theory, the inventors have noted that the administration of Sp2CBMTD does not affect development of anti-HA antibodies following challenge and the level of immune response was sufficient to protect against H7N9 virus re-infection—including re-infection with higher doses of virus.

DETAILED DESCRIPTION

The present invention will now be described with reference to the following invention, which show:

FIG. 1. Building blocks of the multivalent CBM forms and their affinities for sialic acid. a, VcCBM, residues 25-216 of the *V. cholerae* sialidase (PDB:1w0p) with α-2,3-sialyllactose drawn as spheres. b, SpCBM, residues 121-305 of *S. pneumoniae* NanA sialidase with α-2,3-sialyllactose (PDB:4c1w). c, TD, the trimerisation domain, residues 333-438, of the *P. aeruginosa* sialidase (PDB:2w38) in rainbow colors; the other two monomers in single colors. d, Multivalent forms: their molecular weights, valencies and binding affinities for α2,3-sialyllactose as determined by surface plasmon resonance (SPR) at 25° C. ($K_D$ values for VcCBM, Vc2CBM and Vc3CBM had been reported previously[8]). Tandem repeat CBMs, and oligomeric CBMs fused to TD are linked by a 5-amino linker (details in Full Methods).

Figure 2:
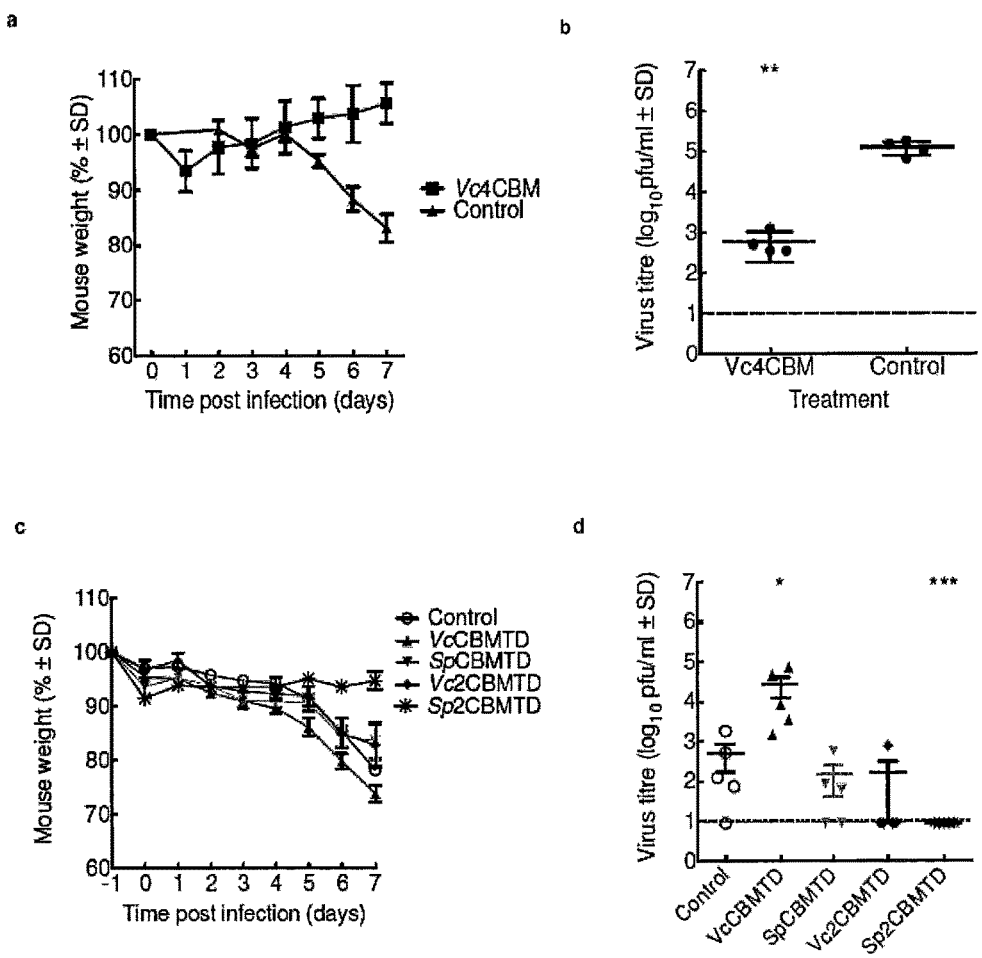

FIG. 2. Weight changes and lung viral titres of BALB/c mice after lethal challenge with A/WSN/1933 (H1N1) influenza virus. a, Weight changes in mice (n=4) after single intranasal administration of 500 µg of Vc4CBM, or BSA (control), immediately prior to viral challenge. b, Lung viral titres in mice determined 7 days p.i. c, Weight changes in mice (n=4) after single intranasal administration of trimeric (VcCBMTD, SpCBMTD, 400 µg) or hexameric (Vc2CBMTD, Sp2CBMTD, 100 µg) biologics, or PBS (control), immediately prior to viral challenge. d, Lung virus titres in mice determined 7 days p.i. Dashed line indicates the limit of virus detection. Bars represent means±s.d. for each treated and control groups. *$p<0.05$, $p<0.001$, *$p<0.0001$.

Figure 3:
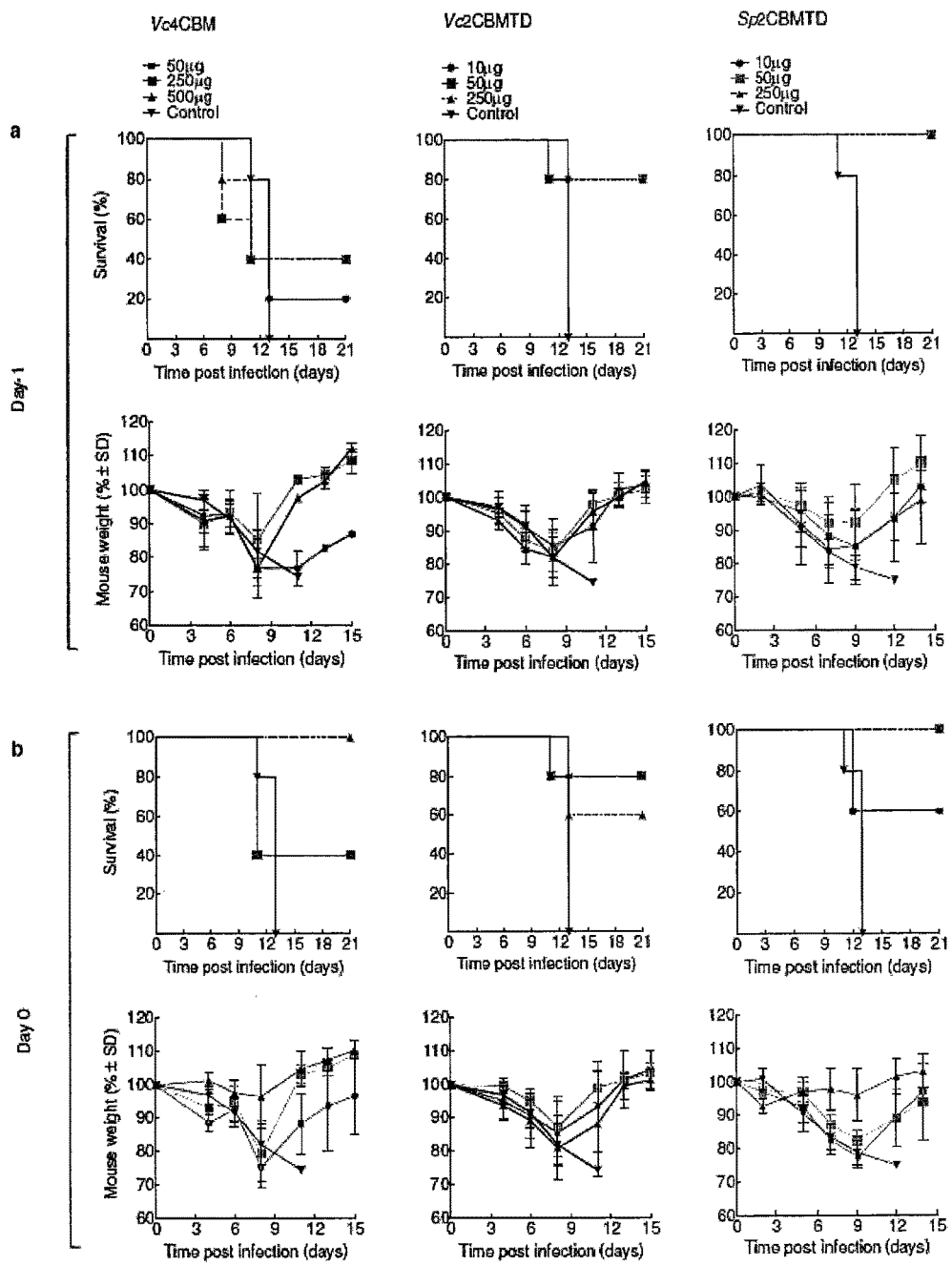

FIG. 3. Effect of prophylactic administration of mCBMs in BALB/c mice given a lethal challenge with mouse-adapted A/California/04/2009 (H1N1) influenza virus. a, Survival and weight changes of mice (n=5) after a single intranasal dose (50, 250 or 500 µg) of Vc4CBM or (10, 50 or 250 µg) of Vc2CBMTD or Sp2CBMTD given on day −1 prior to viral challenge. b Survival and weight changes of mice (n=5) after the same single intranasal doses of the three biologics given on day 0, immediately prior to viral challenge.

Survival curves are shown in top panel with corresponding weight loss curves in the bottom panel for each administration day where each value represents mean body weight±s.d. for five mice.

Figure 4:
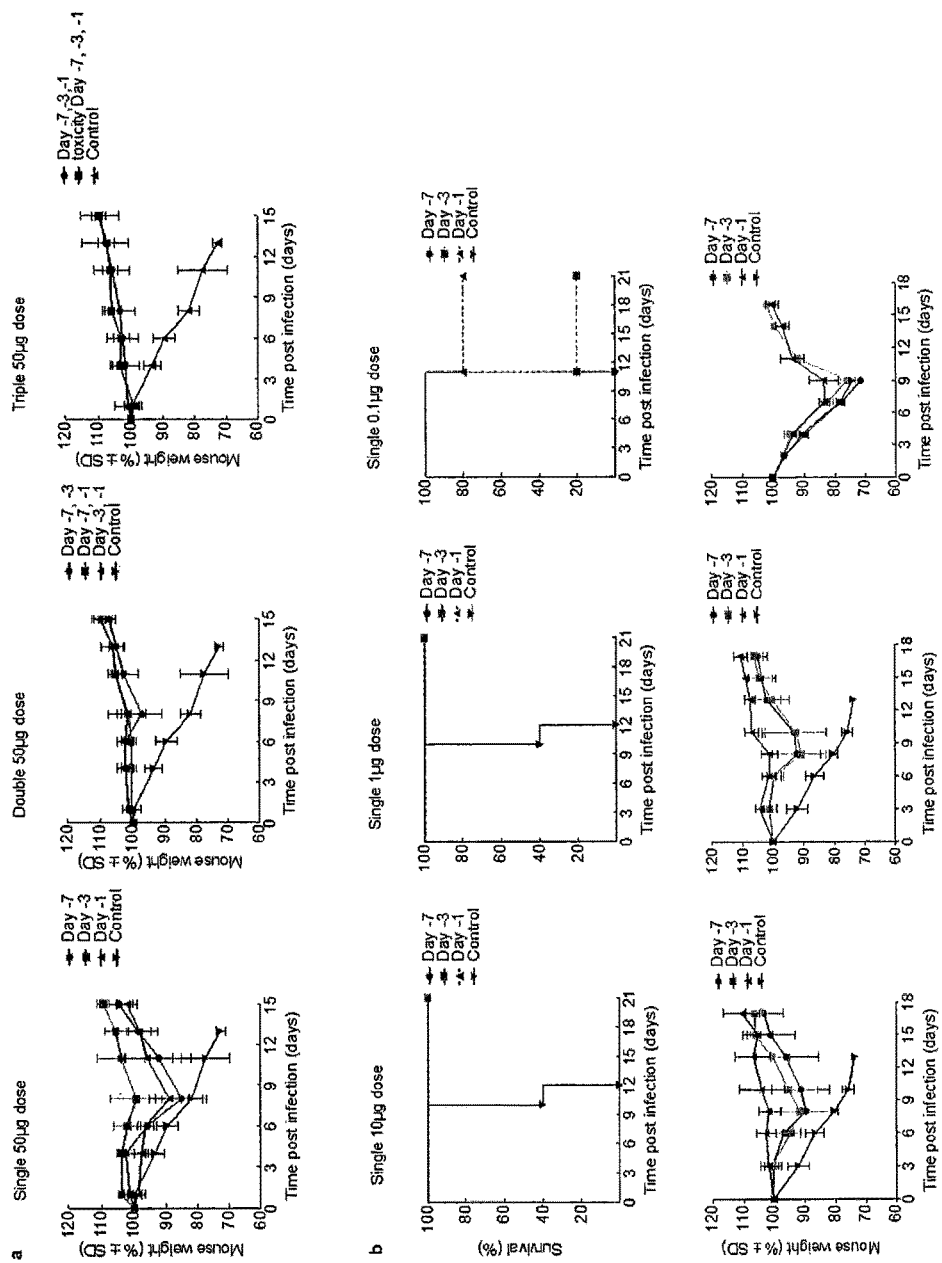

FIG. 4. Survival and weight changes of BALB/c mice administered with Sp2CBMTD prior to a lethal challenge with mouse-adapted A/California/04/2009 (H1N1) influenza virus. a BALB/c mice (n=5) were given single, double or triple intranasal doses of Sp2CBMTD (50 µg) on days −7, −3 or −1 prior to viral challenge on day 0. Mice were also given a triple intranasal dose of Sp2CBMTD alone to determine toxicity of biologic (weight change shown in blue, last panel). b, Survival and weight changes of mice (n=5) after single intranasal doses of Sp2CBMTD (10, 1 or 0.1 µg) given on days −7, −3 or −1 prior to viral challenge. Survival curves are shown in top panel with corresponding weight loss curves in the bottom panel for each administration day. In all cases, control animals were infected and untreated. Each value represents mean body weight±s.d. for five mice.

Figure 5:
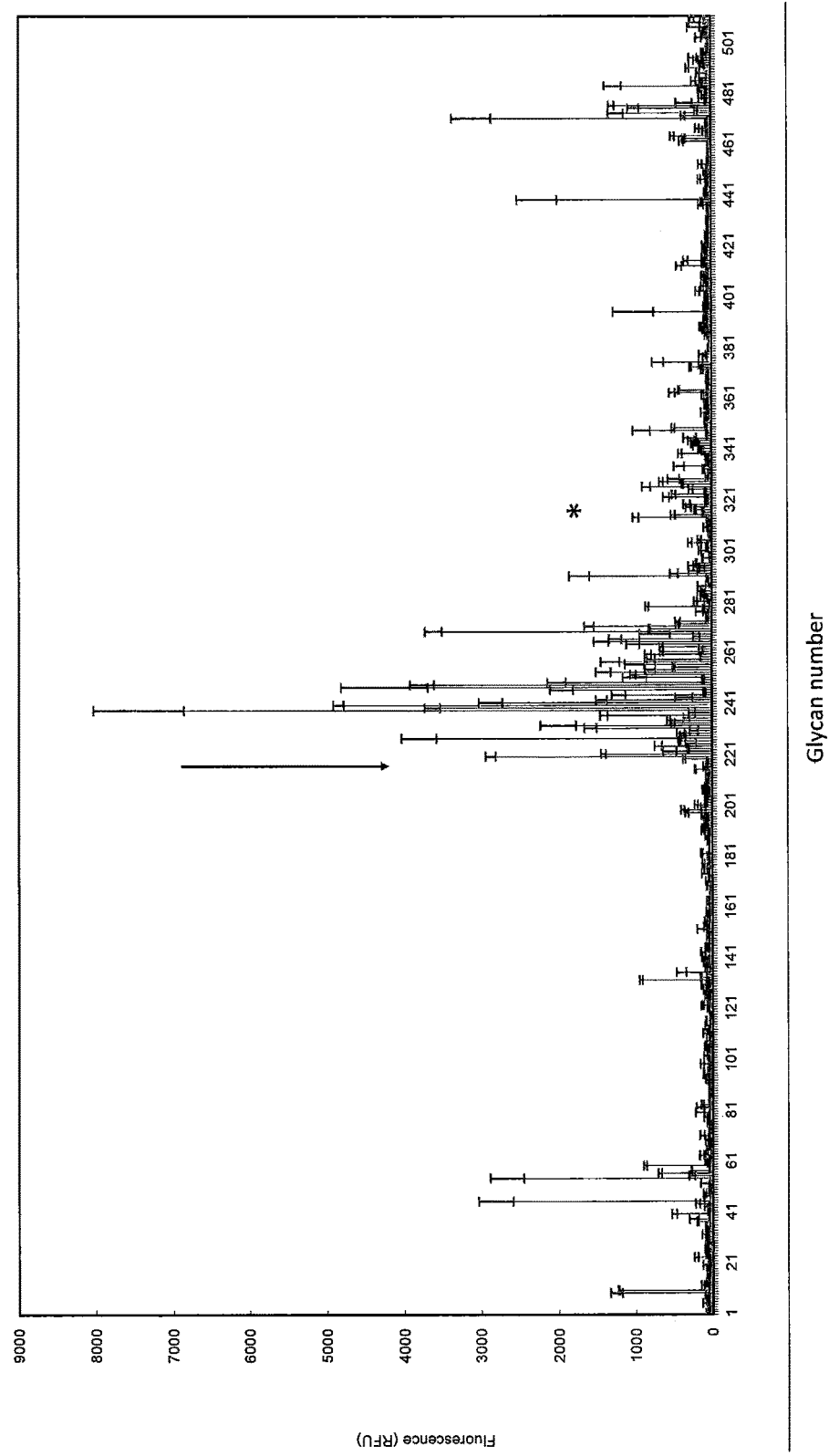

FIG. 5. Glycan array screen for SpCBM showing its specificity and promiscuity for terminal sialic acid glycans. Glycan binding of GFP-fused SpCBM, using glycan array v4.2 consisting of 511 glycans (Consortium for Functional Glycomics), is expressed as relative fluorescence units (RFU). The top 40 hits are all sialosides, of which only the first 29 glycans are listed in decreasing order of RFU. Error bars indicate the standard error of the mean (SEM) in the signal for four independent replicates. Confidence value, % CV=100×StDev/mean RFU.

Figure 6:
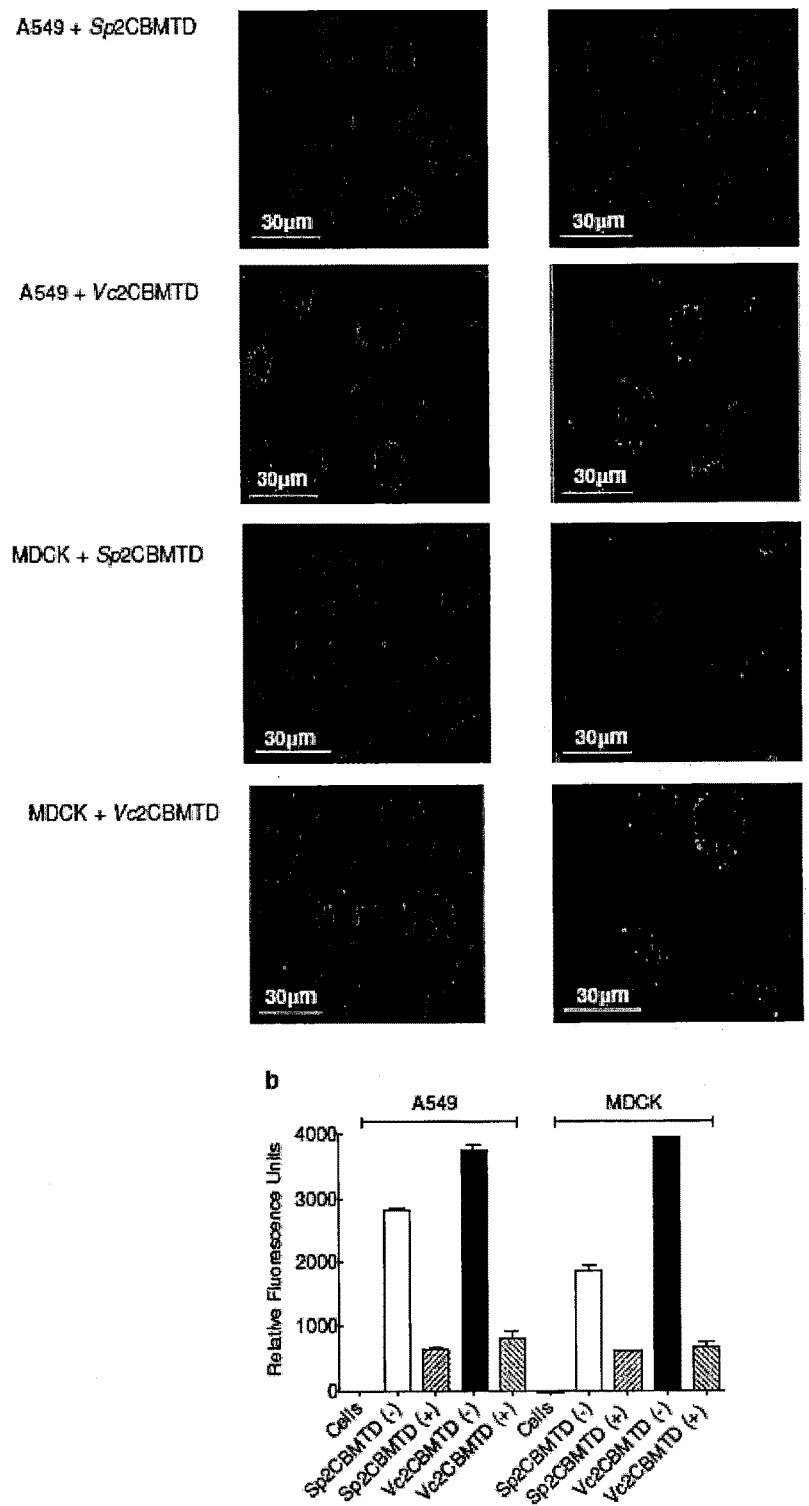

FIG. 6. Cell binding of Sp2CBMTD and Vc2CBMTD with and without pretreatment with sialidase. Mammalian A549 and MDCK cells were either treated with or without the catalytic domain of S. pneumoniae NanA sialidase prior to incubation with Sp2CBMTD and Vc2CBMTD, followed by incubation with rabbit anti-SpCBM and anti-VcCBM antibodies, respectively, before incubation with Alexa Fluor 488-labelled anti-rabbit IgG antibody. a, Live images of A549 and MDCK cells showing mCBM binding (green) to cell surface receptors (left panels), compared with cells that are pre-treated with sialidase (right panels). Nuclei are stained using DAPI (blue). b, Relative fluorescence units (RFU) of mCBM binding to cells when treated with or without sialidase. Bars represent means±s.d. for each treated and untreated groups.

Figure 7:
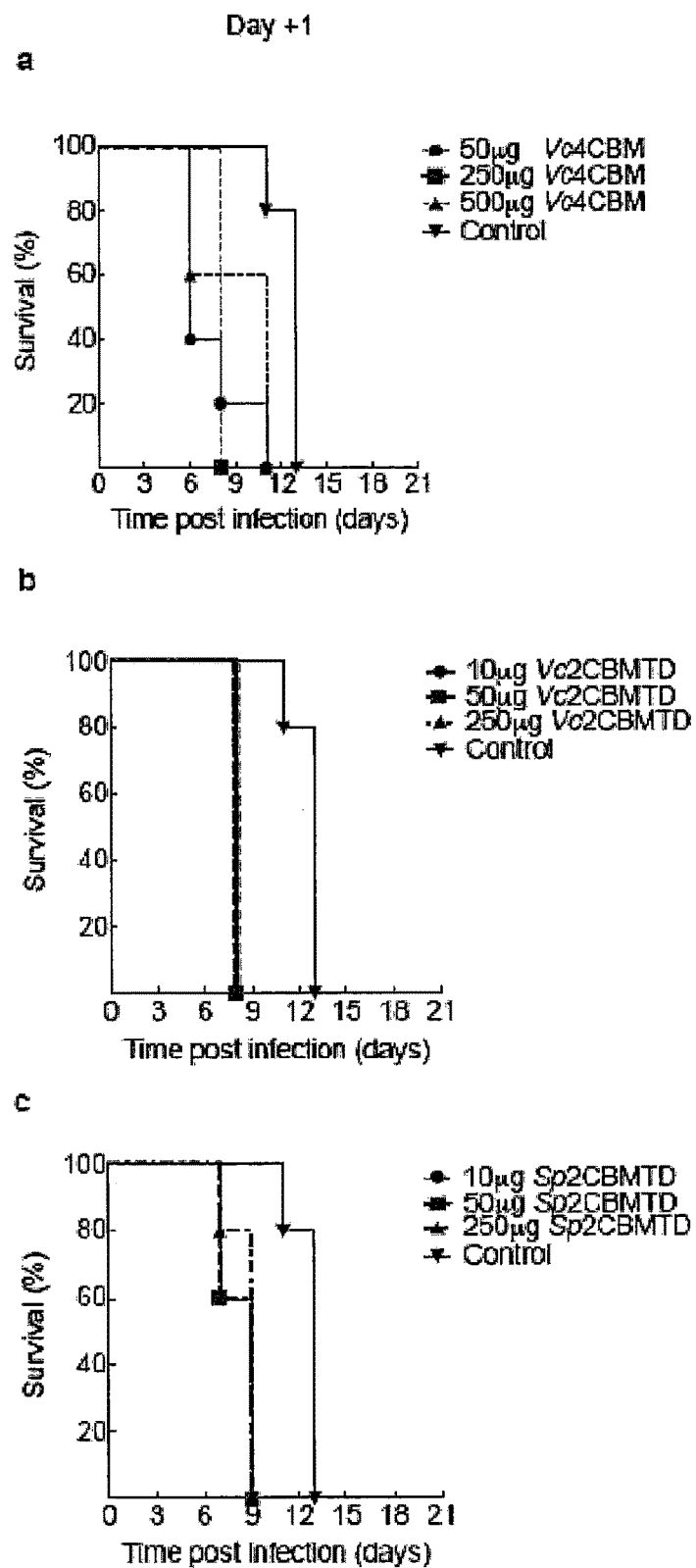

FIG. 7. Survival of BALB/c mice administered with mCBMs 24 h after challenge with mouse-adapted A/California/04/2009 (H1N1) influenza virus. BALB/c mice (n=5) were intranasally administered with a single dose of Vc4CBM (a), Vc2CBMTD (b) or Sp2CBMTD (c) one day after viral challenge and monitored for survival. Graphs represent the survival curves of different doses of each mCBM.

Figure 8:
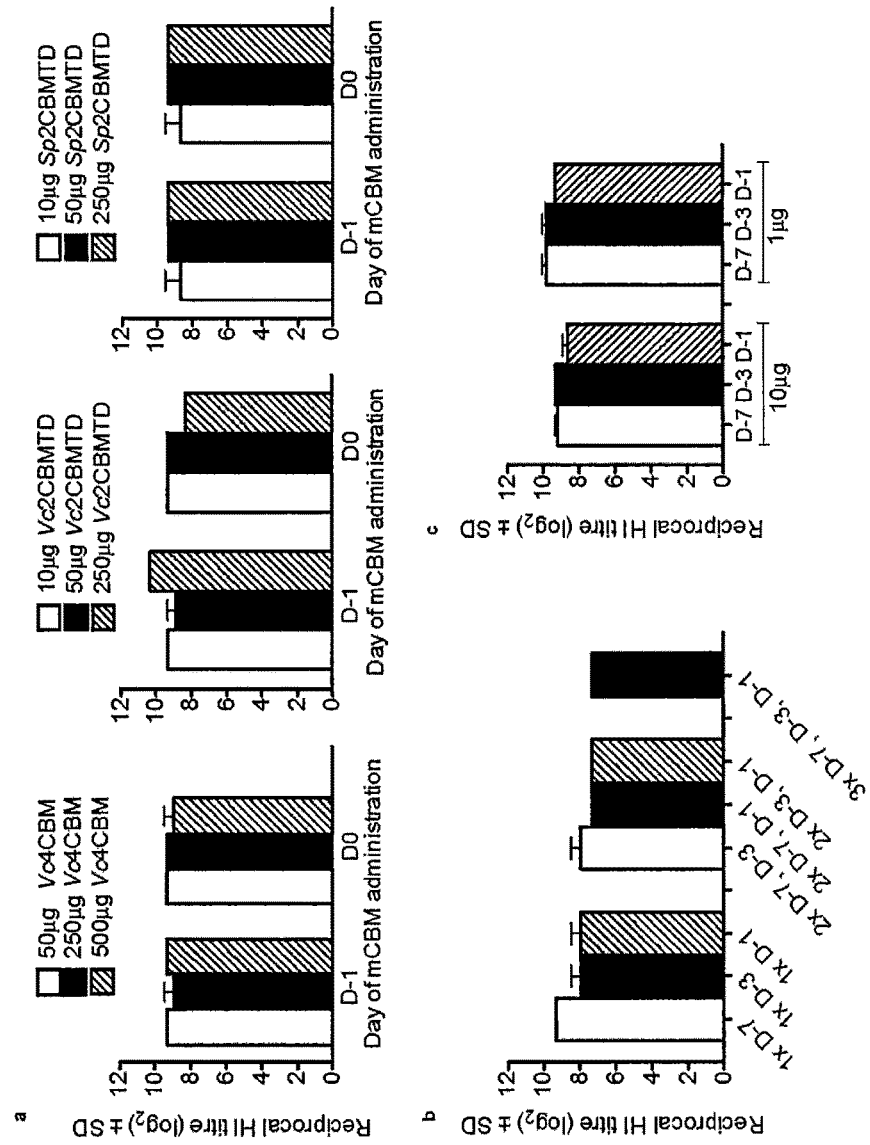

FIG. 8. Serum antibody responses in BALB/c mice inoculated with mouse-adapted A/California/04/2009 (H1N1) influenza virus after administration with Vc4CBM, Vc2CBMTD or Sp2CBMTD. a, Anti-HA titre after single administration of Vc4CBM (50, 250 or 500 µg, left panel), Vc2CBMTD (10, 50 or 250 µg, middle panel) and Sp2CBMTD (10, 50 or 250 µg, right panel) when given on day −1 or day 0. b, anti-HA titre after administration of Sp2CBMTD (50 µg) given once, twice or three times on days −7, −3 or −1. c, anti-HA titre after single administration of Sp2CBMTD (1 or 10 µg) given on days −7, −3 or −1. Bars represent mean reciprocal HI titres ($\log_2$)±s.d. for each treatment group.

Figure 9:
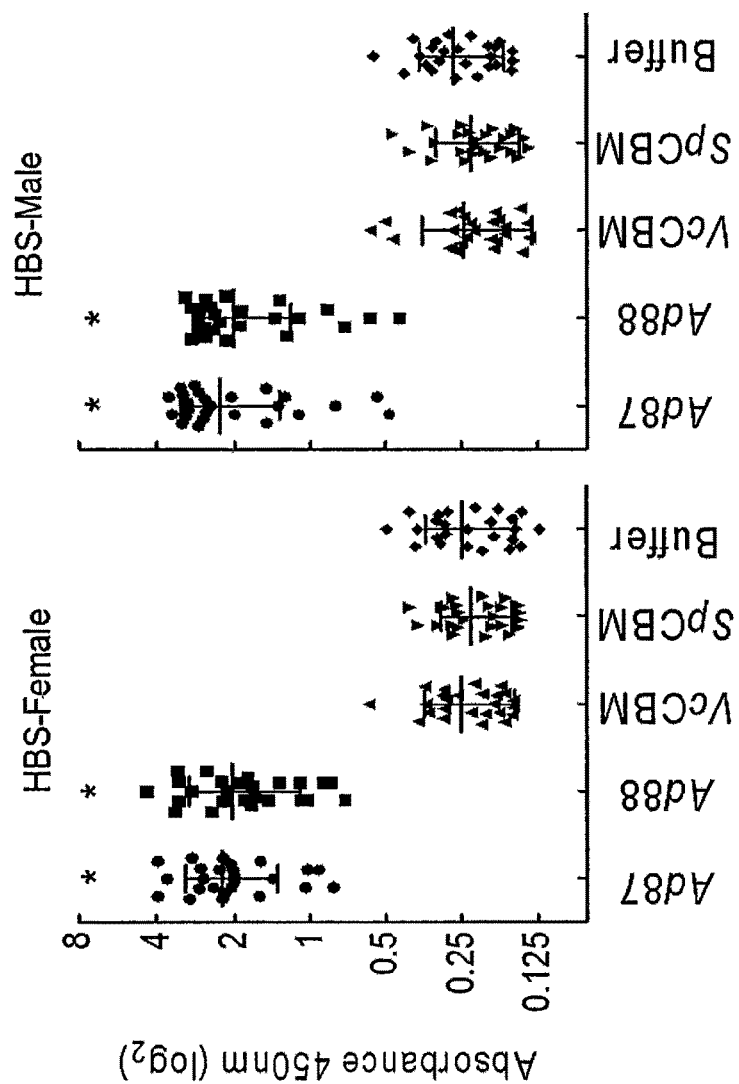

FIG. 9. Demonstration of absence of pre-existing immunity to VcCBM or SpCBM in the human population. Analysis of human blood sera for the presence of anti-CBM antibodies using ELISA. Samples (n=50) were obtained from a mixed aged population of males and females (Seralab, UK). Ad87 and Ad88 are positive controls for adenovirus antibodies. Error bars represent s.d. as measured against buffer block (no serum). *$p<0.001$.

Figure 10:
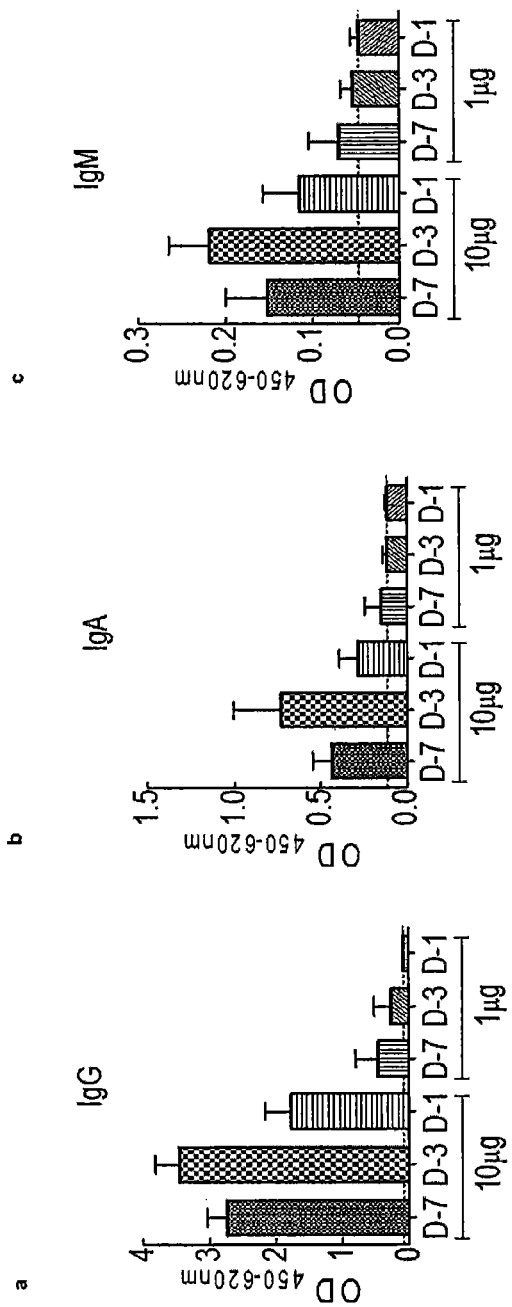

FIG. 10. Detection of sera IgA, IgG and IgM antibodies to Sp2CBMTD following treatment in mice. Mice were intranasally administered 10 or 1 µg (50 µl) of Sp2CBMTD on day −7, −3 or −1 before challenge with mouse-adapted A/California/04/2009 (H1N1) influenza virus on day 0. Sera were taken on day +21 to analyze for anti-Sp2CBMTD antibodies by ELISA, as described in Full Methods. Bars indicate the mean absorbance change±s.d. for IgG (a), IgA (b) and IgM (c) from three mice per group, respectively. Dashed line indicates the limit of detection of assay for IgG ($A_{450-620\ nm}$ 0.074), IgA (0.115) and IgM (0.047), respectively.

Figure 11:
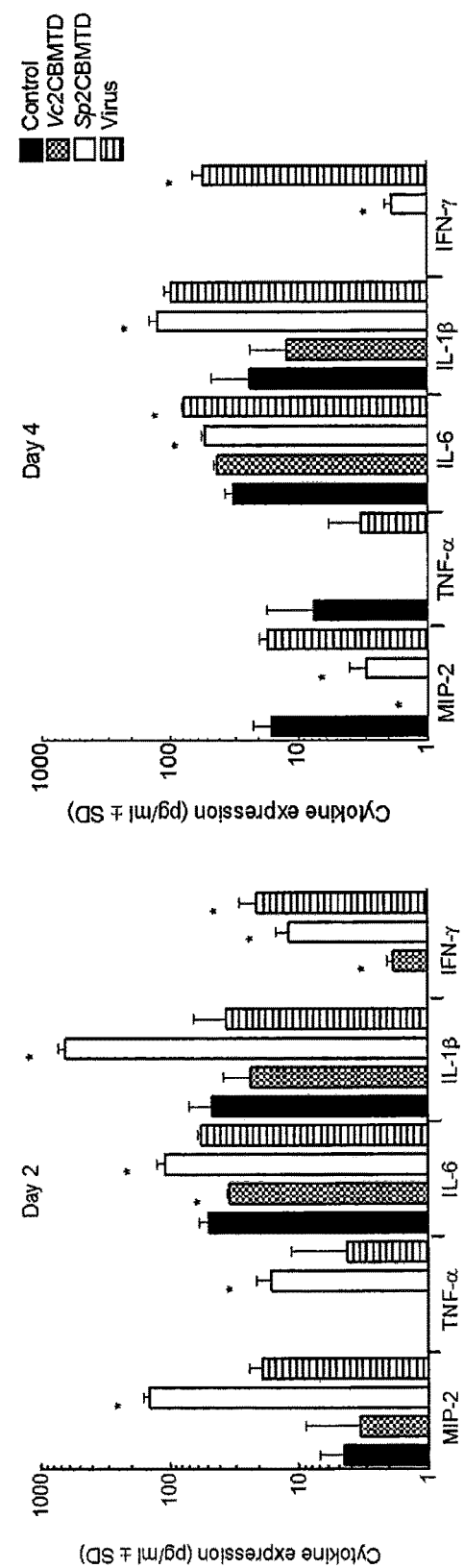

FIG. 11. Effect of mCBMs on pulmonary expression of chemokines and cytokines. Inflammatory mediators MIP-2, TNF-α, IL-6, IL-1β, IFN-γ, GM-CSF and IL-2 were assayed by ELISA using lung homogenates obtained from BALB/c mice on days 2 and 4 after nasal administration of either Vc2CBMTD (100 µg), Sp2CBMTD (100 µg), A/WSN/1933 (H1N1) influenza virus ($5\times10^3$ PFU) or PBS (control). All but GM-CSF and IL-2 were detected in lung homogenates. Bars indicate the mean concentration (pg/ml)±s.d. from 5 mice. *$p<0.05$ compared with the results for the control group (uninfected, untreated).

Figure 12:
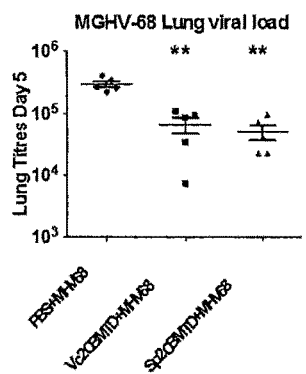
Figure 12:
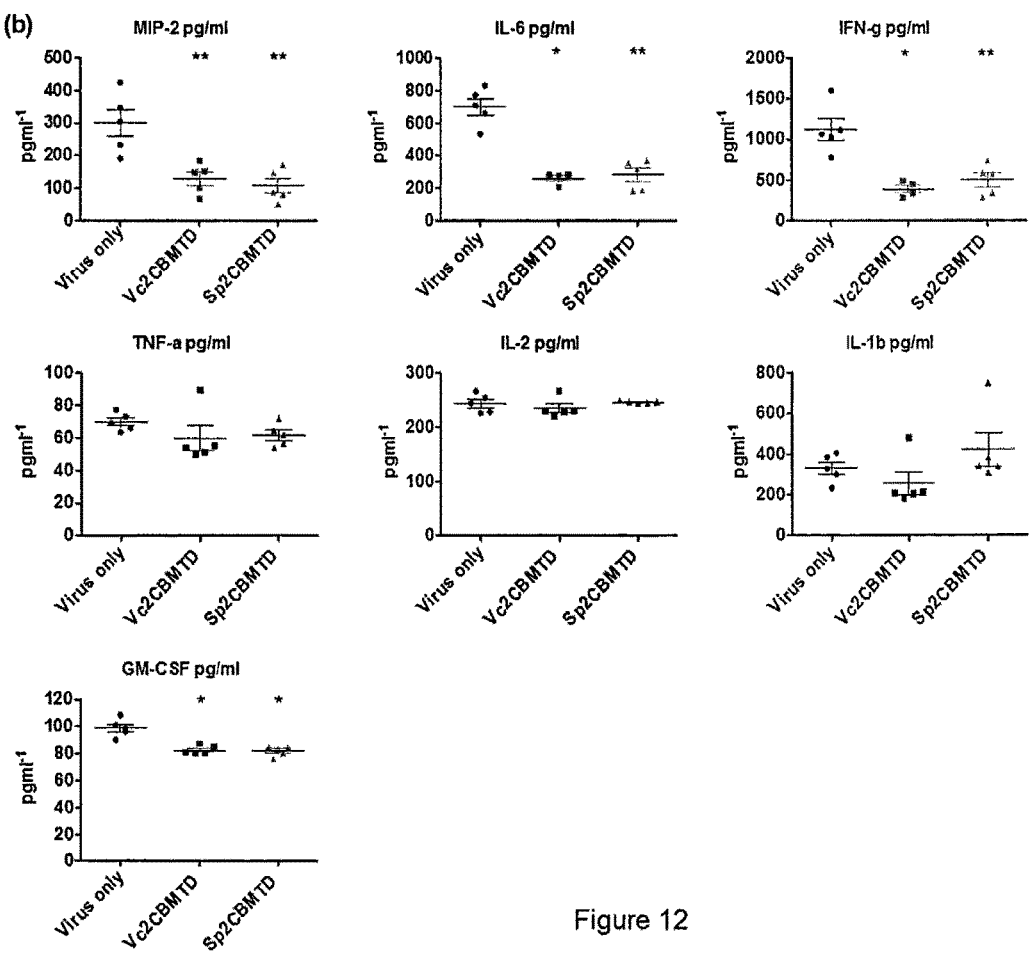

FIG. 12: Effect of hexameric mCBMs in BALB/c mice on lung viral load (a) and cytokine levels (b) when administered as a triple dose (50 µg, Day −7, −3, −1) prior to challenge with murine gammaherpesvirus MHV-68 ($4\times10^5$ PFU) or PBS (control). Bars indicate the mean concentration (pg/ml) ±s.d. from 5 mice. Mann Whitney test *$p<0.05$, **$P<0.01$ FIG. 13: SDS-PAGE to determine Sp2CBMTD protein stability. Gel comprised 10 µl/channel at concentrations 5.25-0.66 µg/channel dissolved in PBS) under reducing conditions in 12% SDS-PAGE (BioRad laboratories, Hercules, Calif.).

FIG. 14: Effect of single administration of Sp2CBMTD (before virus challenge) on survival and weight changes of BALB/c mice lethally challenged with A/Anhui/1/2013 (H7N9) influenza virus.

Figure 15:
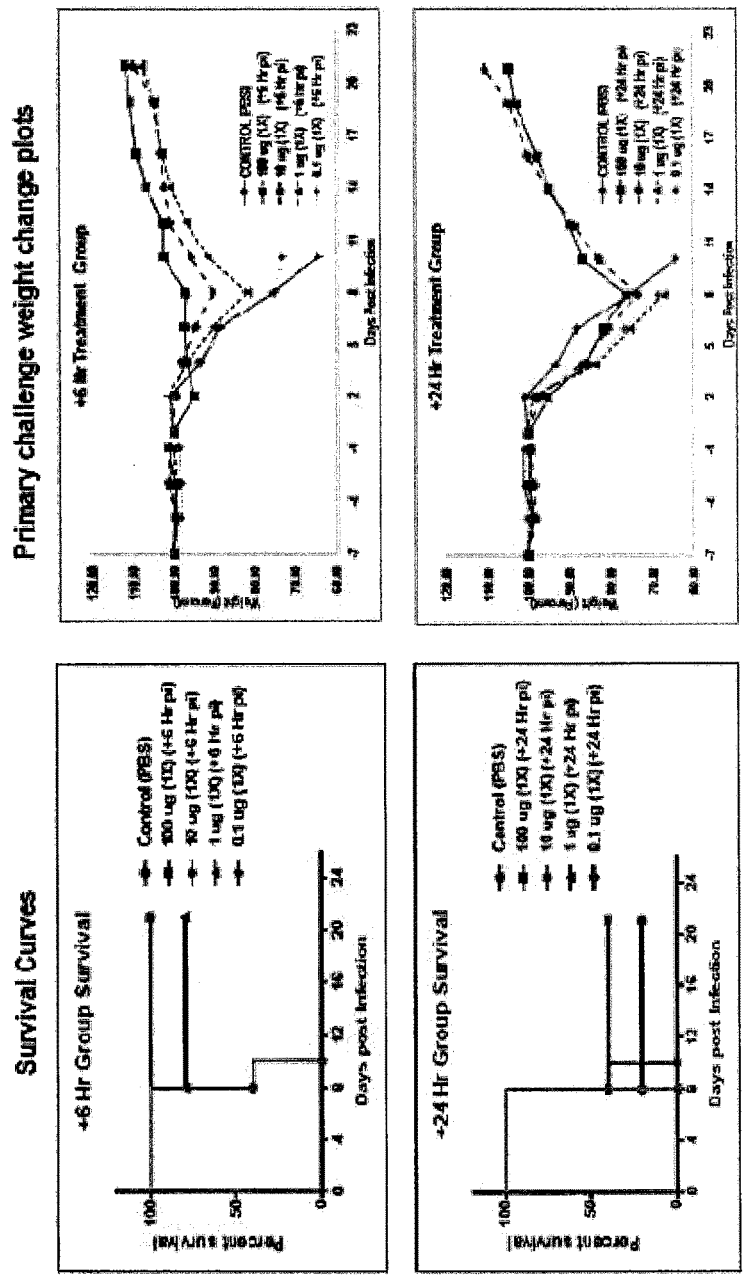

FIG. 15: Effect of single administration of Sp2CBMTD (after virus challenge) on survival and weight changes of BALB/c mice lethally challenged with A/Anhui/1/2013 (H7N9) influenza virus.

Figure 16:
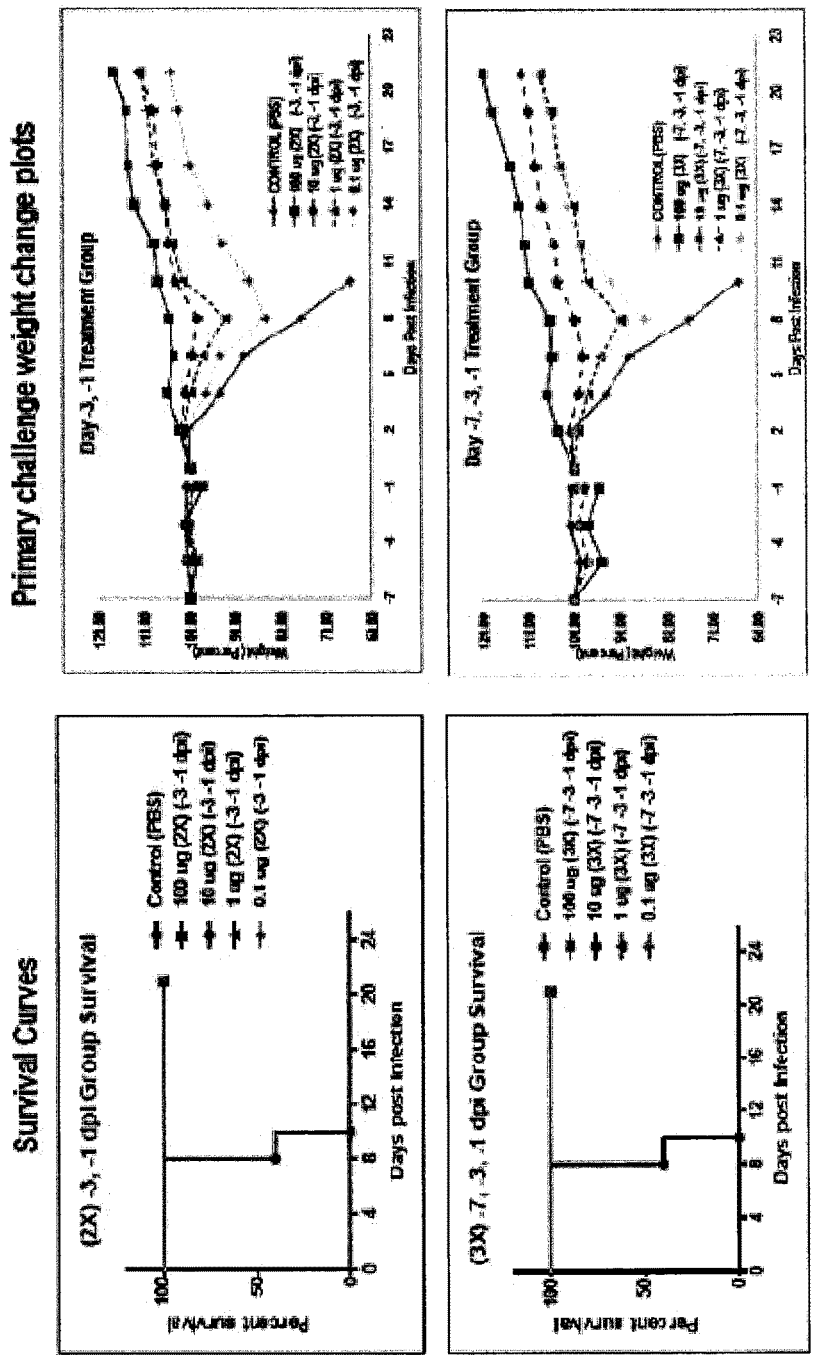

FIG. 16: Effect of repeated administration of Sp2CBMTD (before virus challenge) on survival and weight changes of BALB/c mice lethally challenged with A/Anhui/1/2013 (H7N9) influenza virus.

Figure 17:
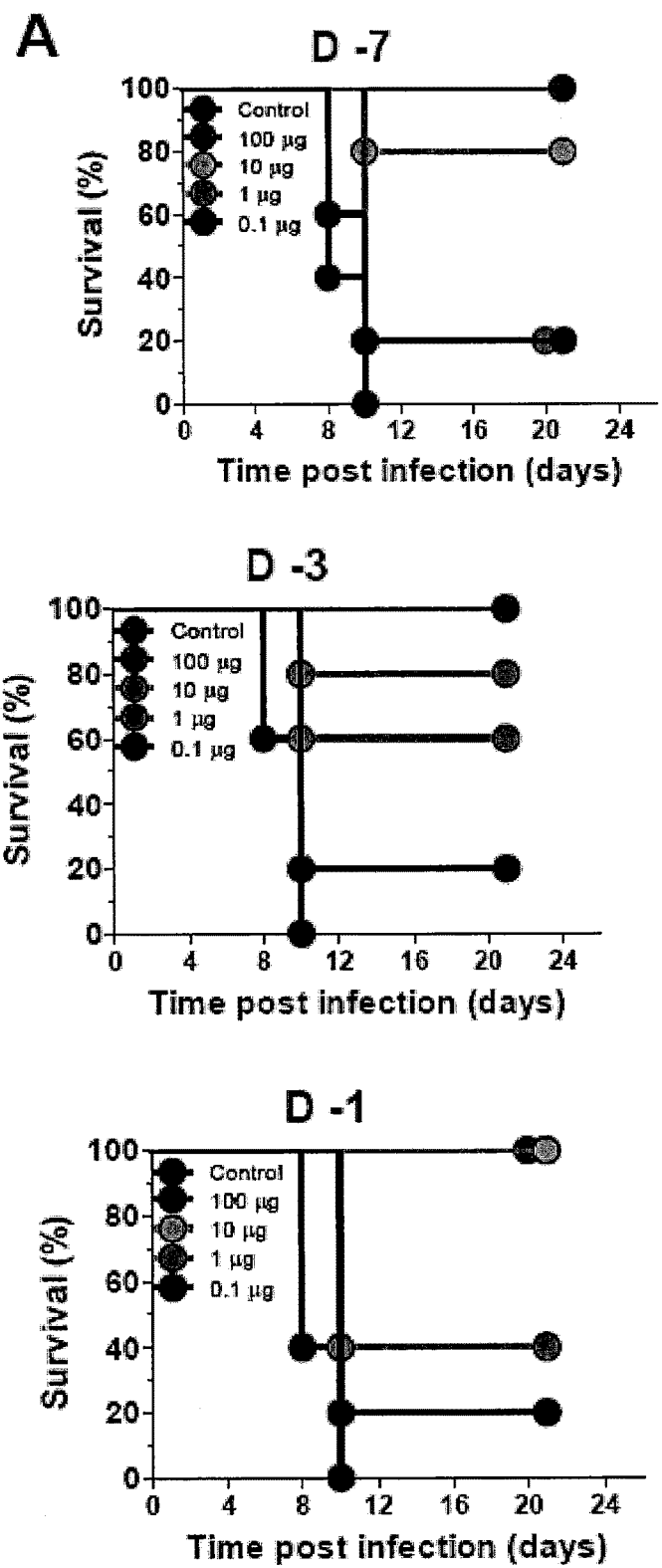
Figure 17:
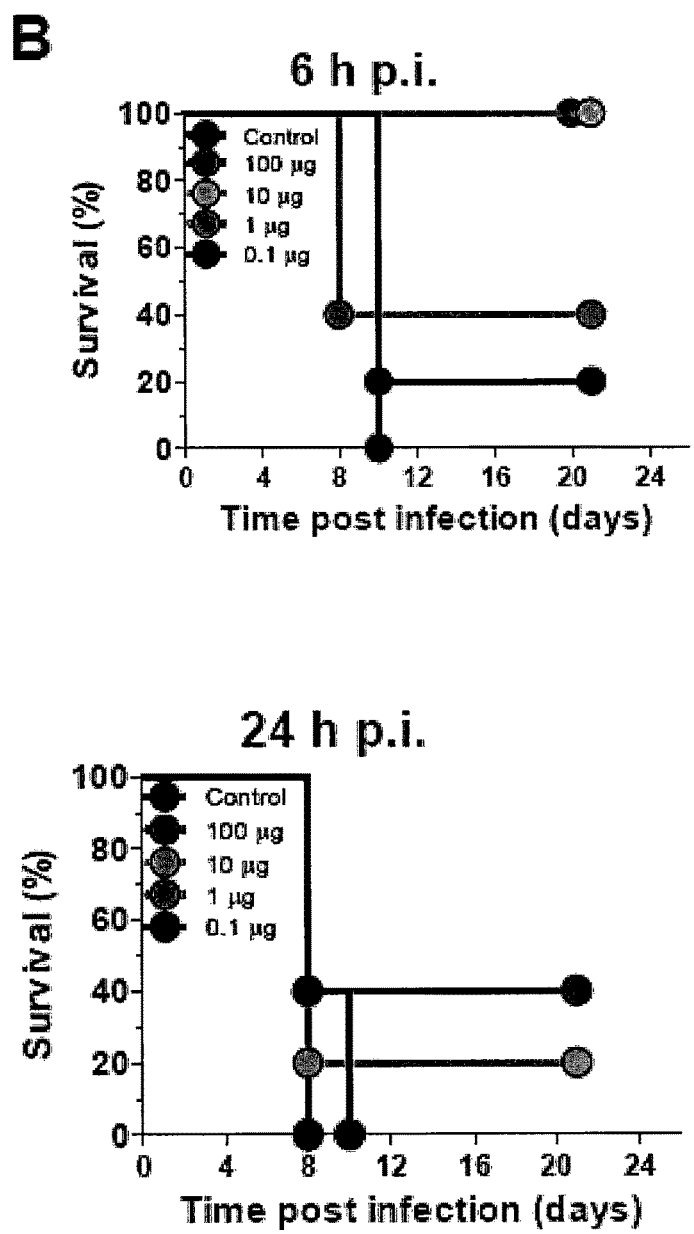
Figure 17:
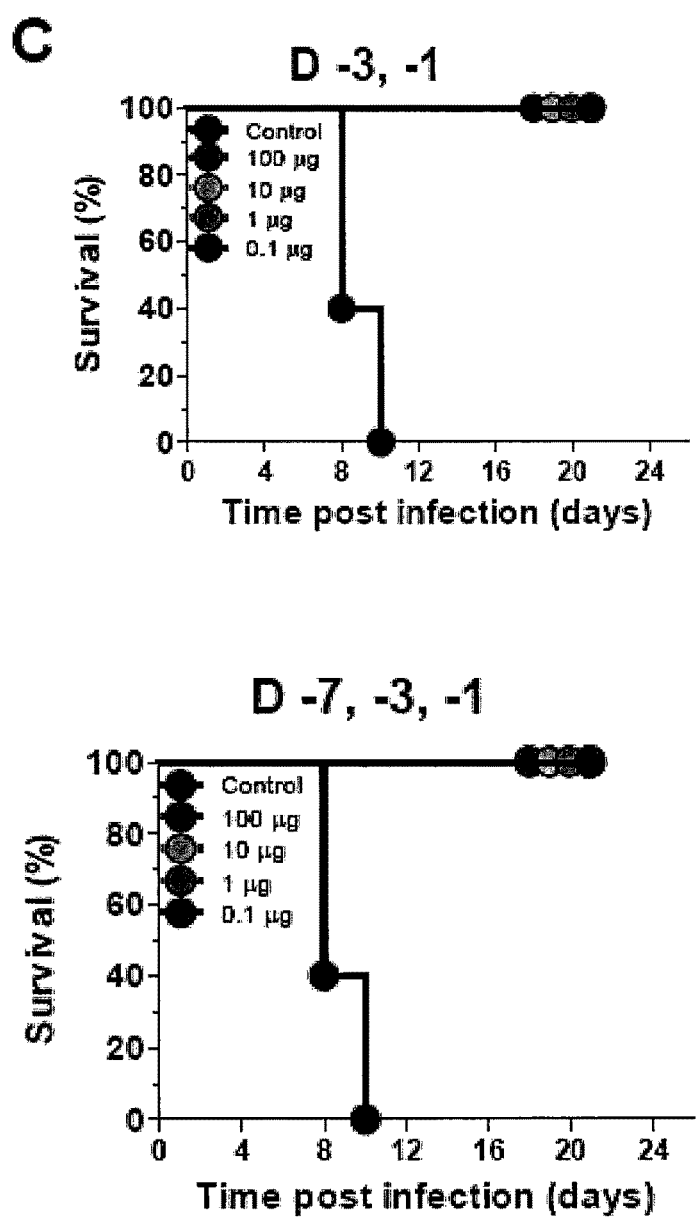

FIG. 17. Effect of single and repeated administration of Sp2CBMTD on survival of mice infected with a lethal dose of A/Anhui/1/2013(H7N9) influenza virus. BALB/c mice (n=5) were lightly anesthetized with isoflurane, and Sp2CBMTD was administered intranasally as a single dose (0.1, 1, 10, or 100 µg/mouse) at 7, 3, or 1 day before (A) or 6 or 24 hours after (B) H7N9 virus inoculation. Double and triple doses of Sp2CBMTD were administered at days 3 and 1 or days 7, 3, and 1 before H7N9 virus inoculation, respectively (C). Mice were inoculated intranasally with 5 MLD50 of A/Anhui/1/2013(H7N9) influenza virus and monitored daily for survival and weight loss. Control untreated animals received sterile PBS on days 7, 3, and 1.

Figure 18:
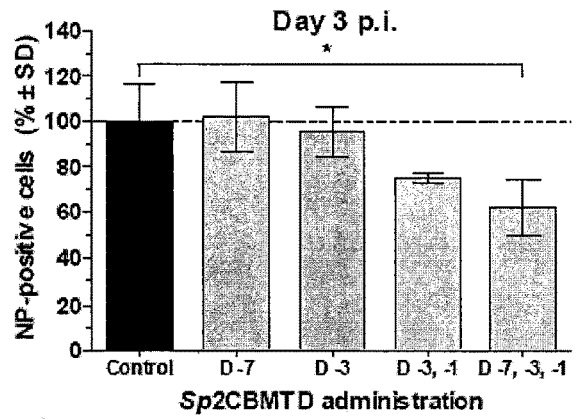
Figure 18:
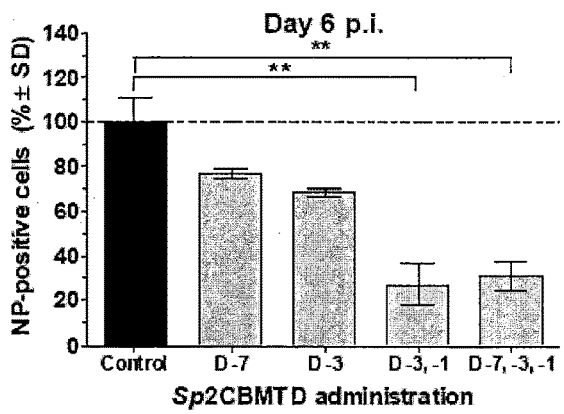
Figure 18:
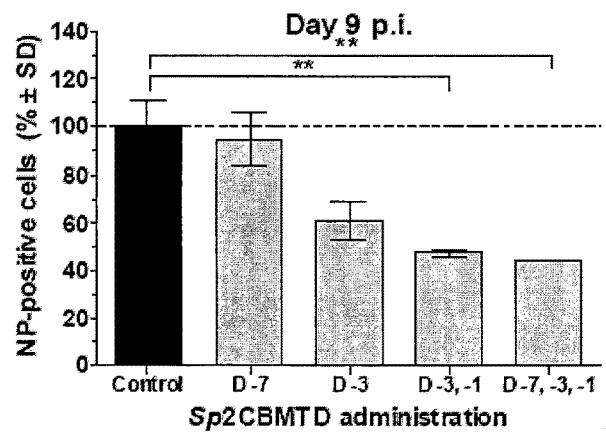
Figure 18:
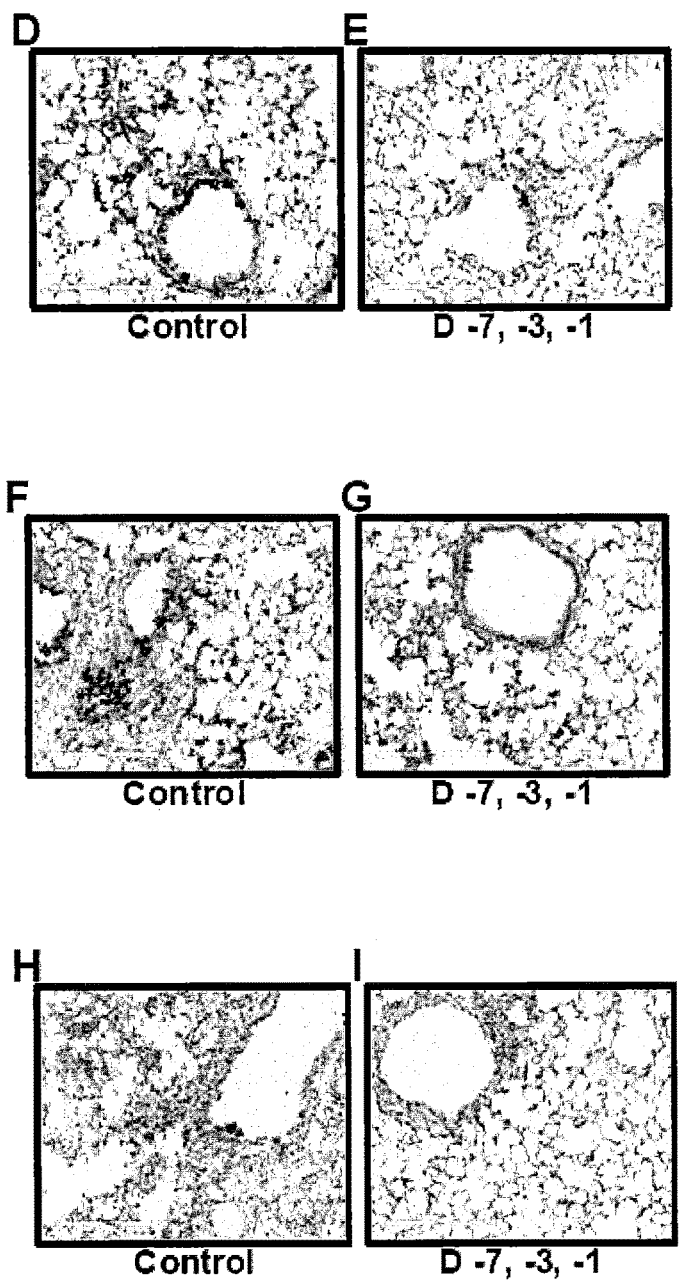

FIG. 18. Effect of Sp2CBMTD on the number of H7N9 influenza virus NP-positive cells in mouse lung sections. BALB/c mice were given Sp2CBMTD (10 µg/mouse) as a single administration on day 7 or 3, or as double (days 3 and 1) or triple (days 7, 3, and 1) administration before H7N9 virus inoculation. Three mice in each experimental group were sacrificed on days 3, 6 and 9 p.i. Mouse lungs were removed, fixed in 10% neutral buffered formalin, and stained for immunohistochemistry with anti-influenza A nucleoprotein (NP) antibody. One slide including all lung lobes per mouse was used for evaluations. Quantitative analysis of the number of NP-positive cells on days 3 (A), 6 (B), and 9 p.i. (C) was done by the Image Scope viewing software. Specifically stained cells have dark brown color in the nucleus and cytoplasm. Images of the lung tissues of control animals (D, F, H) showed H7N9 influenza antigen-positive staining in bronchiolar and respiratory epithelial cells on days 3 and 6 p.i. (D, F) compared with the few antigen-positive cells on day 9 p.i. (H). Images of the representative Sp2CBMTD-treated group (triple administration on days 7, 3, and 1 before H7N9 inoculation) showed marked reduction of antigen-positive cells in the lungs of mice on days 3 and 6 p.i. (E, G) compared with controls, and few positive cells on day 9 p.i. (I). The dashed line indicates H7N9 influenza antigen-positive cells determined in virus infected PBS-treated animals and was considered as 100%.

Magnification, ×20. *P<0.01, **P<0.05 compared with results for the control group at each day p.i. studied; two-way ANOVA.

Figure 19:
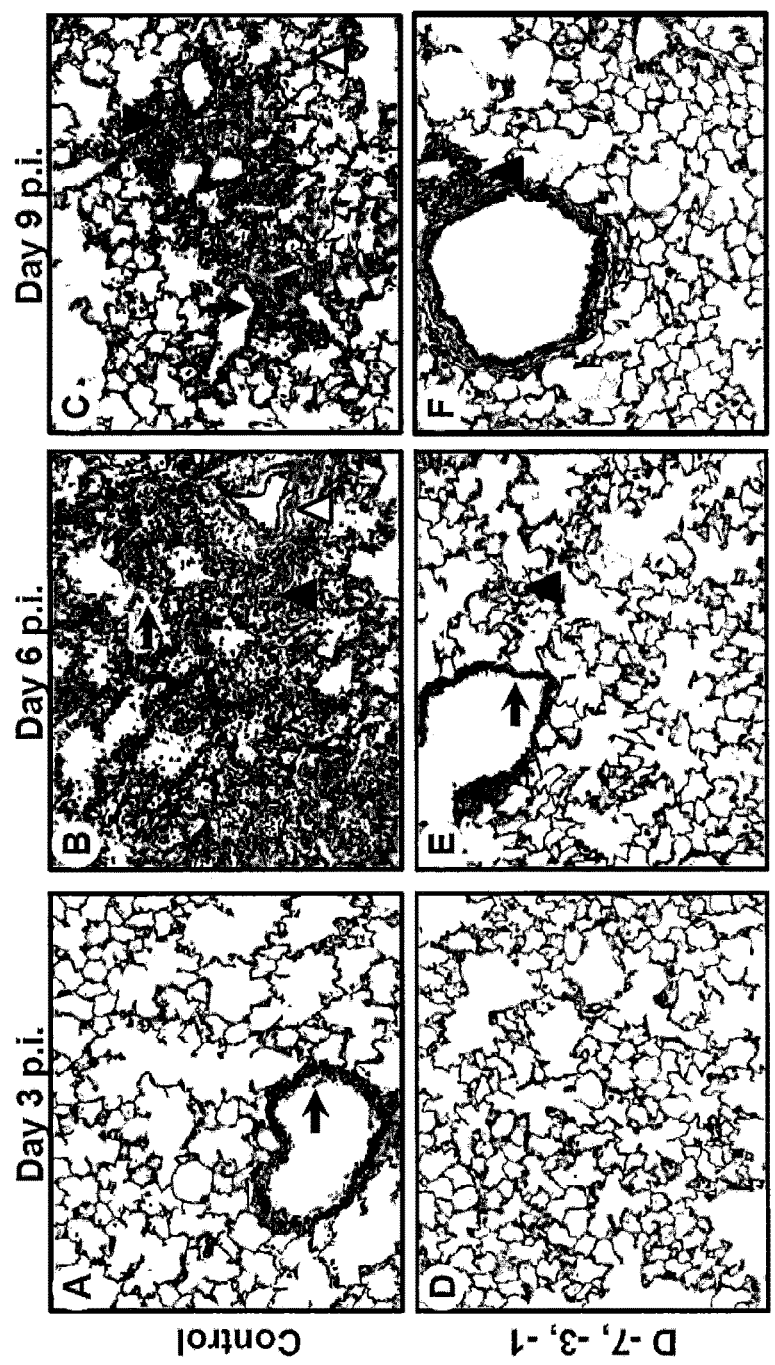

FIG. 19. Histologic changes in the lungs of mice treated with Sp2CBMTD and infected with 5MLD50 of A/Anhui/1/2013(H7N9) influenza virus. Sp2CBMTD was administered as described in the FIG. 18 legend. Mouse lungs were fixed in 10% neutral buffered formalin and stained with hematoxylin and eosin. The lungs of H7N9-infected PBS-treated mice had necrosis of epithelial cells in the bronchi on day 3 p.i. (A) and alveolar collapses and infiltration with inflammatory cells, edema, and viral pneumonia on day 6 p.i. (B). Edema and infiltration with inflammatory cells were observed on day 9 p.i. (C), but lesions were restricted to a few areas. Distinctive pathological changes were not observed in the lungs of mice given 3 doses of Sp2CBMTD on day 3 p.i. (D), and there was minimal epithelial necrosis and infiltration of the alveoli with inflammatory cells on days 6 and 9 p.i. (E, F). Magnification, ×20. Solid arrow indicates epithelial necrosis, open arrow head indicates edema, and solid arrow head indicates peribronchiolar alveoli infiltration with macrophages and neutrophils.

Figure 20:
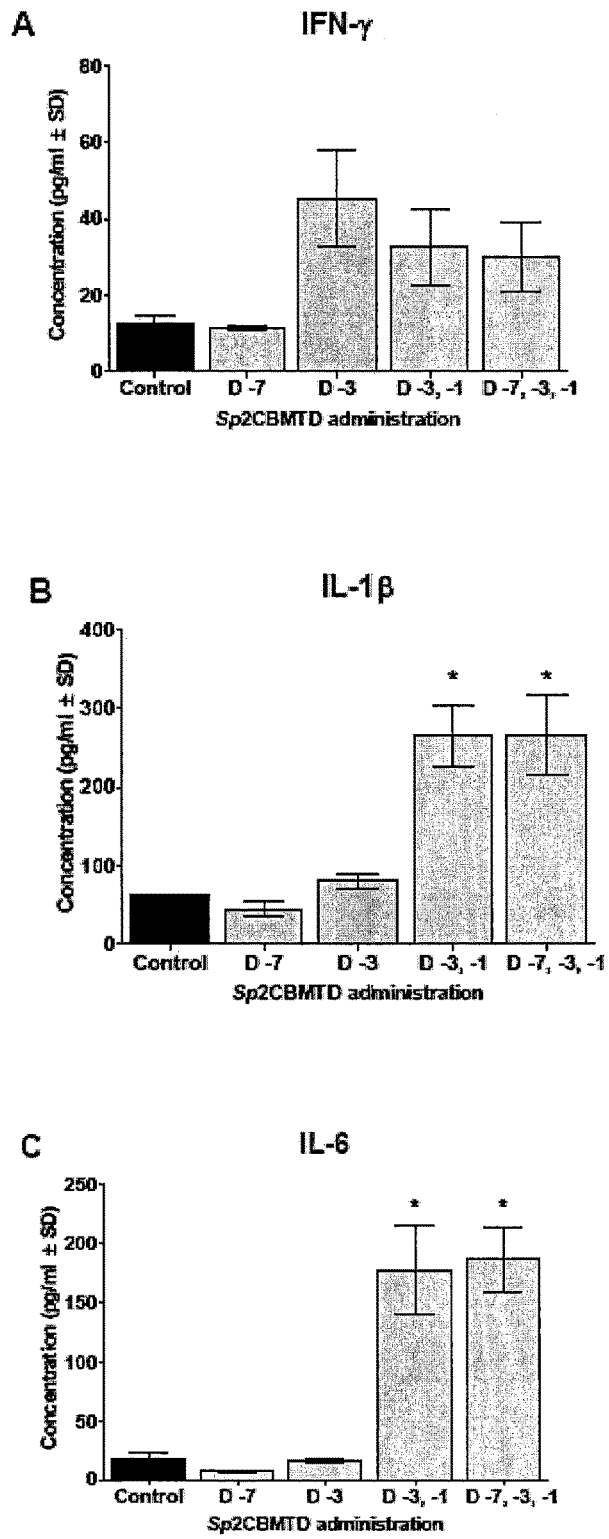
Figure 20:
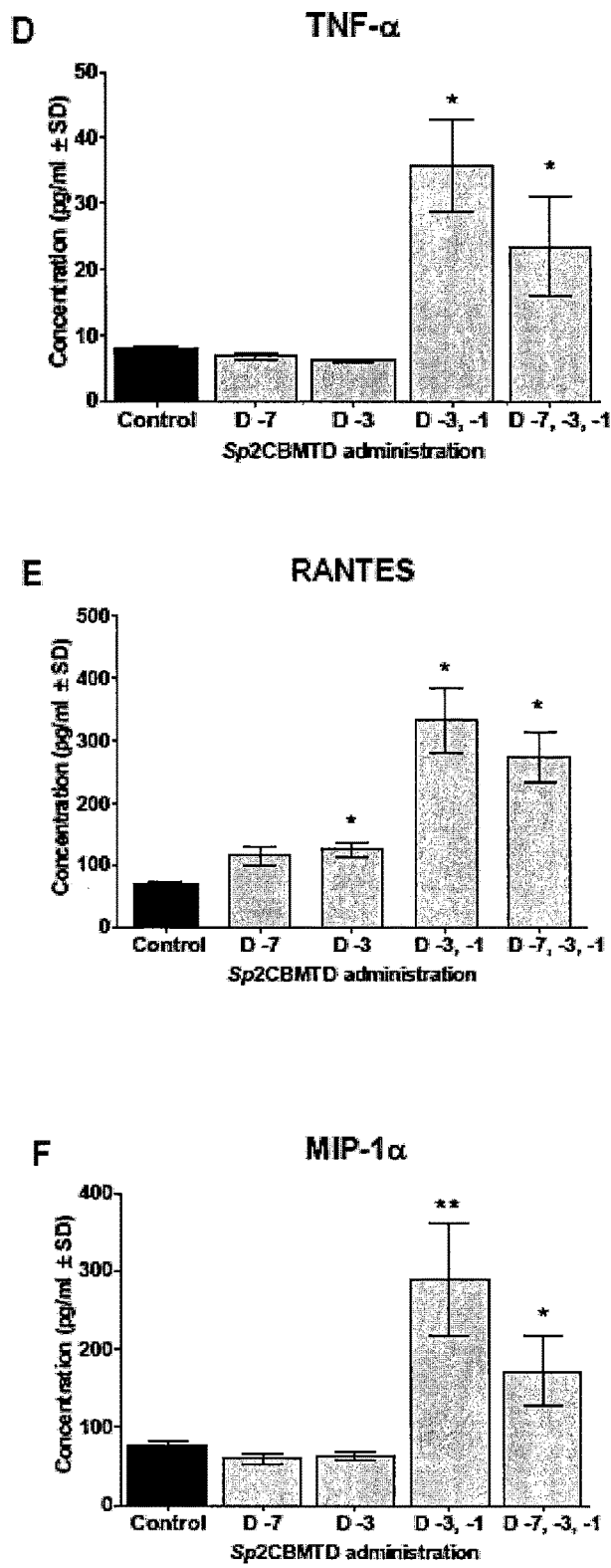
Figure 20:
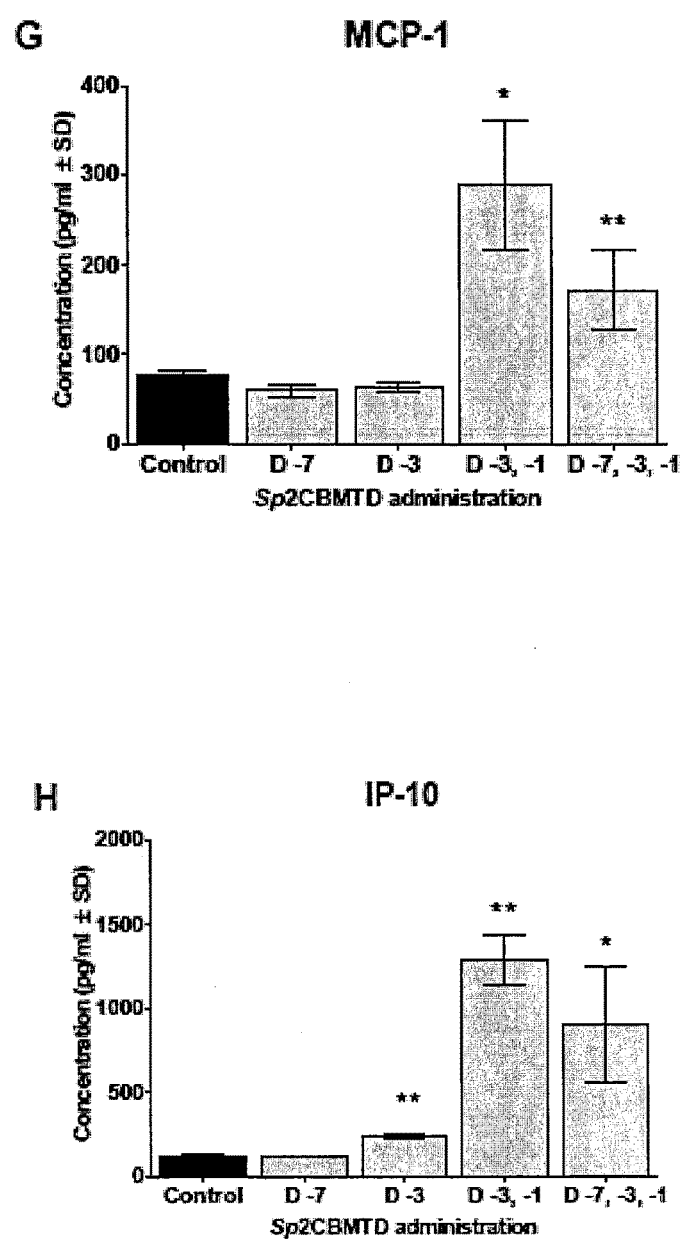

FIG. 20. Effect of Sp2CBMTD administration on pulmonary expression of cytokines and chemokines. Sp2CBMTD was administered as described in the FIG. 18 legend. Concentrations of IFN-γ (A), IL-1R (B), 11-6 (C), TNF-α (D), RANTES (E), MIP-1α (F), MCP-1 (G), and IP-10 (H) was assessed by the MYCTOMAG-70K-PMX MILLIPLEX® premixed kit in lung homogenates of BALB/c mice on day 0 before H7N9 virus infection. Bars indicate the mean concentration (µg/mL)±SD from 3 mice. Black bars represent H7N9 virus-inoculated, PBS treated mice (control). Grey bars represent mice treated with Sp2CBMTD. *P<0.05; **P<0.05, compared with results for the control group, unpaired Student t-test.

Figure 21:
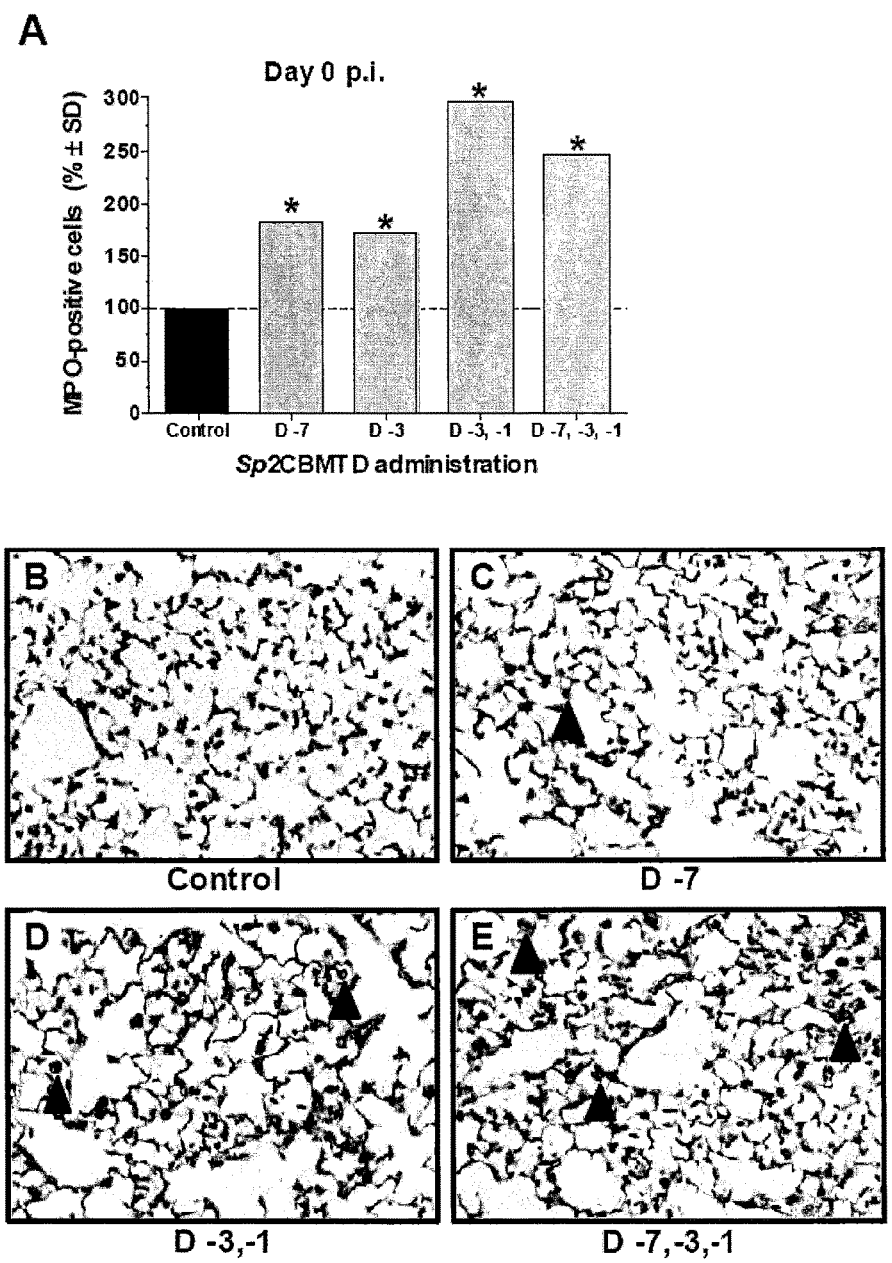

FIG. 21. Infiltration of mouse lung tissues with neutrophils after administration of Sp2CBMTD. Sp2CBMTD was administered as described in the FIG. 18 legend. Mouse lungs were obtained on day 0 p.i., fixed in 10% neutral buffered formalin, and stained with myeloperoxidase (MPO), a specific marker for neutrophils. MPO-stained sections were blinded for pathology evaluation. The presence of antigens was quantified by capturing digital images of whole-lung sections, using an Aperio ScanScope XT Slide Scanner (Aperio Technologies) and then manually outlining entire fields together with areas of noticeably decreased or absent MPO staining. The percentage of lung field with reduced staining coverage was calculated by using the Aperio's ImageScope software and expressed as a relative value over virus-infected PBS-treated (control) animals (A). Representative MPO-stained lung images of control animals (B) and animals given single (C), double (D), or triple (E) dose(s) of Sp2CBMTD before H7N9 virus infection. Magnification, ×20. Solid arrow head indicates neutrophils. *P<0.0001 compared with results for the control group; one-way ANOVA EXAMPLE 1: Prevention of Influenza by Targeting Host Receptors Using Novel Engineered Proteins Methods
Virus.

For in vitro studies, the following influenza viruses were used: A/WSN/1933 (H1N1), A/Puerto Rico/8/1934 (A/PR/8/1934, H1N1), A/Udorn/1972 (H3N2), and B/Hong Kong/1973 were propagated in Madin-Darby canine kidney cells (MDCK, American Type Culture Collection, Manassas, Va.). Virus infectivity in MDCK cells was determined by plaque assay and expressed as $\log_{10}$ PFU/ml. For in vivo studies, two strains were used: mouse-adapted A/WSN/1933 (H1N1) strain propagated in MDCK cells and mouse-adapted A/California/04/2009 (H1N1) virus[30] that was grown in embryonated chicken eggs. To determine the 50% mouse lethal dose ($MLD_{50}$) for A/California/04/2009 (H1N1), four female 6-week-old BALB/c mice (Jackson Laboratories, Bar Harbor, Me.) were lightly anesthetized with isofluorane and intranasally inoculated with 50 µl of 10-fold serial dilutions of virus in PBS. The $MLD_{50}$ value was determined after a 21-day observation period.

Generation of mCBMs.

Tandem-repeat multivalent protein, Vc4CBM, based on the Family 40[31] sialic acid binding domain (CBM) of the nanH gene encoding the sialidase from *V. cholerae*, was generated using PCR-based cloning techniques as described previously[8]. Oligomerisation of the CBM domain from *V. cholerae* nanH sialidase, and from *S. pneumoniae* nanA sialidase, using the trimerisation domain from the pseudaminidase protein from *Pseudomonas aeruginosa* was engineered as follows: the DNA fragments encoding the CBM of *V. cholerae* sialidase residues 25-216, and that of *S. pneumoniae* nanA sialidase residues 121-305, respectively, were modified at the 5' and 3' termini by PCR amplification using primer pairs (Table 3) to incorporate different restriction sites to link one or two copies of the CBM unit in tandem for subsequent ligation to the gene encoding the trimerization domain from *P. aeruginosa* pseudaminidase residues 333-438 (PaTD). The resulting fragments were cloned either into an appropriately digested pEHISTEV vector (for VcCBM fragments) or pEGFP-HISTEV vector (for SpCBM fragments) to create constructs designated as VcCBMTD, Vc2CBMTD, SpCBMTD and Sp2CBMTD, respectively (FIG. 1). GFP-SpCBM was also created using the pEGFP-HISTEV vector for glycan array studies. All constructs were propagated in *E. coli* DH5a cells, and constructs were verified by DNA sequencing, before transforming the expression host *E. coli* BL21 Gold (DE3) for protein production.

mCBM Expression, Purification and Characterisation.

Expression of engineered mCBMs was performed as described previously[8] with some modifications. Briefly, *E. coli* cells containing either His-tagged VcCBMs or GFP-His-tagged SpCBMs were lysed in a buffer containing PBS, 0.3M NaCl and 10 mM imidazole with DNAase (20 µg/ml) and protease (minus EDTA) inhibitor tablets (Roche). Clarified lysates were applied onto a HisTrap HP column, pre-charged with nickel (GE Healthcare) before elution of histidine-tagged CBMs using PBS containing 0.3 M NaCl and 250 mM imidazole. Removal of tag, unless otherwise stated, was performed by digestion in situ with TEV protease overnight before re-applying material to the nickel column. All mCBM proteins were further purified using size exclusion chromatography with a HiPrep 16/60 Sephacryl S200HR column (GE Healthcare) in PBS before using either a Vivapure S Maxi H (VcCBMs) or Q Maxi H (SpCBMs) column (Sartorius) to remove endotoxins. GFP-tagged proteins were also subjected to affinity chromatography and size exclusion chromatography as described above. Protein yield was calculated to be between 15-70 mg/l depending on the mCBM. Proteins remained stable for several months when stored −80° C. Protein purity and size were verified by 12% SDS polyacrylamide gel electrophoresis and mass spectrometry. Purified mCBMs binding to sialic acid was verified by surface plasmon resonance (Biacore T-100, University of Edinburgh) using a streptavidin-coated biosensor chip immobilized with a multivalent, biotinylated α-2,3-sialyl-lactose-PAA (Glycotech) (Table 1).

Glycan Microarray.

The glycan binding specificity of GFP-SpCBM was analyzed using Glycan slide array v4.2 (Consortium for Functional Glycomics). Preparation of GFP-SpCBM (200 μg/ml) for analysis was as described previously[8] but modified to allow the use of an anti-GFP antibody to enhance the fluorescence signal of binding.

Cell Protection Assay.

For cell protection assays, confluent MDCK monolayers (in DMEM, 0.5% FCS) were incubated with mCBMs (10 mg/ml, appropriately diluted in serum-free (SF) DMEM) at 37° C. for 1 h. Monolayers were rinsed with SF-DMEM before inoculation with ~100-200 PFU of influenza virus (A/WSN/1933 (H1N1), A/PR/8/1934 (H1N1), A/Udorn/1972 (H3N2), and B/Hong Kong/1973) for 1 h at 37° C. before washing. Cells were overlayed with 1.2% (w/v) Avicel (FMC Biopolymer) in 10 mM HEPES (pH 7.4) in DMEM supplemented with 2 μg/ml N-acetylated trypsin. Plates were incubated at 37° C. for 2-3 days. Plaques were visualised by fixing monolayers in 4% formaldehyde and staining with 0.1% crystal violet. The $EC_{50}$ values of mCBMs that protect 50% of cells from virus were calculated for each mCBM from dose-response curves.

Viral Replication Inhibition Assay.

Confluent MDCK cells (96-well format) were used to assess inhibition of influenza A virus replication by mCBMs. Cells were incubated with different mCBMs for 1 h at 37° C., before washing and adding influenza A virus (A/WSN/1933 (H1N1), A/PR/8/1934 (H1N1), A/Udorn/1972 (H3N2), MOI 0.01 PFU/cell) to monolayers for 1 h. The virus inoculum was removed and SF DMEM containing N-acetylated trypsin (2.5 μg/ml) was added to cells and incubated for a further 16-24 h. Cells were fixed with 4% formaldehyde, permeabilized with PBS containing 0.5% Triton-X100 and 20 mM glycine (PBS-T) for 30 mins prior to blocking with PBS containing 1% BSA, 0.02% sodium azide (BB), for 2-3 h. Cells were rinsed before addition of goat anti-influenza A (1:500 dilution in BB, Santa Cruz) for 1-2 h at 22° C. Plates were washed before addition of donkey anti-goat IgG HRP conjugate antibody (1:500 dilution, Santa Cruz). For colour development, plates were incubated with TMB (HRP substrate, Sigma). The reaction was stopped by addition of 1M HCl. Absorbance was measured at 450 nm wavelength (620 nm as reference). $EC_{50}$ values were calculated from dose-response curves to determine concentration of mCBM that inhibited 50% of viral replication compared to control wells (untreated, infected).

Cytotoxicity Assay.

The influence of mCBMs on the viability of mammalian epithelial cells (MDCK) during a 24 h period was evaluated using the PrestoBlue cell viability assay as described by the manufacturer (Life Technologies, Invitrogen). mCBMs (dilution of 5 mg/ml stock concentration) were added to confluent cell monolayers and incubated for 24 h at 37° C., alongside controls (DMEM only, untreated control, and 20% (w/v) sodium azide as positive control). PrestoBlue reagent was added to cells and incubated for 1 h before measuring absorbance at 570 nm wavelength (620 nm as reference). The relative absorbance of treated cells was expressed as a percentage of untreated cells plotted against mCBM concentration. The concentration of mCBM required to reduce cell viability by 50% ($CC_{50}$) was determined from dose-response curves using non-linear regression curve fit with a variable slope.

Imaging Studies.

MDCK and human lung carcinoma (A549) cells were diluted to $3 \times 10^5$ cells/ml in DMEM supplemented with 10% FCS before adding 100 μl to each well of a 96-well black flat bottom plate (Costar) and 1.5 ml added to WillCo-dishes (35×10 mm glass bottomed, WillCo Wells B.V.). Cells were incubated overnight to 90-100% confluence. Cells were rinsed three times with warmed sterile PBS and the catalytic domain (residues 319-822) of the *S. pneumoniae* NanA sialidase[32] was added to cells at a concentration of 150 μg/ml in SF-DMEM and left to incubate for 1 h at 37° C., 5% $CO_2$ Cells were extensively rinsed with PBS prior to addition of mCBM (Vc2CBMTD 0.05 mg/ml or Sp2CBMTD 0.1 mg/ml in SF-DMEM) and further incubated for 1 h at 37° C., 5% $CO_2$. Cells were rinsed before rabbit polyclonal anti-mCBM antibody (Eurogentec, Belgium) was added (1:1000 in DMEM-3% FCS) and incubated for 1 h at 37° C., 5% $CO_2$. This was followed by the addition of goat anti rabbit Alexa Fluor 488 IgG (Life Technologies) at 2 μg/ml in DMEM-3% FCS and incubated for a further 1 h at 37° C., 5% $CO_2$. DAPI was then added for 30 min before a final wash of cells with PBS. Plates were read on TECAN Infinite Pro Fluorescence plate reader (using excitation and emission wavelengths of 488 nm and 518 nm). Live cells were imaged using a DeltaVision deconvolution microscope (Applied Precision) using excitation and emission wavelengths of 485 nm and 531 nm, respectively.

Mice Infection Studies.

In vivo studies were conducted in The Roslin Institute, Edinburgh, UK and St Jude Children's Hospital, Memphis, Tenn., USA. Female BALB/c mice were purchased either from Harlan UK Ltd (5-6 weeks old) or from Jackson Laboratories (6-8 weeks old), Bar Harbor, Me., USA. In UK, studies were conducted at the animal testing facility for influenza research at the Centre for Infectious Diseases, Edinburgh, and carried out under a UK Home Office License according to the Animals (Scientific Procedures) Act 1986. Mice were anaesthetized using halothane (Rhone Merieux Ltd, Harlow, Essex, UK) before intranasally administering varying amounts of mCBM (100-500 μg in PBS) either 24 h before or on the day of lethal viral challenge with either $5 \times 10^3$ or $4 \times 10^4$ PFU of influenza A/WSN/33 (H1N1) virus in 40 μl PBS. Mice were weighed daily and assessed for visual signs of clinical disease. Animals that had lost 25% of their original body weight were euthanized by $CO_2$ asphyxiation. On days 4 and 7 p.i., unless otherwise indicated, lungs were removed, homogenized in PBS and clarified by centrifugation. Infectious virus titres were determined by standard plaque assays on MDCK cells.

Experiments with mouse-adapted A/California/04/2009 (H1N1) influenza virus were conducted in animal biosafety level 2+ (ABSL 2+) containment approved for use by the U.S. Department of Agriculture. All studies were conducted under applicable laws and guidelines and after approval from the St. Jude Children's Research Hospital animal care and use committee. Groups of BALB/c mice (n=5) were given 50 μl of mCBMs intranasally with either a single, double or triple dose of between 0.1 to 500 μg/mouse unless specified otherwise. Treatment with mCBMs protein was initiated at different time points between day-7 to day+1 of viral challenge. Animals were inoculated with A/California/04/2009 (H1N1) influenza virus at a dose of 10 $MLD_{50}$ per mouse. Control (infected, untreated) mice received 50 μl of sterile PBS intranasally 1 h before virus inoculation. mCBM toxicity controls (uninfected, treated) were also tested. Mice were observed daily for 21 days p.i. for clinical signs of infection and survival with weight recorded throughout infection period. Virus lung titres were determined on days 3, 6 and 9 p.i. in additional groups of mice (n=3) by a tissue culture infectious dose assay ($TCID_{50}$) in MDCK cells.

Cytokine Analysis.

Cytokine analyses of clarified mouse lung homogenates were performed using Quantikine ELISA kits according to manufacturer's instructions (RD Biosystems, UK).

Antibody Analysis.

Immune sera collected from survived mice 21 days p.i. were tested for both anti-viral HA antibodies and for the presence of anti-mCBM antibodies. HI assays were performed with 0.5% packed chicken red blood cells on sera that were pre-treated with receptor-destroying enzyme (RDE II, 1:10 dilution; Denka Seiken Co., Japan) and heat-inactivated at 56° C. for 30 min. A standard ELISA was employed to measure anti-CBM antibodies from infected mouse sera samples using prepared antigens (1 μg/well) immobilized on 96-well plates (Corning). Sera (diluted 1:1000 in BB) were added to wells followed by goat anti-mouse IgG, IgA or IgM HRP-conjugate antibodies (1:2500 dilution), and presence of antibodies were detected using TMB as described above. To test for pre-existing immunity of sialic acid binding CBMs in the human population, human sera samples (n=50) obtained from a mixed aged population of males and females (Seralab, UK) were used. Sera were diluted 1:1000, before applying a standard ELISA to test for anti-VcCBM and anti-SpCBM antibodies using goat anti-human IgG-conjugated HRP (1:2500).

Statistical Analysis.

For survival studies, the Kaplan-Meier method was used to estimate the probability of survival of untreated and treatment groups. Data plotted with error bars are expressed as means±s.d. unless otherwise indicated. Statistical significance ($p<0.05$) between two groups was determined using the nonparametric Mann Whitney U test. GraphPad Prism 5.0 package (GraphPad Software Inc., La Jolla, Calif.) was used for all analysis.

Summary, Results & Discussion

The influenza virus binds to sialic acid receptors present on the respiratory tract epithelium via its surface haemagglutinin (HA) glycoprotein, an event that triggers viral endocytosis[12]. Human influenza viruses such as the 2009 pandemic H1N1 virus recognize α-2,6-linked sialic acid receptors present in the upper respiratory tract, whereas avian influenza viruses such as H5N1 predominantly recognize α-2,3-linked sialic acid receptors, although such receptors are also present in the human lower respiratory tract[13,14]. The recently emerged human H7N9 virus is unusual in recognizing both types of receptors and therefore has the possibility of sustained human-to-human transmission and pandemic potential[15,16]. We hypothesized that masking such receptors in the respiratory tract with specific proteins could provide a novel therapeutic route to prevent infection. Numerous sialic acid binding proteins are known, but most have low affinity for sialic acid, such as the HA monomer that has ~2.5 mM affinity for its receptor, but gains affinity through being a trimer and by being present in high copy number on the virus surface[17]. Mimicking nature, we engineered multivalent forms using either the sialic acid binding domain from *Vibrio cholerae* NanH sialidase[18] (VcCBM, FIG. 1*a*) or the homologous domain from *Streptococcus pneumoniae* NanA sialidase (SpCBM, FIG. 1*b*). Multivalency was achieved either through tandem repeats[8] or by fusing one or two tandemly-linked CBM domains to an oligomerisation domain (TD) derived from *Pseudomonas aeruginosa* sialidase[19] (FIG. 1*c*), a domain that self-associates to form a trimer. The multivalent forms of VcCBM and SpCBM gain affinity through avidity with dissociation constants <1 nM as measured by surface plasmon resonance (SPR) (FIG. 1*d*, Table 1). Glycan array screening shows that VcCBM[8] and SpCBM (FIG. 5) recognize sialic acids linked α-2,3 or α-2,6, and crystallographic analysis reveals that both domains recognize only the terminal sialic acid in studies using sialyllactose[18].

The ability of the multivalent CBMs (mCBMs) to block virus infection was first tested in vitro (Table 2). Cell protection and virus replication inhibition assays using Madin-Darby canine kidney (MDCK) cells and three different influenza A viruses [A/WSN/1933 (H1N1), A/PR/8/1934 (H1N1), A/Udorn/1972 (H3N2)] and an influenza B virus (B/Hong Kong/1973) showed that the mCBMs blocked viral attachment with $EC_{50}$ values ranging from 0.39 μM to 4.1 μM for mCBMs with valencies between 3 and 6, compared to ~300 μM when using the monovalent counterpart (data not shown). The mCBMs inhibited viral replication and showed no cytotoxicity at maximum feasible concentrations (Table 2). Fluorescence-imaging of mCBMs show that they bind at the cell surface and that binding was largely abrogated after cells were pre-treated with a promiscuous sialidase to remove sialic acids (FIG. 6). Next, we explored the ability of Vc4CBM to block a lethal infection of A/WSN/33 (H1N1) virus in BALB/c mice. Vc4CBM (500 μg) was administered intranasally as a single dose immediately prior to viral challenge. The Vc4CBM-treated mice survived and regained weight after a small initial weight loss with a two-logarithm reduction in lung virus titres 7 days p.i. compared to untreated mice (FIG. 2*a,b*). This initial promising result led us to explore the protective effects of the trimeric (VcCBMTD, SpCBMTD, 400 μg) and hexameric (Vc2CBMTD, Sp2CBMTD, 100 μg) forms given intranasally one day before a lethal challenge with A/WSN/33 (H1N1) virus (FIG. 2*c,d*). Of the four mCBMs, the hexameric forms showed almost no detectable virus in lungs 7 days p.i., with Sp2CBMTD-treated mice demonstrating negligible weight loss (FIG. 2*c*).

We subsequently evaluated the biologics in BALB/c mice against a lethal challenge with mouse-adapted A/California/04/2009 (H1N1) pandemic influenza virus, exploring single intranasal doses (either 10, 50, 250 or 500 μg) of Vc4CBM, Vc2CBMTD or Sp2CBMTD given on day −1, 0 or +1; day 0 being the day of viral challenge, with survival studies continuing to day +21. None of the mCBMs protected mice when given 24 h after viral challenge (FIG. 7). When administered on day −1, Vc4CBM (500 μg) gave only 40% survival. When administered on day 0, Vc4CBM (500 μg) gave 100% survival, in line with the A/WSN/33 (H1N1) virus challenge, but gave only 40% survival at lower doses. In contrast, the hexameric forms gave improved protection when given on day −1 or day 0. Vc2CBMTD gave 80% survival at the lower doses of 10 or 50 μg. Sp2CBMTD provided the best protection, with all mice surviving at all doses administered on day −1, and all mice surviving after administration on day 0 at the 50 or 250 μg dose, with 60% surviving at the 10 μg dose. All animals that survived virus challenge lost weight, but the most beneficial results were achieved when Sp2CBMTD was administrated at a 250 μg dose on day 0 (FIG. 3*b*). We next explored the effect of repeat dosing with Sp2CBMTD administered further in advance of infection. Single 50 μg doses of Sp2CBMTD were administered intranasally to BALB/c mice once, twice or three times up to one week prior to a lethal challenge with A/California/04/2009 (H1N1) virus on day 0. There was 100% survival for all dosing regimens (data not shown), and strikingly there was little or no weight loss when two or three doses were administered (FIG. 4a). The lowest effective dose of Sp2CBMTD was then explored. Single 10, 1 or 0.1 μg doses of Sp2CBMTD were administered on day −7, −3 or −1 in advance of a lethal challenge with A/California/04/2009 (H1N1) virus on day 0. All mice survived the 10 and 1 μg dosing regimens, and significantly, even a single 1 μg dose given on day −7 gave only a maximum 8% weight loss on day 8 p.i., which was soon restored (FIG. 4b), with mice continuing to thrive with no adverse clinical signs to day +21. In contrast, at 0.1 μg dosing, 80%, 20% or 0% of mice survived when administered on day −1, −3 or −7, respectively (FIG. 4b). Viral lung titres measured on days 3, 6 and 9 p.i. showed that for 50 and 10 μg doses, virus had cleared from the lungs by day 9 whereas for 1 and 0.1 μg doses virus titres were similar to control (infected, untreated) mice (results not shown). Significantly, high titres of serum anti-HA antibodies are present following treatment using all dosing regimens showing that there is sufficient viral replication to elicit an immune response (FIG. 8).

One concern with using pathogen-derived biologics is the potential of immunogenicity that may reduce the effectiveness of repeat administration. SpCBM and VcCBM were chosen from human pathogens that may have evolved immunotolerance with the host, and we found no pre-existing immunity to either of the single CBM domains in the human population (FIG. 9). Intranasal administration of the Sp2CBMTD in mice does, however, elicit serum IgG, IgM and IgA antibodies, but in a dose dependent manner, with the 1 μg Sp2CBMTD dose eliciting negligible levels of serum IgA and IgM (FIG. 10). Immunogenicity of the mCBMs may be an issue with repeat usage, however modifications to make the proteins less immunogenic could be employed if necessary[20].

Sialic acids are widely expressed on the surface of all cells in all vertebrates, and are involved in regulating multiple cellular functions, including development of immunity[21]. Intrinsic and extrinsic sialic acid-recognizing proteins, often themselves multivalent, are known to mediate and modulate cellular interactions[22]. The original hypothesis in the biologic design was the masking of sialic acid receptors, however the remarkable protective ability of a single low dose of Sp2CBMTD given 7 days in advance of infection raises the possibility that the biologic may additionally be priming the immune system into an antiviral state. Accordingly, we explored the induction of a limited set of inflammatory cytokines/chemokines by intranasal administration of Vc2CBMTD or Sp2CBMTD in mice and found that there is a significant difference between the two biologics, with Sp2CBMTD stimulating higher levels of IL-1 p, MIP-2 (mouse homologue of IL-8), IFN-γ and TNF-α compared to Vc2CBMTD or PBS (FIG. 11). The *S. pneumoniae* CBM forms part of a larger region of the NanA sialidase that has previously been reported to stimulate certain cytokines in human and mouse brain cells[23], although other segments of NanA may be responsible for this activity. It is possible that our biologics are modulating cellular processes, including cytokine induction, which may be contributing to the protective ability of Sp2CBMTD, the discovery of which will require further extensive exploration.

There is an urgent need for new therapeutic approaches to control influenza. Significant effort is going into developing new vaccine approaches to influenza[24,25], new inhibitors of viral targets[26] and novel strategies targeted at host factors[27,28]. We have demonstrated that biologics targeted to the mammalian host have certain advantages that merit further exploration. Our biologics have the capacity to bind to and mask different sialic acid receptors found in the upper and lower respiratory tract and may, therefore, protect throughout the human airway if a suitable delivery system is employed. The generation of serum anti-HA antibodies observed in all treated mice suggests that as well as affording protection, the biologics allow 'vaccination' to occur upon exposure to virus, potentially providing protection against future exposure. There are many challenges ahead in bringing these biologics to the clinic, but we believe that this new class of therapeutics has the potential to be a powerful option for the control of influenza. The biologics have a possible broader application in blocking other respiratory pathogens that utilize sialic acid in pathogenesis, including *Streptococcus pneumoniae*, a leading cause of secondary bacterial infection often associated with influenza and responsible for increased morbidity and mortality[29].

TABLE 1

Kinetic parameters for the different mCBMs interacting with multivalent α-2,3-sialyllactose.

| mCBM | T (° C.) | $k_a$ (×10$^6$)† (M$^{-1}$ s$^{-1}$) | $k_d$ (×10$^{-3}$)‡ (s$^{-1}$) | $K_D$ § |
|---|---|---|---|---|
| Vc4CBM | 15 | 0.54 ± 0.01 | 0.51 ± 0.01 | 0.94 |
|  | 25 | 3.56 ± 0.02 | 1.60 ± 0.01 | 0.45 |
|  | 37 | 2.98 ± 0.02 | 5.41 ± 0.04 | 1.82 |
| VcCBMT | 15 | 2.55 ± 0.02 | 4.20 ± 0.02 | 1.65 |
|  | 25 | 7.24 ± 0.06 | 12.4 ± 0.10 | 1.71 |
|  | 37 | 20.7 ± 0.54 | 107. ± 2.80 | 5.15 |
| Vc2CBM | 15 | 1.83 ± 0.01 | 0.33 ± 0.01 | 0.18 |
|  | 25 | 1.73 ± 0.01 | 0.70 ± 0.01 | 0.41 |
|  | 37 | 8.45 ± 0.05 | 2.07 ± 0.01 | 0.24 |
| SpCBMT | 15 | 0.73 ± 0.01 | 0.30 ± 0.01 | 0.41 |
|  | 25 | 3.49 ± 0.02 | 1.37 ± 0.01 | 0.39 |
|  | 37 | 1.95 ± 0.01 | 0.90 ± 0.01 | 0.46 |
| Sp2CBM | 15 | 0.03 ± 0.00 | 0.56 ± 0.04 | 17.2 |
|  | 25 | 2.39 ± 0.01 | 1.35 ± 0.01 | 0.56 |
|  | 37 | 0.70 ± 0.01 | 3.65 ± 0.04 | 5.21 |

†$k_a$ represents the association ('on') rate constant expressed as the mean ± s.d. of three replicates.
‡$k_d$ represents the dissociation ('off') rate constant expressed as the mean ± s.d of three replicates.
§ $K_D$, represents the dissociation constant for each interaction between an mCBM and α-2,3-sialyllactose at three different temperatures, as determined by a global fit model (assuming Langmuir binding), derived from the ratio of $k_d/k_a$.

TABLE 2

In vitro cell protection, virus inhibition and cell viability of the mCBMs.

| | Cell protection EC50 (μM)* | | | | | Therapeutic Index (TI)‡ | | | |
|---|---|---|---|---|---|---|---|---|---|
| mCBM | A/WSN/ H1N1 | A/PR8/ H1N1 | A/Udorn/ H3N2 | B/HK/73 | CC50 (μM)† | A/WSN/ H1N1 | A/PR8/ H1N1 | A/Udorn/ H3N2 | B/HK/73 |
| Vc4CBM | 1.08 ± 0.01 | 1.43 ± 0.33 | 0.49 ± 0.01 | 1.97 ± 0.83 | >58.75 | >54 | >41 | >119 | >30 |
| VcCBMTD | 1.07 ± 0.43 | 2.75 ± 0.25 | 0.87 ± 0.32 | 3.95 ± 0.45 | >50 | >46 | >18 | >57 | >13 |

TABLE 2-continued

In vitro cell protection, virus inhibition and cell viability of the mCBMs.

| | | | | | | | | | |
|---|---|---|---|---|---|---|---|---|---|
| Vc2CBMTD | 0.39 ± 0.02 | 0.90 ± 0.03 | 0.47 ± 0.05 | 0.62 ± 0.08 | >30.5 | >79 | >34 | >65 | >49 |
| SpCBMTD | 1.11 ± 0.01 | 3.80 ± 0.03 | 0.82 ± 0.09 | 4.10 ± 0.10 | >50 | >43 | >13 | >61 | >12 |
| Sp2CBMTD | 3.10 ± 0.40 | 1.85 ± 0.55 | 0.55 ± 0.15 | 2.80 ± 0.80 | >30.5 | >9 | >16 | >55 | >11 |

| | Viral replication inhibition EC50(µM)§ | | |
|---|---|---|---|
| mCBM | A/WSN/H1N1 | A/PR8/H1N1 | A/Udorn/H3N2 |
| Vc4CBM | 1.10 ± 0.03 | 4.80 ± 1.68 | 2.60 ± 1.60 |
| VcCBMTD | 3.20 ± 0.50 | 10.75 ± 4.75 | 1.70 ± 0.02 |
| Vc2CBMTD | 0.50 ± 0.07 | 1.34 ± 0.65 | 0.45 ± 0.05 |
| SpCBMTD | 4.25 ± 0.75 | 44.50 ± 0.50 | 5.70 ± 1.30 |
| Sp2CBMTD | 3.35 ± 0.65 | 10.00 ± 1.20 | 2.05 ± 0.95 |

*$EC_{50}$ is the concentration of mCBM that provides 50% cell protection, expressed as mean ± s.d. from three independent determinations, †$CC_{50}$ values determined by the PrestoBlue cell viability assay as described in Full Methods, with > sign representing values using maximum feasible concentration.

‡Therapeutic index is calculated from the ratio $CC_{50}$/*$EC_{50}$.

§$EC_{50}$ values determined by the concentration of mCBM that inhibits 50% viral replication expressed as mean ± s.d. from three independent determinations.

TABLE 3

Primers used for engineering the mCBMs.

| | Features | Primers | Linker sequences |
|---|---|---|---|
| VcCBMTD | NcoI-VcCBM-BamHI-PaTD-Stop-XhoI | VcCBMNcoI(F) 5' GGCTCCATGGCACTTTTTGACTATAACGC 3' (SEQ ID NO: 7)<br>VcCBMBamHI(R) 5' GCACGGATCCACCACCGTCGCCTTGAATTTC 3' (SEQ ID NO: 8)<br>PaTDBamHI(F) 5' GGCTGGATCCGGTATGGTCCCGGATTTTGAGTCA 3' (SEQ ID NO: 9)<br>PaTDXhoI(R) 5' CCGACTCGAGCTAAATCCATGCTCTGACCCG 3' (SEQ ID NO: 10) | GGGSG (SEQ ID NO: 27) |
| Vc2CBMTD | NcoI-VcCBM-BamHI-VcCBM-HindIII-PaTD-Stop-XhoI | VcCBMNcoI(F) 5' GGCTCCATGGCACTTTTTGACTATAACGC 3' (SEQ ID NO: 11)<br>VcCBMBamHI(R) 5' GCACGGATCCACCACCGTCGCCTTGAATTTC 3' (SEQ ID NO: 12)<br>VcCBMBamHI(F) 5' GGCTGGATCCGGTGCACTTTTTGACTATAAC 3' (SEQ ID NO: 13)<br>VcCBMHindIII(R) 5' GTCCCAAGCTTGACCGTCGCCTTGAATTTC 3' (SEQ ID NO: 14)<br>PaTDHindIII(F) 5' CTGCAAGCTTTGGGAGTCCCGGATTTTGAGTCAG 3' (SEQ ID NO: 15)<br>PaTDXhoI(R) 5' CCGACTCGAGCTAAATCCATGCTCTGACCCG 3' (SEQ ID NO: 16) | GGGSG (SEQ ID NO: 27) and GQALG (SEQ ID NO: 28) |
| SpCBMTD | NcoI-SpCBM-BamHI-PaTD-Stop-XhoI | SpCBMNcoI(F) 5' GGCTCCATGGTGATAGAAAAAGAAGATG 3' (SEQ ID NO: 17)<br>SpCBMBamHI(R) 5' ACCGGATCCACCACCACTACGTTTTTGTACCTC 3' (SEQ ID NO: 18)<br>PaTDBamHI(F) 5' GGCTGGATCCGGTATGGTCCCGGATTTTGAGTCA 3' (SEQ ID NO: 19)<br>PaTDXhoI(R) 5' CCGACTCGAGCTAAATCCATGCTCTGACCCG 3' (SEQ ID NO: 20) | GGGSG (SEQ ID NO: 27) |
| Sp2CBMTD | NcoI-SpCBM-BamHI-SpCBM-HindIII-PaTD-Stop-XhoI | SpCBMNcoI(F) 5' GGCTCCATGGTGATAGAAAAAGAAGATG 3' (SEQ ID NO: 21)<br>SpCBMBamHI(R) 5' ACCGGATCCACCACCACTACGTTTTTGTACCTC 3' (SEQ ID NO: 22)<br>SpCBMBamHI(F) 5' GGCTGGATCCGGTGTGATAGAAAAAGAAGATG 3' (SEQ ID NO: 23)<br>SpCBMHindIII(R) 5' TCCCAAGCTTGACCACTACGTTTTTGTGCCTC 3' (SEQ ID NO: 24)<br>PaTDHindIII(F) 5' CTGCAAGCTTTGGGAGTCCCGGATTTTGAGTCAG 3' (SEQ ID NO: 25)<br>PaTDXhoI(R) 5' CCGACTCGAGCTAAATCCATGCTCTGACCCG 3' (SEQ ID NO: 26) | GGGSG (SEQ ID NO: 27) and GQALG (SEQ ID NO: 28) |

TABLE 3-continued

Primers used for engineering the mCBMs.

| Features | | Primers | Linker sequences |
|---|---|---|---|
| GFP-Sp2CBMTD* | GFP-NcoI-SpCBM-BamHI-SpCBM-HindIII-PaTD-Stop-XhoI | As for Sp2CBMTD | |

*SpCBM gene fused in-frame with GFP gene using pEHISTEV-GFP vector as described in Full Methods.
Restriction enzyme sites in primers are highlighted in bold.

References for Example 1

1. Salomon, R. & Webster, R. G. The influenza virus enigma. Cell 136, 402-410 (2009).
2. Gao, R. et al. Human infection with a novel avian-origin influenza A (H7N9) virus. N. Engl. J. Med. 368, 1888-1897 (2013).
3. Imai, M. et al. Experimental adaptation of an influenza H5 HA confers respiratory droplet transmission to a reassortant H5 HA/H1N1 virus in ferrets. Nature 486, 420-428 (2012).
4. Herfst, S. et al. Airborne transmission of influenza A/H5N1 virus between ferrets. Science 336, 1534-1541 (2012).
5. Russell, C. A. et al. The potential for respiratory droplet-transmissible A/H5N1 influenza virus to evolve in a mammalian host. Science 336, 1541-1547 (2012).
6. Hu, Y. et al. Association between adverse clinical outcome in human disease caused by novel influenza A H7N9 virus and sustained viral shedding and emergence of antiviral resistance. Lancet 381, 2273-2279 (2013).
7. Baz, M. et al. Emergence of oseltamivir-resistant pandemic H1N1 virus during prophylaxis. N. Engl. J. Med. 361, 2296-2297 (2009).
8. Connaris, H., Crocker, P. R. & Taylor, G. L. Enhancing the receptor affinity of the sialic acid-binding domain of Vibrio cholerae sialidase through multivalency. J. Biol. Chem. 284, 7339-7351 (2009).
9. Suzuki, T. et al. Receptor specificities of human respiroviruses. J. Virol. 75, 4604-4613 (2001).
10. Schwegmann-Wessels, C. & Herrler, G. Sialic acids as receptor determinants for coronaviruses. Glycoconj. J. 23, 51-58 (2006).
11. Trappetti, C. et al. Sialic acid: a preventable signal for pneumococcal biofilm formation, colonization, and invasion of the host. J. Infect. Dis. 199, 1497-1505 (2009).
12. Skehel, J. J. & Wiley, D. C. Receptor binding and membrane fusion in virus entry: the influenza hemagglutinin. Ann. Rev. Biochem. 69, 531-569 (2000).
13. Shinya, K. et al. Avian flu: influenza virus receptors in the human airway. Nature 440, 435-436 (2006).
14. Walther, T. et al. Glycomic analysis of human respiratory tract tissues and correlation with influenza virus infection. PLoS pathogens 9, e1003223 (2013).
15. Xiong, X. et al. Receptor binding by an H7N9 influenza virus from humans. Nature 499, 496-499 (2013).
16. Zhou, J. et al. Biological features of novel avian influenza A (H7N9) virus. Nature 499, 500-503 (2013).
17. Mammen, M., Choi, S. K. & Whitesides, G. M. Polyvalent interactions in biological systems: Implications for design and use of multivalent ligands and inhibitors. Angew. Chem. Int. Ed. 37, 2755-2794 (1998).
18. Moustafa, I. et al. Sialic acid recognition by Vibrio cholerae neuraminidase. J. Biol. Chem. 279, 40819-40826 (2004).
19. Xu, G., Ryan, C., Kiefel, M. J., Wilson, J. C. & Taylor, G. L. Structural studies on the Pseudomonas aeruginosa sialidase-like enzyme PA2794 suggest substrate and mechanistic variations. J. Mol. Biol. 386, 828-840 (2009).
20. Cantor, J. R. et al. Therapeutic enzyme deimmunization by combinatorial T-cell epitope removal using neutral drift. Proc. Natl. Acad. Sci. USA 108, 1272-1277 (2011).
21. Varki, A. & Gagneux, P. Multifarious roles of sialic acids in immunity. Ann. New York Acad. Sci. 1253, 16-36 (2012).
22. Varki, A. Glycan-based interactions involving vertebrate sialic-acid-recognizing proteins. Nature 446, 1023-1029 (2007).
23. Banerjee, A. et al. Activation of brain endothelium by pneumococcal neuraminidase NanA promotes bacterial internalization. Cell. Microbiol. 12, 1576-1588 (2010).
24. Ekiert, D. C. & Wilson, I. A. Broadly neutralizing antibodies against influenza virus and prospects for universal therapies. Curr. Opin. Virology. 2, 134-141 (2012).
25. Osterhaus, A., Fouchier, R. & Rimmelzwaan, G. Towards universal influenza vaccines? Phil. Trans. Roy. Soc. B 366, 2766-2773 (2011).
26. Boltz, D. A., Aldridge, J. R., Jr., Webster, R. G. & Govorkova, E. A. Drugs in development for influenza. Drugs 70, 1349-1362 (2010).
27. Ludwig, S. Disruption of virus-host cell interactions and cell signaling pathways as an anti-viral approach against influenza virus infections. Biol. Chem. 392, 837-847 (2011).
28. Moss, R. B. et al. A phase II study of DAS181, a novel host directed antiviral for the treatment of influenza infection. J. Infect. Dis. 206, 1844-1851 (2012).
29. Morens, D. M., Taubenberger, J. K. & Fauci, A. S. Predominant role of bacterial pneumonia as a cause of death in pandemic influenza: implications for pandemic influenza preparedness. J. Infect. Dis. 198, 962-970 (2008).
30. Ilyushina, N. A. et al. Adaptation of pandemic H1N1 influenza viruses in mice. J. Virol. 84, 8607-8616 (2010).
31. Cantarel, B. L. et al. The Carbohydrate-Active EnZymes database (CAZy): an expert resource for Glycogenomics. Nuc. Acids Res. 37, D233-238 (2009).
32. Xu, G., Li, X., Andrew, P. W. & Taylor, G. L. Structure of the catalytic domain of Streptococcus pneumoniae sialidase NanA. Acta Cryst. F64, 772-775 (2008).

EXAMPLE 2: Prophylactic Effects of Engineered Proteins VC2CBMTD and SP2CBMTD on Mice Infected with Murine Gammaherpesvirus 68 (MHV-68)

Introduction

Murine gammaherpesvirus 68 (MHV-68) is a naturally occurring rodent respiratory pathogen[1] that is closely related to the Kaposi's Sarcoma-associated herpesvirus (KSHV) and the Epstein-Barr virus (EBV) that infect humans[2]. Gammaherpesviruses display a number of surface proteins, glycoprotein H (gH) and glycoprotein L (gL) and glycoprotein 150 (gp150) on their envelopes that are involved in the cell-to-cell transmission of the virus. Like EBV, MHV-68 is associated with lymphoproliferative disease[3], which can occur many months after infection. However, unlike EBV and many other gammaherpesviruses, MHV-68 replicates in epithelial cells in vitro and infects laboratory strains of mice and therefore provides a good model for the study of gammaherpesviruses[4]. As for treatment, antiviral agents are normally suggested for the treatment of most herpesvirus infections. Intranasal administration of MHV-68 in mice results in acute productive infection of lung alveolar epithelial cells and a persistent latent infection in B lymphocytes, the spleen being a major reservoir of latent virus[5,6]. Infectious virus can also be recovered from the lungs of BALB/c mice for 10 to 13 days after infection[5]. Analysis of the inflammatory cytokine response to MHV-68 from BAL fluid after intranasal infection of C57BL/6J mice with MHV-68, show high levels of IL-6 and IFN-γ and lower levels of IL-2 and IL-10 with cytokine production peaking around 10 days after infection, correlating with viral clearance from the lung, although significant levels are seen as early as 3 days after administration of the virus. In contrast, negligible levels of IL-4 or IL-5 are detected. Furthermore, purified immune T cells also produce IL-6, IL-10, and IFN-γ following in vitro re-stimulation with MHV-68, suggesting the virus induces components of both the acquired and the innate host response[1].

Recent evidence in our laboratory using engineered sialic acid binding proteins as biologics against respiratory pathogens has shown that when these are intranasally administered in mice using a single low dose (1 μg) up to 7 days in advance, complete protection is observed against lethal influenza A/California/04/2009 (H1N1) virus challenge (unpublished data). The biologics are based on carbohydrate-binding modules isolated from *V. cholerae* (Vc) and *S. pneumoniae* (Sp) sialidase enzymes and engineered as multivalent entities (mCBMs) using either a tandem repeat or an oligomerisation domain approach. As these engineered proteins have been shown to protect the host when given many days in advance at a low dose, it is thought that these proteins not only block the attachment of influenza viruses from binding to cell surface sialic acid but can also potentially "prime" the immune system, to allow an antiviral response against the virus via an immunomodulatory effect. Preliminary studies using mCBMs in BALB/c mice showed that when administered intranasally as a single dose in absence of an infection, an immunostimulatory effect was observed, demonstrating an ability to enhance the production of a limited set of cytokines/chemokines such as MIP-2, TNF-α, IL-6, and IL-1β after 2 days (unpublished data).

Here we show preliminary data of the effect of engineered mCBMs in MHV-68 infected BALB/c mice on virus titre and cytokine levels. The reduction in virus titres and specific cytokine levels in infected mice demonstrate that mCBMs have the potential to affect the infection process by other respiratory pathogens that do not rely on sialic acid binding to initiate infection in mammals.

Methods

In Vivo Studies.

Mouse studies were conducted at the animal testing facility for influenza research at the Centre for Infectious Diseases, Edinburgh, and carried out under a UK Home Office License according to the Animals (Scientific Procedures) Act 1986. Mice were anaesthetized using halothane (Rhone Merieux Ltd, Harlow, Essex, UK) before intranasally administering 50 μg of either Vc2CBMTD or Sp2CBMTD given three times on Day −7, Day −3 and Day −1 before challenge with $4 \times 10^5$ MHV68 in 40 μl of PBS. On day 5 post infection, mice were culled and their lungs harvested post mortem for virus titre determination and cytokine analysis.

Virus Titres.

Infectious virus titres were determined by standard plaque assays on MDCK cells. Lung virus titres in mice determined 5 days p.i.

Cytokine Analysis.

Cytokine analyses of MIP-2, TNF-α, IL-6, IL-1β, IFN-γ, GM-CSF and IL-2 from clarified mouse lung homogenates were performed using Quantikine ELISA kits according to manufacturer's instructions (RD Biosystems, UK).

Statistical Analysis.

Data plotted with error bars are expressed as means±s.d. unless otherwise indicated. Statistical significance ($p<0.05$) between two groups was determined using the nonparametric Mann Whitney U test. GraphPad Prism 5.0 package (GraphPad Software Inc., La Jolla, Calif.) was used for all analysis.

Results and Discussion

We explored the effect of hexameric mCBMs, Vc2CBMTD and Sp2CBMTD on the lung viral load and immune response in BALB/c mice when challenged with a non-sialic acid binding respiratory pathogen, MHV-68 virus. Biologics were administered intranasally as a triple dose (50 ug, Day −7, −3, −1) prior to viral challenge. All treated mice demonstrated a one-logarithm reduction in lung virus titres 5 days p.i. compared to untreated, infected mice (FIG. 12a). Further analysis of mice lung homogenates using ELISA to monitor inflammatory mediators IL-1β, MIP-2 (mouse homologue of IL-8), IFN-γ, TNF-α, GM-CSF, IL-6 and IL-2, demonstrated differences between treated and untreated, infected mice. Both biologics showed significant lower levels of IL-6, MIP-2 and IFN-γ compared to untreated, infected mice, whereas levels of TNF-α, IL-2 and IL-1β were similar to infected mice only (FIG. 12b). This data suggests that advanced prophylactic treatment of mCBMs may prepare the host to respond to infection by modulating the immune response as seen by the reduction in levels of specific inflammatory mediators stimulated by MHV-68 infection such as IL-6 and IFN-γ. It is likely that mCBMs induce an initial inflammatory process to enhance the immune response to MHV-68 virus challenge while preventing potentially damaging chemokine expression. Further work is required to understand the type of immune response profiles of mCBMs when administered in animal models.

References for Example 2

1 Sarawar, S. R. et al. Cytokine production in the immune response to murine gammaherpesvirus 68. *J Virol* 70, 3264-3268 (1996).

2 Efstathiou, S. et al. Murine herpesvirus 68 is genetically related to the gammaherpesviruses Epstein-Barr virus and herpesvirus saimiri. *J Gen Virol* 71 (Pt 6), 1365-1372 (1990).

3 Sunil-Chandra, N. P., Arno, J., Fazakerley, J. & Nash, A. A. Lymphoproliferative disease in mice infected with murine gammaherpesvirus 68. *Am J Pathol* 145, 818-826 (1994).

4 Stewart, J. P. et al. Identification and characterization of murine gammaherpesvirus 68 gp150: a virion membrane glycoprotein. *J Virol* 70, 3528-3535 (1996).

5 Sunil-Chandra, N. P., Efstathiou, S. & Nash, A. A. Murine gammaherpesvirus 68 establishes a latent infection in mouse B lymphocytes in vivo. *J Gen Virol* 73 (Pt 12), 3275-3279 (1992).

6 Sunil-Chandra, N. P., Efstathiou, S., Arno, J. & Nash, A. A. Virological and pathological features of mice infected with murine gamma-herpesvirus 68. *J Gen Virol* 73 (Pt 9), 2347-2356 (1992).

EXAMPLE 3: Carbohydrate-Binding Modules Against H7N9 Influenza Virus Infection: Efficacy in Preclinical Studies. Effect of Hexameric Form of Carboxydrate-Binding Module (SP2CBMTD) Against A/ANHUI/1/2013 (H7N9) Influenza Virus Infection in BALB/C Mice Materials and Methods
Virus.

Influenza A/Anhui/1/2013 (H7N9) virus was obtained through the World Health Organization surveillance network. A/Anhui/1/2013 (H7N9) virus was isolated from a patient by culturing clinical sample in the allantoic cavity of 10-days old embryonated chicken eggs (eggs), and the stock of virus used in the experiments was prepared in eggs (passage history: E2/E2). The mouse lethal dose that killed 50% of animals ($MLD_{50}$) was determined in 6-week-old female BALB/c mice after 21 days (weight, 18-20 g; Jackson Laboratories, Bar Harbor, Me.). Animals that showed severe disease and lost >25% of initial weight were euthanized.

Experiments with human H7N9 influenza virus were conducted in an animal biosafety level 3+ containment facility approved by the U.S. Department of Agriculture. All studies were conducted under applicable laws and guidelines and after approval from the St. Jude Children's Research Hospital animal care and use committee.

Compound.

Hexameric form of Carbohydrate-Binding Module (Sp2CBMTD) was provided in PBS at concentration of 10.5 mg/ml by Dr. Helen Connaris (Centre for Biomolecular Sciences, University of St. Andrews, UK). The 6CBM (Sp2CBMTD) protein was stored at −80° C. until use. To assess the efficacy of the 6CBM (Sp2CBMTD) protein in a mouse animal model, the protein sample was centrifuged for 5 mins at 13K rpm, transferred into a new vial and dissolved in sterile PBS to a desired concentration.

SDS-Polyacrylamide Gel Electrophoresis (SDS-PAGE).

Figure 13:
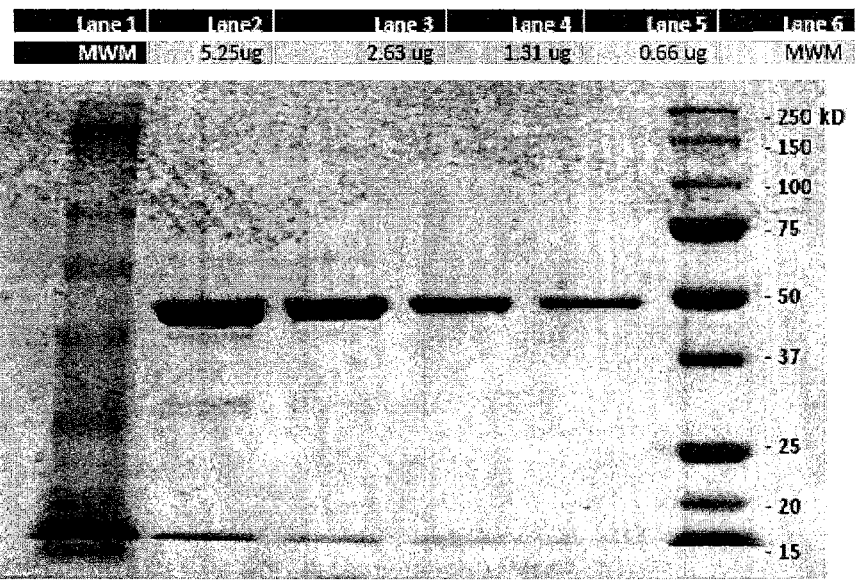

Protein stability was confirmed by determination of electrophoretic mobility of Sp2CBMTD protein (10 µl/channel at concentrations 5.25-0.66 µg/channel dissolved in PBS) under reducing conditions in 12% SDS-PAGE (BioRad laboratories, Hercules, Calif.). The main protein band was identified at 50 kDa, and some additional minor bands (FIG. 13). No band was detected at 21 kDa. Thus, Sp2CBMTD protein was not dissociated.

Efficacy of Sp2CBMTD on Lethal Infection with A/Anhui/1/2013 (H7N9) Influenza Virus in Mice.

Female 6- to 8-week-old BALB/c mice (weight, 18 to 20 g; Jackson Laboratories, Bar Harbor, Me.) were lightly anesthetized by inhalation of isofluorane and inoculated intranasally with 50 µl of infectious H7N9 virus. Overall, 32 groups of BALB/c mice (5 mice per group) were used in this experiment (Table 1a). BALB/c mice were given 50 µl of Sp2CBMTD intranasally at different regimens. Single dose (0.1, 1, 10, and 100 µg/mouse/day) of Sp2CBMTD protein was administered either 7 days before H7N9 virus challenge (Day −7: groups 1-4), 3 days before H7N9 virus challenge (Day −3: groups 5-8), 1 day before H7N9 virus challenge (Day −1: groups 9-12), 6 hours after H7N9 virus challenge (+6 hr: groups 13-16), 24 hours after H7N9 virus challenge (Day +1: groups 17-20). Repeated administration of Sp2CBMTD protein was conducted as two doses administered on days 3 and 1 before H7N9 virus challenge (Day −3, −1: groups 21-24) or as three doses administered on days 7, 3 and 1 before virus challenge (Day −7, −3, −1: groups 25-28). As a toxicity control Sp2CBMTD protein was administered at a dose of 100 µg/mouse/day at three regimens (Toxicity: groups 29-31). Animals were inoculated with A/Anhui/1/2013 (H7N9) influenza virus at a dose of 5 $MLD_{50}$ per mouse. Control (infected untreated) mice received 50 µl of sterile PBS intranasally 1 hour before virus inoculation. BALB/c mice were observed daily for 21 days p.i. for clinical signs of infection and for survival. The mean day to death was calculated by using the log-hazard scale. The mice were weighed on days 0, 2, 4, 6, 8, 10, 12, 14, 19 and 21 p.i., and the loss or gain of weight was calculated for each mouse as a percentage of its weight on day 0 before virus inoculation.

Anti-HA Antibody Response.

Serum samples were collected from survived mice 21 days p.i., treated with 1:10 diluted receptor-destroying enzyme (Denka Seiken Co., Japan) overnight at 37° C., heat-inactivated at 56° C. for 30 min, diluted 1:10 with sterile PBS, and tested by hemagglutination inhibition (HI) assay with 0.5% packed chicken red blood cells (CRBC).

Re-Infection with a Higher H7N9 Virus Dose.

All animals that survived lethal infection with A/Anhui/1/2013 (H7N9) influenza virus were re-infected with 25 $MLD_{50}$ of virus on day 21 p.i. The mice were observed daily for clinical signs of infection and survival and weight changes were monitored on designated days.

Results

Efficacy of Sp2CBMTD Protein on Survival of BALB/c Mice Lethally Challenged with A/Anhui/1/2013 (H7N9) Influenza Virus.

We evaluated the effect of a single or repeated administration of Sp2CBMTD protein on the survival and clinical signs of mice lethally challenged with A/Anhui/1/2013 (H7N9) influenza virus (Table 2a). Sp2CBMTD did not cause any weight changes and death of uninfected mice when administered as a single dose, 2× and 3× doses (100 µg/mouse/day). We concluded that Sp2CBMTD is nontoxic for mice at a highest dose used in these experiments.

Untreated H7N9 virus-inoculated control mice exhibited progressive weight loss with a mean day to death of 7.8±1.1 (Table 2a and FIGS. 14-16). We observed dose-dependent effect of Sp2CBMTD on protection of mice against H7N9 virus challenge, and more beneficial protection was achieved at higher dose of 100 µg/mouse/day (FIG. 14). The dose of 100 µg/mouse/day provided 100% protection when administered D-7, D-3, D-1. Dose of 0.1 µg/mouse/day was the least effective dose when applied as a single administration at all regimens tested.

To assess the effect of a single Sp2CBMTD dose when administered after lethal challenge with A/Anhui/1/2013 (H7N9), we initiated treatments either 6 hours or 24 hours after virus inoculation (FIG. 15). The highest dose used in these experiments (100 µg/mouse/day) provided 100% survival if applied +6 hours, and only 40% of animals survived if applied +24 hours (Day +1).

To assess the efficacy of repeated dosing with Sp2CBMTD against lethal challenge of mice with A/Anhui/1/2013 (H7N9) virus, two doses of protein were administered D-3, −1, and three doses were administered on D-7,−3, 1 (FIG. 16). There was 100% survival for all dosing regimens when Sp2CBMTD was applied 2× and 3×.

Efficacy of Sp2CBMTD Protein on Weight Changes of BALB/c Mice Lethally Challenged with A/Anhui/1/2013 (H7N9) Influenza Virus.

Weight changes were little or absent when the highest Sp2CBMTD dose of 100 µg/mouse/day was administered to the animals. On the other hand, the dose of 0.1 µg/mouse/day provided minimal effect on the weight loss and animals treated with this dose experienced the most pronounced weight loss (Table 3a). Timing of Sp2CBMTD administration is critical for providing the most beneficial effect on survival and weight loss. When treatment with Sp2CBMTD protein was initiated 24 hours after virus inoculation, the animals exhibited the most pronounced weight changes. Overall, observed weight changes correlated with survival outcome observed after H7N9 infections.

To serologically confirm infection of mice with A/Anhui/1/2013 (H7N9) influenza virus and to compare the effect of the Sp2CBMTD protein regimens on production of anti-HA antibodies, we collected serum 21 days p.i. for HI assay. Anti-HA antibodies to homologous A/Anhui/1/2013 (H7N9) influenza virus were observed in all surviving mice with reciprocal HI titers ranging between 40-80 (Table 4a).

Re-Infection of Survived Mice with a Higher Dose of H7N9 Virus.

Animals were completely protected from re-infection with 25 MLD$_{50}$ of H7N9 virus; they showed no disease signs and none died (Table 5a).

Conclusions

Repeated administration of Sp2CBMTD before lethal challenge with A/Anhui/1/2013 (H7N9) influenza virus provided the most beneficial results and resulted in 100% survival of BALB/c mice even at the lowest dose used (0.1 µg/mouse/day). This indicates a possibility for the reduction in dosages used.

Time of administration is associated with the efficacy of Sp2CBMTD protein treatment in a lethal mouse model: complete protection (100% survival rates) was achieved when protein was administered before A/Anhui/1/2013 (H7N9) influenza virus inoculation.

The Sp2CBMTD dose-dependent effect was observed in a H7N9 lethal mouse model, thus indicating the specificity of this protein against influenza virus.

Administration of Sp2CBMTD did not affect development of anti-HA antibodies, and the level of immune response was sufficient to protect against H7N9 virus re-infection.

TABLE 1a

Design of the studies to assess the effect of Sp2CBMTD against A/Anhui/1/2013 (H7N9) influenza virus infection in BALB/c mice.

| Group | Dosage of Sp2CBMTD (µg/mouse/day) | Schedule of drug administration | Initiation of treatments |
|---|---|---|---|
| 1 | 0.1 | Single administration (intranasaly) −7 Day p.i. | 7 days before virus inoculation |
| 2 | 1 | Single administration (intranasaly) −7 Day p.i. | 7 days before virus inoculation |
| 3 | 10 | Single administration (intranasaly) −7 Day p.i. | 7 days before virus inoculation |
| 4 | 100 | Single administration (intranasaly) −7 Day p.i. | 7 days before virus inoculation |
| 5 | 0.1 | Single administration (intranasaly) −3 Day p.i. | 3 days before virus inoculation |
| 6 | 1 | Single administration (intranasaly) −3 Day p.i. | 3 days before virus inoculation |
| 7 | 10 | Single administration (intranasaly) −3 Day p.i. | 3 days before virus inoculation |
| 8 | 100 | Single administration (intranasaly) −3 Day p.i. | 3 days before virus inoculation |
| 9 | 0.1 | Single administration (intranasaly) −1 Day p.i. | 1 day before virus inoculation |
| 10 | 1 | Single administration (intranasaly) −1 Day p.i. | 1 day before virus inoculation |
| 11 | 10 | Single administration (intranasaly) −1 Day p.i. | 1 day before virus inoculation |
| 12 | 100 | Single administration (intranasaly) −1 Day p.i. | 1 day before virus inoculation |
| 13 | 0.1 | Single administration (intranasaly) +6 hr p.i.. | 6 hrs after virus inoculation |
| 14 | 1 | Single administration (intranasaly) +6 hr p.i.. | 6 hrs after virus inoculation |
| 15 | 10 | Single administration (intranasaly) +6 hr p.i.. | 6 hrs after virus inoculation |
| 16 | 100 | Single administration (intranasaly) +6 hr p.i.. | 6 hrs after virus inoculation |
| 17 | 0.1 | Single administration (intranasaly) +24 hr p.i. | 24 hrs after virus inoculation |
| 18 | 1 | Single administration (intranasaly) +24 hr p.i. | 24 hrs after virus inoculation |
| 19 | 10 | Single administration (intranasaly) +24 hr p.i. | 24 hrs after virus inoculation |
| 20 | 100 | Single administration (intranasaly) +24 hr p.i. | 24 hrs after virus inoculation |
| 21 | 0.1 | x2 administration (intranasaly) −3 and −1 Days p.i. | 3 and 1 days before virus inoculation |
| 22 | 1 | x2 administration (intranasaly) −3 and −1 Days p.i. | 3 and 1 days before virus inoculation |
| 23 | 10 | x2 administration (intranasaly) −3 and −1 Days p.i. | 3 and 1 days before virus inoculation |
| 24 | 100 | x2 administration (intranasaly) −3 and −1 Days p.i. | 3 and 1 days before virus inoculation |
| 25 | 0.1 | x3 administration (intranasaly) −7, −3 and −1 Days p.i. | 7, 3 and 1 days before virus inoculation |
| 26 | 1 | x3 administration (intranasaly) −7, −3 and −1 Days p.i. | 7, 3 and 1 days before virus inoculation |
| 27 | 10 | x3 administration (intranasaly) −7, −3 and −1 Days p.i. | 7, 3 and 1 days before virus inoculation |
| 28 | 100 | x3 administration (intranasaly) −7, −3 and −1 Days p.i. | 7, 3 and 1 days before virus inoculation |
| 29 | 100 (Toxicity) | Single administration (intranasaly) −7 Day p.i. | Toxicity control |
| 30 | 100 (Toxicity) | x2 administration (intranasaly) −7 and −1 Days p.i. | Toxicity control |

TABLE 1a-continued

Design of the studies to assess the effect of Sp2CBMTD against A/Anhui/1/2013 (H7N9) influenza virus infection in BALB/c mice.

| Group | Dosage of Sp2CBMTD (µg/mouse/day) | Schedule of drug administration | Initiation of treatments |
|---|---|---|---|
| 31 | 100 (Toxicity) | x3 administration (intranasaly) −7, −3 and −1 Days p.i. | Toxicity control |
| 32 | Control (PBS) | — | Day 0 p.i. |

TABLE 2a

Efficacy of Sp2CBMTD protein on survival of BALB/c mice lethally challenged with A/Anhui/1/2013 (H7N9) influenza virus.

| Group | Dosage of Sp2CBMTD (µg/mouse/day) | Schedule of drug administration (intranasal administration) | No. of survivors/total no. of mice (%) | Mean day to death |
|---|---|---|---|---|
| 1 | 0.1 | Day −7 | 1/5 (20) | 10.4 ± 5.5 |
| 2 | 1 | Day −7 | 1/5 (20) | 11.2 ± 4.9 |
| 3 | 10 | Day −7 | 4/5 (80) | 17.8 ± 4.9 |
| 4 | 100 | Day −7 | 5/5 (100) | >21 |
| 5 | 0.1 | Day −3 | 1/5 (20) | 11.2 ± 4.9 |
| 6 | 1 | Day −3 | 5/5 (100) | >21 |
| 7 | 10 | Day −3 | 5/5 (100) | >21 |
| 8 | 100 | Day −3 | 5/5 (100) | >21 |
| 9 | 0.1 | Day −1 | 1/5 (20) | 11.2 ± 4.9 |
| 10 | 1 | Day −1 | 2/5 (40) | 13.4 ± 6.0 |
| 11 | 10 | Day −1 | 5/5 (100) | >21 |
| 12 | 100 | Day −1 | 5/5 (100) | >21 |
| 13 | 0.1 | +6 hr p.i. | 0/5 (0) | 7.8 ± 1.1 |
| 14 | 1 | +6 hr p.i. | 4/5 (80) | 17.4 ± 5.5 |
| 15 | 10 | +6 hr p.i. | 5/5 (100) | >21 |
| 16 | 100 | +6 hr p.i. | 5/5 (100) | >21 |
| 17 | 0.1 | Day +1 | 0/5 (0) | 7.0 ± 0.0 |
| 18 | 1 | Day +1 | 0/5 (0) | 7.0 ± 0.0 |
| 19 | 10 | Day +1 | 1/5 (20) | 9.6 ± 5.8 |
| 20 | 100 | Day +1 | 2/5 (40) | 12.2 ± 7.1 |
| 21 | 0.1 | 2x (Day −3, −1) | 5/5 (100) | >21 |
| 22 | 1 | 2x (Day −3, −1) | 5/5 (100) | >21 |
| 23 | 10 | 2x (Day −3, −1) | 5/5 (100) | >21 |
| 24 | 100 | 2x (Day −3, −1) | 5/5 (100) | >21 |
| 25 | 0.1 | 3x (Day −7, −3, −1) | 5/5 (100) | >21 |
| 26 | 1 | 3x (Day −7, −3, −1) | 5/5 (100) | >21 |
| 27 | 10 | 3x (Day −7, −3, −1) | 5/5 (100) | >21 |
| 28 | 100 | 3x (Day −7, −3, −1) | 5/5 (100) | >21 |
| 29 | 100 (Toxicity) | Day −7 | 5/5 (100) | >21 |
| 30 | 100 (Toxicity) | 2x (Day −3, −1) | 5/5 (100) | >21 |
| 31 | 100 (Toxicity) | 3x (Day −7, −3, −1) | 5/5 (100) | >21 |
| 32 | Control | Control | 0/5 (0) | 7.8 ± 1.1 |

TABLE 3a

Efficacy of Sp2CBMTD protein on weight changes of BALB/c mice lethally challenged with A/Anhui/1/2013 (H7N9) influenza virus.

| Group | Dosage of Sp2CBMTD (µg/mouse/d) | Schedule of drug administration (intranasal administration) | Mean weight change (%) on day post virus inoculation[a] | | | | |
|---|---|---|---|---|---|---|---|
| | | | 2 p.i. | 4 p.i. | 6 p.i. | 8 p.i. | 10 p.i. | 12 p.i. |
| 1 | 0.1 | Day −7 | −1.6 | −7.9 | −13.0 | −20.7 | −17.0 | 0.8 |
| 2 | 1 | Day −7 | −0.7 | −6.6 | −10.0 | −22.0 | −24.6 | −8.6 |
| 3 | 10 | Day −7 | −0.02 | −3.3 | −8.4 | −16.5 | −12.2 | −3.6 |
| 4 | 100 | Day −7 | 0.5 | −1.2 | −3.5 | −6.6 | −1.2 | 1.8 |
| 5 | 0.1 | Day −3 | 1.5 | 4.1 | −7.6 | −17.1 | −21.2 | −7.1 |
| 6 | 1 | Day −3 | 0.6 | −2.7 | −6.0 | −12.3 | −7.1 | −2.9 |
| 7 | 10 | Day −3 | 1.2 | −0.1 | −1.6 | −5.6 | −0.1 | 0.5 |
| 8 | 100 | Day −3 | 1.4 | 0.7 | −2.0 | −0.7 | 3.4 | 4.4 |
| 9 | 0.1 | Day −1 | −3.4 | −6.6 | −13.0 | −19.6 | −24.9 | −0.4 |
| 10 | 1 | Day −1 | 2.4 | −4.6 | −11.1 | −22.1 | −21.5 | 1.7 |
| 11 | 10 | Day −1 | −0.3 | −0.5 | −5.8 | −7.8 | −1.8 | −0.1 |
| 12 | 100 | Day −1 | 2.8 | 4.6 | 3.0 | 5.3 | 8.12 | 7.5 |
| 13 | 0.1 | +6 hr p.i. | 0.1 | −6.1 | −12.0 | −25.4 | −27.0 | N/A |
| 14 | 1 | +6 hr p.i. | 1.0 | −3.3 | −10.1 | −18.4 | −8.6 | −3.4 |
| 15 | 10 | +6 hr p.i. | −0.7 | −2.1 | −5.6 | −10.0 | 4.4 | 0.8 |
| 16 | 100 | +6 hr p.i. | −5.1 | −3.4 | −2.7 | −3.1 | 2.4 | 2.4 |
| 17 | 0.1 | Day +1 | 0.7 | −15.4 | −23.6 | −31.6 | N/A | N/A |
| 18 | 1 | Day +1 | −1.2 | −16.4 | −25.0 | −32.6 | N/A | N/A |
| 19 | 10 | Day +1 | −2.5 | −13.0 | −19.4 | −26.6 | −17.2 | −11.2 |
| 20 | 100 | Day +1 | −4.8 | −14.1 | −18.2 | −23.9 | −13.3 | −10.3 |
| 21 | 0.1 | 2x (Day-3, −1) | 1.5 | −3.3 | −6.6 | −17.0 | −12.9 | −7.4 |
| 22 | 1 | 2x (Day-3, −1) | 1.6 | 0 | −2.6 | −8.1 | 1.5 | 3.8 |
| 23 | 10 | 2x (Day-3, −1) | 2.0 | 1.1 | −0.4 | −1.5 | 3.0 | 4.7 |
| 24 | 100 | 2x (Day-3, −1) | 2.3 | 5.0 | 3.6 | 4.5 | 7.1 | 7.9 |
| 25 | 0.1 | 3x (Day-7, −3, −1) | 0 | −2.7 | −5.8 | −15.2 | −7.8 | −1.6 |
| 26 | 1 | 3x (Day-7, −3, −1) | −0.9 | −3.0 | −5.5 | −10.3 | −3.0 | −1.4 |
| 27 | 10 | 3x (Day-7, −3, −1) | 1.1 | −1.1 | −2.0 | −0.4 | 3.8 | 4.3 |
| 28 | 100 | 3x (Day-7, −3, −1) | 3.8 | 6.0 | 5.1 | 5.5 | 10.0 | 10.7 |

TABLE 3a-continued

Efficacy of Sp2CBMTD protein on weight changes of BALB/c mice lethally challenged with A/Anhui/1/2013 (H7N9) influenza virus.

| Group | Dosage of Sp2CBMTD (μg/mouse/d) | Schedule of drug administration (intranasal administration) | Mean weight change (%) on day post virus inoculation[a] | | | | | |
|---|---|---|---|---|---|---|---|---|
| | | | 2 p.i. | 4 p.i. | 6 p.i. | 8 p.i. | 10 p.i. | 12 p.i. |
| 29 | 100 (Toxicity) | Day −7 | 2.7 | 8.5 | 10.0 | 9.6 | 10.5 | 12.1 |
| 30 | 100 (Toxicity) | 2x (Day−3, −1) | 3.2 | 7.2 | 9.2 | 8.6 | 9.7 | 12.3 |
| 31 | 100 (Toxicity) | 3x (Day−7, −3, −1) | 5.5 | 8.9 | 11.2 | 10.2 | 11.3 | 13.4 |
| 32 | Control | Control | 0.5 | −6.8 | −11.9 | −24.7 | −35.7 | N/A |

[a]Loss or gain of weight was calculated for each mouse as a percentage of weight on day 0 before A/Anhui/1/2013 (H7N9) influenza virus inoculation.
N/A - data is not available due to deceased mice.

TABLE 4a

Serum antibody responses in BALB/c mice lethally challenged with A/Anhui/1/2013 (H7N9) influenza virus and treated with Sp2CBMTD protein.

| Group | Dosage of Sp2CBMTD (μg/mouse/day) | Schedule of drug administration (intranasal administration) | Anti-HA antibody titers in mouse sera[a] | |
|---|---|---|---|---|
| | | | Range | Geometric mean |
| 1 | 0.1 | Day −7 | 80-80 | 80 |
| 2 | 1 | Day −7 | 40-80 | 50 |
| 3 | 10 | Day −7 | 40-80 | 57 |
| 4 | 100 | Day −7 | 40-40 | 40 |
| 5 | 0.1 | Day −3 | 40-40 | 40 |
| 6 | 1 | Day −3 | 40-40 | 40 |
| 7 | 10 | Day −3 | 40-80 | 46 |
| 8 | 100 | Day −3 | 40-40 | 40 |
| 9 | 0.1 | Day −1 | 80-80 | 80 |
| 10 | 1 | Day −1 | 40-80 | 50 |
| 11 | 10 | Day −1 | 40-40 | 40 |
| 12 | 100 | Day −1 | 40-40 | 40 |
| 13 | 0.10 | +6 hr p.i. | N/A | N/A |
| 14 | 1 | +6 hr p.i. | 40-80 | 53 |
| 15 | 10 | +6 hr p.i. | 40-40 | 40 |
| 16 | 100 | +6 hr p.i. | 40-80 | 53 |
| 17 | 0.1 | Day +1 | N/A | N/A |
| 18 | 1 | Day +1 | N/A | N/A |
| 19 | 10 | Day +1 | 40-40 | 40 |
| 20 | 100 | Day +1 | 40-80 | 50 |
| 21 | 0.1 | 2x (Day −3, −1) | 40-80 | 46 |
| 22 | 1 | 2x (Day −3, −1) | 40-40 | 40 |
| 23 | 10 | 2x (Day −3, −1) | 40-40 | 40 |
| 24 | 100 | 2x (Day −3, −1) | 40-80 | 46 |
| 25 | 0.1 | 3x (Day −7, −3, −1) | 40-80 | 53 |
| 26 | 1 | 3x (Day −7, −3, −1) | 40-40 | 40 |
| 27 | 10 | 3x (Day −7, −3, −1) | 40-40 | 40 |
| 28 | 100 | 3x (Day −7, −3, −1) | 40-40 | 40 |
| 31 | Control | Control | N/A | N/A |

[a] Sera samples were collected from all survived animal 21 day p.i. The titers are determined against homologous A/Anhui/1/2013 (H7N9) influenza virus with 0.5% CRBC and expressed as the reciprocal value (e.g., 640 vs. 1:640).
N/A—data is not available due to deceased mice.

TABLE 5a

Efficacy of Sp2CBMTD protein on survival of BALB/c mice re-infected with 25 $MLD_{50}$ of A/Anhui/1/2013 (H7N9) influenza virus.

| Group | Dosage of Sp2CBMTD (μg/mouse/day) | Schedule of drug administration (intranasal administration) | No. of survivors/ total no. of mice | Mean day to death |
|---|---|---|---|---|
| 1 | 0.1 | Day −7 | 1/1 | >21 |
| 2 | 1 | Day −7 | 1/1 | >21 |
| 3 | 10 | Day −7 | 4/4 | >21 |
| 4 | 100 | Day −7 | 5/5 | >21 |
| 5 | 0.1 | Day −3 | 1/1 | >21 |
| 6 | 1 | Day −3 | 5/5 | >21 |
| 7 | 10 | Day −3 | 5/5 | >21 |
| 8 | 100 | Day −3 | 5/5 | >21 |
| 9 | 0.1 | Day −1 | 1/1 | >21 |
| 10 | 1 | Day −1 | 2/2 | >21 |
| 11 | 10 | Day −1 | 5/5 | >21 |
| 12 | 100 | Day −1 | 5/5 | >21 |
| 13 | 0.1 | +6 hr p.i. | N/A | N/A |
| 14 | 1 | +6 hr p.i. | 4/4 | >21 |
| 15 | 10 | +6 hr p.i. | 5/5 | >21 |
| 16 | 100 | +6 hr p.i. | 5/5 | >21 |
| 17 | 0.1 | Day +1 | N/A | N/A |
| 18 | 1 | Day +1 | N/A | N/A |
| 19 | 10 | Day +1 | 1/1 | >21 |
| 20 | 100 | Day +1 | 2/2 | >21 |
| 21 | 0.1 | 2x (Day −3, −1) | 5/5 | >21 |
| 22 | 1 | 2x (Day −3, −1) | 5/5 | >21 |
| 23 | 10 | 2x (Day −3, −1) | 5/5 | >21 |
| 24 | 100 | 2x (Day −3, −1) | 5/5 | >21 |
| 25 | 0.1 | 3x (Day −7, −3, −1) | 5/5 | >21 |
| 26 | 1 | 3x (Day −7, −3, −1) | 5/5 | >21 |
| 27 | 10 | 3x (Day −7, −3, −1) | 5/5 | >21 |
| 28 | 100 | 3x (Day −7, −3, −1) | 5/5 | >21 |
| 29 | 100 (Toxicity) | Day −7 | 0/5 (0) | 8.0 ± 0.0 |
| 30 | 100 (Toxicity) | 2x (Day −3, −1) | 0/5 (0) | 8.0 ± 0.0 |
| 31 | 100 (Toxicity) | 3x (Day −7, −3, −1) | 0/5 (0) | 8.0 ± 0.0 |
| 32 | Control | Control | N/A | N/A |

Note:
Toxicity groups were infected with 5 $MLD_{50}$ of A/Anhui/1/2013 (H7N9) influenza virus. Toxicity groups received SP2CBMTD ~27 days before lethal challenge with H7N9 virus did not survive infection. This was primary infection for toxicity group. All other groups were re-infected with 25 $MLD_{50}$ of A/Anhui/1/2013 (H7N9) influenza virus but previously they were infected with 5 $MLD_{50}$ of A/Anhui/1/2013 (H7N9) influenza virus.

TABLE 6a

Serum antibody responses in BALB/c mice re-infected with 25 MLD$_{50}$ of A/Anhui/1/2013 (H7N9) influenza virus.

| Group | Dosage of Sp2CBMTD (μg/mouse/day) | Schedule of drug administration (intranasal administration) | Anti-HA antibody titers in mouse sera[a] Range | Geometric mean |
|---|---|---|---|---|
| 1 | 0.1 | Day −7 | 80-80 | 80 |
| 2 | 1 | Day −7 | 80-80 | 80 |
| 3 | 10 | Day −7 | 80-160 | 101 |
| 4 | 100 | Day −7 | 80-160 | 101 |
| 5 | 0.1 | Day −3 | 80-80 | 80 |
| 6 | 1 | Day −3 | 80-80 | 80 |
| 7 | 10 | Day −3 | 80-80 | 80 |
| 8 | 100 | Day −3 | 80-80 | 80 |
| 9 | 0.1 | Day −1 | 160-160 | 160 |
| 10 | 1 | Day −1 | 160-160 | 160 |
| 11 | 10 | Day −1 | 80-80 | 80 |
| 12 | 100 | Day −1 | 80-80 | 80 |
| 13 | 0.1 | +6 hr p.i. | N/A | N/A |
| 14 | 1 | +6 hr p.i. | 80-160 | 127 |
| 15 | 10 | +6 hr p.i. | 80-160 | 101 |
| 16 | 100 | +6 hr p.i. | 80-80 | 80 |
| 17 | 0.1 | Day +1 | N/A | N/A |
| 18 | 1 | Day +1 | N/A | N/A |
| 19 | 10 | Day +1 | 80-80 | 80 |
| 20 | 100 | Day +1 | 80-160 | 113 |
| 21 | 0.1 | 2x (Day −3, −1) | 80-160 | 101 |
| 22 | 1 | 2x (Day −3, −1) | 80-160 | 101 |
| 23 | 10 | 2x (Day −3, −1) | 80-80 | 80 |
| 24 | 100 | 2x (Day −3, −1) | 80-80 | 80 |
| 25 | 0.1 | 3x (Day −7, −3, −1) | 80-160 | 101 |
| 26 | 1 | 3x (Day −7, −3, −1) | 80-160 | 101 |
| 27 | 10 | 3x (Day −7, −3, −1) | 80-80 | 80 |
| 28 | 100 | 3x (Day −7, −3, −1) | 80-80 | 80 |
| 32 | Control | Control | N/A | N/A |

[a] Sera samples were collected from all survived animal 42 days after initial infection or 21 day after re-infection with A/Anhui/1/2013 (H7N9) virus. The titers are determined against homologous A/Anhui/1/2013 (H7N9) influenza virus with 0.5% CRBC and expressed as the reciprocal value (e.g., 640 vs. 1:640).
N/A—data is not available due to deceased mice.

EXAMPLE 4: Further Studies Regarding Sialic Acid—Binding Protein SP2CBMTD Protects Mice Against Lethal Challenge with the Emerging A(H7N9) Influenza Virus Summary As shown by the data presented in Example 3, compounds that target the cellular factors essential for influenza virus replication represent an attractive approach to antiviral therapy. Sp2CBMTD is a genetically engineered multivalent protein that masks sialic acid-containing cellular receptors on the respiratory epithelium which are recognized by influenza viruses. The antiviral potential of Sp2CBMTD against lethal infection of mice with an emerging human A/Anhui/1/2013(H7N9) influenza virus was investigated as was the mechanistic basis of its activity in vivo. Sp2CBMTD was administered to mice intranasally as a single or repeated dose (0.1, 1, 10, or 100 μg) before (day 7, 3, or 1) or after (6 or 24 h) H7N9 virus inoculation. A single Sp2CBMTD dose (10 or 100 μg) protected 80% to 100% of mice when administered 7 days before the H7N9 lethal challenge. Repeated Sp2CBMTD administration conferred the highest protection, resulting in 100% survival of mice even at the lowest dose tested (0.1 μg). Administration of Sp2CBMTD induced pulmonary expression of proinflammatory mediators (IL-6, RANTES, MCP-1, Il-1β, TNFα, MIP-1α, IP-10) and recruited neutrophils to the respiratory tract before H7N9 virus infection, which resulted in less pronounced inflammation and rapid virus clearance from mouse lungs. Sp2CBMTD administration did not affect the virus-specific adaptive immune response, which was sufficient to protect against reinfection with a higher dose of homologous H7N9 virus or heterologous H5N1 virus. Thus, Sp2CBMTD was effective in preventing H7N9 infections in a lethal mouse model and holds promise as a prophylaxis option against zoonotic influenza viruses.

Materials and Methods

Viruses, Cells, and Biologic.

Influenza A/Anhui/1/2013(H7N9) and A/Turkey/15/2006 (H5N1) viruses were obtained through the World Health Organization network and propagated in embryonated chicken eggs for 48 h at 35° C. Madin-Darby canine kidney (MDCK) cells were obtained from the American Type Culture Collection and maintained as described previously (22). Sp2CBMTD was generated by PCR-based cloning techniques, using genes encoding the carbohydrate-binding module 40 (CBM40) domain from *Streptococcus pneumoniae* NanA sialidase and the trimerization domain from *Pseudomonas aeruginosa* pseudaminidase (21). Experiments with H7N9 and H5N1 influenza viruses were conducted in an animal biosafety level 3+ containment facility approved by the US Department of Agriculture.

Efficacy of Sp2CBMTD in Mice.

Six-week-old female BALB/c mice (weight, 18-20 g; Jackson Laboratories, Bar Harbor, Me.) were lightly anesthetized by isoflurane inhalation and inoculated intranasally with five 50% mouse lethal doses (MLD50) of A/Anhui/1/2013(H7N9) influenza virus in 50 μL of PBS. For the first study, 5 BALB/c mice per group were given a single dose of Sp2CBMTD (0.1, 1, 10, or 100 μg/mouse) intranasally on day 7, 3, or 1 before inoculation, or 6 or 24 h after H7N9 virus inoculation. Repeated dosing with Sp2CBMTD was given either as double (days 3 and 1) or triple (days 7, 3, and 1) doses before the H7N9 inoculation. Survival of mice was monitored daily for 21 days post-infection (p.i.); animals that showed signs of severe disease and a 25% weight loss were sacrificed. Control mice received sterile PBS on day 7, 3, and 1.

For the second study, the 10 μg dose of Sp2CBMTD was evaluated. Ten BALB/c mice per group were given single (day 7 or 3), double (days 3 and 1), or triple (days 7, 3, and 1) dose(s) of Sp2CBMTD before A/Anhui/1/2013(H7N9) influenza virus inoculation. The loss or gain of weight was calculated for each mouse as a percentage of its weight before inoculation. On days 3, 6, and 9 p.i., 3 mice from each group were sacrificed for the determination of virus lung titers and level of cytokine/chemokine responses in the lung homogenates. Additional 3 mice from each group were sacrificed for histopathological examination of the lungs. The lungs were removed, thoroughly rinsed with sterile PBS, homogenized, and suspended in 1 mL of ice cold PBS. Cellular debris was removed by centrifugation at 2000 g for 10 min, after which the supernatants were used for 50% tissue culture infectious dose (TCID50) assays in MDCK cells. Survival of mice was monitored daily for 21 days p.i. All studies were conducted under applicable laws and guidelines and approved by the St. Jude Children's Research Hospital Animal Care and Use Committee.

Reinfection With H7N9 and H5N1 Viruses.

Three weeks after inoculation with A/Anhui/1/2013 (H7N9) influenza virus, surviving mice were reinfected with 25 MLD50 of homologous virus. Other mice that survived an initial treatment with Sp2CBMTD and H7N9 virus inoculation received a second administration of Sp2CBMTD after 3 weeks and were then infected with 20 MLD50 of A/Turkey/15/2006(H5N1) virus.

Lung Cytokine and Chemokine Analysis.

Concentrations of the 4 cytokines [gamma interferon (IFN-γ), interleukin-6 (IL-6), regulated upon activation, normal T cell expressed and secreted (RANTES), monocyte chemotactic protein-1 (MCP-1)], and 4 chemokines [interleukin-1β (II-1β), tumor necrosis factor alpha (TNF-α), macrophage inflammatory protein-1α (MIP-1α), inducible protein (IP-10)] were measured using a mouse MYCTO-MAG-70K-PMX MILLIPLEX® premixed kit (Millipore) according to the manufacturer's instructions. For each cytokine, the standard curve ranged from 3.2 to 10,000 μg/mL. Cytokines were measured in 25 μL of lung homogenate samples at 0, 3, 6, and 9 days p.i. Multiplex plates were read on the Luminex 100/200 analyzer, using the xPonent data acquisition and analysis software.

Histopathology and Immunohistochemistry.

Lungs of mice in each experimental group (n=3) of the second study were collected after whole-body perfusion with 10% neutral buffered formalin (NBF). Mouse lungs underwent inflation via tracheal infusion and were kept in 10% NBF for at least 7 days before embedding, sectioning, and staining for conventional histopathology with hematoxylin and eosin or with immunohistochemical (IHC) staining for influenza A virus [nucleoprotein (NP); US Biological], and neutrophils [myeloperoxidase (MPO); Thermo Shandon). Influenza A virus NP- and MPO-stained sections were blinded for pathology evaluation. The presence of antigens was quantified by capturing digital images of whole-lung sections, using an Aperio ScanScope XT Slide Scanner (Aperio Technologies) and then manually outlining entire fields together with areas of noticeably decreased or absent NP and MPO staining. The percentage of lung field with reduced staining coverage was calculated by using the Aperio's ImageScope software.

Serology.

Serum samples were obtained 21 days after H7N9 or H5N1 virus infection, treated with receptor-destroying enzyme (Denka Seiken Co.), heat inactivated at 56° C. for 1 h, and tested for the presence of anti-hemagglutinin (HA) antibodies by the HA inhibition assay with 0.5% turkey red blood cells (Rockland Immunochemicals). The presence of anti-SpCBM antibodies in sera samples was measured in an ELISA, using purified protein (1 μg/well) immobilized on 96-well plates (Corning) (21).

Statistical Analysis.

Virus lung titers, concentrations of cytokines and chemokines, and anti-SpCBM antibody titers were analyzed by the unpaired Student t test. The number of NP- and MPO-stained lung cells were compared by analysis of variance (ANOVA), using the GraphPad Prism 5.0 software. Cumulative survival was calculated by the Kaplan-Meier log-rank test.

Results

Efficacy of Sp2CBMTD on Survival of Mice Lethally Challenged with H7N9 Influenza Virus.

To determine whether Sp2CBMTD improved the survival of mice lethally challenged with A/Anhui/1/2013(H7N9) influenza virus, the biologic was administered once at a dose of 0.1, 1, 10, or 100 μg on day 7, 3, or 1 before virus challenge. Virus-inoculated, PBS treated control animals exhibited progressive weight loss and all died between days 8 and 10 p.i. (FIG. 17). A single intranasal administration of Sp2CBMTD before the H7N9 virus challenge resulted in a dose-dependent protection of mice. The highest single dose of Sp2CBMTD (100 μg) provided the greatest protection, and 100% of mice survived the infection when the biologic was administered on day 7, 3, or 1 before virus inoculation (FIG. 17A). The 10 μg single dose protected 100%, 80%, and 80% of mice when administered on day 1, or on day 7 or 3 before virus inoculation, respectively. However, only 60% and 40% of mice survived when the 1 μg dose was administered on day 3 or 1 before virus challenge (FIG. 17A). The lowest dose tested (0.1 μg) was the least effective, and only 20% of mice were protected.

Next, the effect of early post exposure treatment with Sp2CBMTD on the survival of mice was assessed. Sp2CBMTD given 6 h after the H7N9 virus challenge protected 100% of mice at doses of 10 and 100 μg and 40% of mice at 1 μg (FIG. 17B). The efficiency of protection decreased when initiation of treatment was delayed by 24 h: only 40% of mice treated with 100 μg survived H7N9 inoculation; 0.1 or 1 μg did not provide survival benefits.

Repeated administration of Sp2CBMTD given as a double or triple regimen before lethal challenge of mice infected with A/Anhui/1/2013(H7N9) influenza virus provided complete protection at all doses of the biologic tested (FIG. 17C). These results indicated that repeated administration of Sp2CBMTD before H7N9 virus inoculation was the most effective for survival of mice and minimization of weight loss (Table 1b).

Effect of Sp2CBMTD on H7N9 Influenza Virus Replication in Mouse Lungs.

In a second experiment, the mechanistic basis of the antiviral activity of Sp2CBMTD was examined at a 10 μg dose, at which protection was conferred in the first experiment. The kinetics of H7N9 virus load was determined in the lungs of infected mice. Virus titers in the lungs of mice treated with all biologic regimens tested did not differ from those of controls on day 3 or 6 p.i. (Table 1 b). Notably, on day 9 p.i., double and triple administration of Sp2CBMTD significantly reduced virus load in the lungs of infected mice ($P<0.005$), but both single dose regimens tested did not reduce virus titers (Table 1b).

To compare A/Anhui/1/2013(H7N9) influenza virus replication in the lower respiratory tract of infected mice given either PBS (control) or different regimens of the biologic, virus positive cells were quantified in lung sections on days 3, 6, and 9 p.i. (FIG. 18). In control animals, NP-positive cells (a measure of influenza infected cells) were detected throughout the whole-lung sections, specifically in epithelial cells of the bronchi, bronchiole, and peribronchiolar alveoli on days 3 and 6 p.i. (FIG. 18D, F), and the number of antigen-positive cells decreased on day 9 p.i. (FIG. 18H). Single administration of Sp2CBMTD did not significantly change the number of NP-positive cells in mouse lungs compared with control animals on day 3, 6, or 9 p.i. In contrast, double or triple administration of the biologic resulted in a significant decrease ($P<0.01$ and $P<0.05$, respectively) in the number of NP-positive cells, with the cell number declining from 80% to 70% on day 3 p.i. (FIG. 18A), and to 50% on day 9 p.i. (FIG. 18C).

These findings indicated that Sp2CBMTD administration controlled H7N9 virus replication in the lungs of infected mice. The observed difference in the infectious virus titers and the number of virus-positive cells in the lungs of infected mice can be because the lung section assay can detect only intracellular virus but the TCID50 assay can detect both intracellular and extracellular viruses.

Effect of Sp2CBMTD on Histologic Changes of Lung Tissues.

To determine the extent of changes in the lungs, tissues obtained from different Sp2CBMTD regimen groups on days 3, 6, and 9 p.i. were histologically examined (FIG. 19). Lungs of H7N9-infected PBS-treated mice showed necrosis of epithelial cells in the bronchi on day 3 p.i. (FIG. 19A) and alveolar collapses and infiltration with inflammatory cells (neutrophils and macrophages), edema, and viral pneumonia on day 6 p.i. (FIG. 19B). Edema and infiltration with inflammatory cells continued on day 9 p.i., but lesions were restricted to a few areas (FIG. 19C). In Sp2CBMTD-treated mice receiving a triple-dose regimen, there were no distinctive pathologic changes on day 3 p.i. and epithelial necrosis and infiltration of the alveoli with inflammatory cells was minimal (FIG. 19D). The accumulation of inflammatory cells in the lung parenchyma and progression of virus spread was observed on day 6 p.i. and resolved on day 9 p.i. (FIG. 19E, F). These findings support that Sp2CBMTD administration decreases lung tissue damage, which is associated with lethal H7N9 virus infection.

Effect of Sp2CBMTD on Production of Pulmonary Cytokines and Chemokines.

To determine the inflammatory and innate immune responses associated with Sp2CBMTD administration, the effect of Sp2CBMTD on pulmonary expression of cytokines and chemokines was studied. Sp2CBMTD stimulated a proinflammatory response before H7N9 virus inoculation and the levels of specific proinflammatory mediators such as cytokines (IL-6, RANTES, MCP-1) and chemokines (II-1β, TNFα, MIP-1α, IP-10) increased, and the significant differences ($P<0.01$ or $P<0.05$) were observed between Sp2CBMTD-treated and control animals on day 0 p.i. especially with repeat dosing (FIG. 20). These effects may be due to activated alveolar macrophages in the lungs. The pulmonary expression of cytokines and chemokines varied between experimental groups on days 3, 6 and 9 p.i., and there was no clear pattern of expression (data not shown). These results suggest that Sp2CBMTD might modulate the immune response by "priming" the host to better combat an oncoming influenza virus infection.

Effect of Sp2CBMTD on Neutrophil Recruitment.

To confirm that the elevated levels of cytokines determined before virus inoculation were associated with an increase in immune cell population in the lungs, the number of neutrophils was determined (FIG. 21). On day 0 p.i., neutrophil counts were significantly higher in samples from Sp2CBMTD-treated mice than controls ($P<0.0001$), with the greatest increase seen in samples obtained from mice given repeated Sp2CBMTD dosing (FIG. 21). Our results indicate that the recruitment of immune cells to the virus replication site caused by Sp2CBMTD administration contributed to rapid recovery and survival from lethal H7N9 virus infection.

Reinfection of Mice with H7N9 Influenza Virus.

To examine whether Sp2CBMTD treatment interferes with the induction of adaptive immunity, titers of serum anti-HA antibodies against A/Anhui/1/2013(H7N9) influenza virus were determined. All surviving mice had moderate titers of anti-HA antibodies (1:40 to 1:160), regardless of the regimen used (Table 2b). Anti-HA antibody titers were sufficient to protect 100% of surviving animals against a 25 MLD50 dose of homologous H7N9 virus reinfection (data not shown).

Induction of Anti-SpCBM Antibodies after Repeated Administration and Reinfection with H5N1 Influenza Virus.

Development of anti-biologic antibodies could potentially abrogate protection when the biologic is used repeatedly. We assessed the levels of anti-SpCBM antibodies in mouse sera after two uses of the biologic (Table 2b). Compared to naïve mice, the most prominent increase after the first use of Sp2CBMTD was observed for IgM, which presents the pool of acute antibodies, and the least increase was shown for IgA. After the second use of Sp2CBMTD, the levels of IgG and IgM increased 1.3-1.7 and 1.4-4.4-fold in all treatment groups, respectively (Table 2b). To address the question whether repeated Sp2CBMTD use can affect protection against influenza virus infection, we re-infected mice with highly pathogenic H5N1 virus. Importantly, animals in the groups that received the biologic twice were completely protected from lethal challenge with H5N1 virus (data not shown).

Discussion.

In a previously developed lethal mouse model of influenza H7N9 virus-induced acute respiratory distress syndrome (23), we demonstrated high potency of the novel host-targeted biologic Sp2CBMTD in preventing lethal infection with the newly emerging human pathogen. The highest efficacy and 100% protection of mice were achieved by repeated administration of Sp2CBMTD before the H7N9 viral challenge, although 20%-100% of animals were protected with a single dose of Sp2CBMTD after the viral challenge, depending on the timing and dose. Repeated administration of Sp2CBMTD induced some key proinflammatory cytokines and recruited immune cells to the lung epithelia before H7N9 virus infection, which resulted in less pronounced inflammation and rapid virus clearance from mouse lungs.

Human infection caused by avian influenza viruses raises concerns about optimal therapeutics to control zoonotic infections and highlights the need to develop novel anti influenza drugs. The targets for novel drugs have broadened in recent years, focusing on not only influenza virus-specific proteins but also host factors essential for virus replication. The major advantages of host-targeted drugs are their broad spectrum of activity and efficacy against different influenza virus subtypes and the low risk of emergence of drug-resistant variants (24). An attractive strategy for drug development is to inhibit influenza virus entry into the host cell. Therefore, Sp2CBMTD, which was designed to mask SA-containing host cell receptors, is a promising candidate. Unlike the investigational antiviral biologic DAS181, Sp2CBMTD does not remove cellular receptors but masks them and prevents viral attachment (21). Glycan array screening shows that SpCBM recognizes glycans containing terminal α2,3- or α2,6-linked SA (20), emphasizing the feasibility of a biologic that can bind to receptors in the upper and lower respiratory tract of humans. The high affinity of Sp2CBMTD, which was achieved through multivalency, allows it to mask SA receptors for an extended time period. Sp2CBMTD has been detected in mouse lungs up to 8 days after a single administration (21), which allows its administration in advance of virus infection, thus making it a valuable component of preventive measures. In contrast, recent studies on the antiviral activity of DAS181 in H7N9-infected mice show that daily dosing is required at the start of infection to reduce weight loss and completely protect mice from lethality (25). Despite the target (cell surface sialoglyconjugates) being identical for both drugs, the regimens are different.

Our data suggest that the mechanism of antiviral action of Sp2CBMTD is complex and is driven by 2 major factors: 1) preventing virus binding to the SA-containing cellular receptors (21) and 2) modulating host immune response. The multifunctional role of Sp2CBMTD in protecting against influenza virus infection is demonstrated by stimulation of an innate immune response and recruitment of immune cells to the site of influenza virus infection, thus reducing the severity of immunopathology induced by the H7N9 virus. It is possible that Sp2CBMTD binds to a yet-unknown receptor(s) in addition to SA, and thus acquired the ability to modulate the immune response.

Importantly, sera collected from Sp2CBMTD-treated mice that survived H7N9 virus infection were positive for specific anti-HA antibodies and thereby the development of an adaptive immune response has occurred. The level of immune response was sufficient to protect against H7N9 virus reinfection with a higher dose of the homologous virus.

A major concern about the long-term use of this novel therapeutic is the development of specific antibodies against it. Our results demonstrated that although serum levels of IgG, IgM, and IgA anti-SpCBM antibodies increased after a second administration of Sp2CBMTD three weeks after the first one, the protection was not affected and all animals survived the heterologous challenge with the highly pathogenic H5N1 influenza virus. All the internal gene segments of newly emerging H7N9 influenza viruses and highly pathogenic H5N1 are similar and closely related to those from avian H9N2 viruses (16, 26). Therefore, cross-reactive CD4+ T and CD8+ cytotoxic T lymphocyte immune responses established by the initial H7N9 virus infection may have contributed to protection against H5N1 reinfection. Further studies are required to determine the efficacy of Sp2CBMTD against different HA clades of highly pathogenic H5N1 influenza viruses. Our results confirm that repeated use of Sp2CBMTD is possible even within a short time period. If the time period between Sp2CBMTD administrations is longer, the anti-SpCBM antibodies could be eliminated and their possible effect on the level of protection may decrease. To reduce the possible concern of immunogenicity, humanization of the biologic is possible.

Sp2CBMTD represents a new host-directed class of therapeutics for influenza infections that shows promise for the prophylaxis of disease caused by potentially pandemic strains of influenza. Previous studies suggest that this biologic is effective against pandemic H1N1pdm09 viruses (21). Taken together, these data support the notion that Sp2CBMTD is a promising prophylaxis option against emerging influenza viruses. Other respiratory pathogens such as parainfluenza viruses, some coronaviruses, and *S. pneumoniae* also use SA receptors for pathogenesis, which may implement a broader application of the Sp2CBMTD in the future. Our findings in mice confirmed that a regimen of repeated low doses resulted in highest survival rates and minimized tissue damage in mouse lungs. The immunomodulatory properties of Sp2CBMTD require further investigation, but the findings of this study advocate an even broader applicability of this approach in preventing respiratory disease caused by pathogens that do not use SA receptors.

TABLE 1b

Efficacy of Sp2CBMTD against lethal A/Anhui/1/2013 (H7N9) influenza virus infection in BALB/c mice

| Sp2CBMTD administration[a] | No. survived/ total no. (%) | Mean survival day ± SD | Average weight loss (% ± SD) on day p.i.[b] | | | Mean lung virus titer ($\log_{10}TCID_{50}$/mL ± SD) on day p.i.[c] | | | |
|---|---|---|---|---|---|---|---|---|---|
| | | | 4 | 6 | 8 | 12 | 3 | 6 | 9 |
| Single (day 7)[d] | 6/10 (60) | 15.4 ± 5.9 | 10.5 ± 2.6 | 17.8 ± 3.7 | 24.9 ± 5.7 | 18.3 ± 8.3 | 6.8 ± 0.5 | 6.2 ± 0.0 | 5.5 ± 0.2 |
| Single (day 3) | 8/10 (80) | 17.8 ± 4.6 | 6.0 ± 4.0 | 13.4 ± 4.3 | 20.0 ± 8.1 | 7.4 ± 6.1 | 6.7 ± 0.3 | 5.6 ± 0.4 | 5.1 ± 0.3 |
| Double (days 3 and 1) | 10/10 (100) | 20.0 ± 0.0 | 6.2 ± 1.9 | 10.3 ± 2.4 | 13.3 ± 5.1 | 2.8 ± 4.5 | 6.8 ± 0.5 | 6.0 ± 0.3 | 2.9 ± 0.6* |
| Triple (days 7, 3, and 1) | 10/10 (100) | 20.0 ± 0.0 | 4.0 ± 2.8 | 10.1 ± 3.7 | 12.9 ± 6.8 | 0.9 ± 7.3 | 6.3 ± 0.1 | 5.8 ± 0.5 | 3.3 ± 0.0* |
| Control | 0/10 (0) | 8.0 ± 1.0 | 13.2 ± 2.5 | 20.2 ± 4.5 | 26.6 ± 4.9 | N/A | 7.0 ± 0.0 | 6.0 ± 0.3 | 5.4 ± 0.3 |

Abbreviations:
SD, standard deviation;
p.i., post infection;
N/A, not applicable (all mice in the group died).
[a]Groups of 6- to 8-week-old BALB/c mice (n = 10) were given 50 μL of Sp2CBMTD intranasally as a single, double, or triple dose of 10 μg/ mouse. Treatment with Sp2CBMTD was initiated at different time points between days 7 to 1 before inoculation with 5 MLD50 of A/Anhui/1/2013(H7N9) influenza virus.
[b]Loss of weight was calculated for each mouse as a percentage of its weight on day 0.
[c]Data from 3 animals per group. The lower limit of virus detection was 0.75 log10TCID50/mL.
[d]Days before A/Anhui/1/2013(H7N9) influenza virus inoculation.
*P26 <0.005, by unpaired Student t test as compared with control animals.

TABLE 2b

Titres of anti-HA and anti-SpCBM antibodies in mouse sera

| Sp2CBMTD administration[a] | Range of HI titers after infection with influenza virus | | Mean concentration (mg/mL ± SD) of anti-SpCBM antibodies after Sp2CBMTD administration | | | | | |
|---|---|---|---|---|---|---|---|---|
| | A/Anhui/1/ 2013 (H7N9)[b] | A/Turkey/15/ 2006 (H5N1)[c] | First administration[d] | | | Second administration[e] | | |
| | | | IgG | IgM | IgA | IgG | IgM | IgA |
| Single (day 7)[f] | 80 | 40-80 | 174.7 ± 7.0 (26.5) | 5.3 ± 3.0 (132.5) | 4.5 ± 3.3 (1.4) | 257.7 ± 0.2* (1.5) | 17.7 ± 0.2** (3.3) | 30.2 ± 6.1** (6.7) |
| Single (day 3) | 80-160 | 20-40 | 143.1 ± 7.4 (21.7) | 3.8 ± 1.2 (95.0) | 5.1 ± 4.6 (1.5) | 238.6 ± 2.9** (1.7) | 16.6 ± 1.1** (4.4) | 42.7 ± 9.1** (8.4) |
| Double (days 3 and 1) | 40-80 | 40-80 | 214.9 ± 9.0 (32.6) | 11.2 ± 1.9 (280.0) | 3.9 ± 2.8 (1.2) | 273.8 ± 1.4** (1.3) | 19.2 ± 0.7** (1.7) | 59.4 ± 2.6** (15.2) |

TABLE 2b-continued

Titres of anti-HA and anti-SpCBM antibodies in mouse sera

| | Range of HI titers after infection with influenza virus | | Mean concentration (mg/mL ± SD) of anti-SpCBM antibodies after Sp2CBMTD administration | | | | | |
|---|---|---|---|---|---|---|---|---|
| | A/Anhui/1/ | A/Turkey/15/ | First administration[d] | | | Second administration[e] | | |
| Sp2CBMTD administration[a] | 2013 (H7N9)[b] | 2006 (H5N1)[c] | IgG | IgM | IgA | IgG | IgM | IgA |
| Triple (days 7, 3, and 1) | 80-160 | 40-80 | 211.6 ± 16.1 (32.1) | 12.7 ± 2.2 (317.5) | 7.9 ± 5.5 (2.4) | 269.9 ± 1.6** (1.3) | 18.0 ± 0.4* (1.4) | 85.1 ± 13.5** (10.8) |
| Naïve mice | N/A | N/A | 6.6 ± 3.0 | 0.04 ± 0.1 | 3.3 ± 1.8 | 5.6 ± 0.4 | 0.1 ± 0.0 | 3.1 ± 1.8 |

Abbreviations:
SD, standard deviation;
HI, hemagglutination inhibition;
N/A, not applicable [naïve mice did not possess anti-HA antibodies against A/Anhui/1/2013 (H7N9) and A/Turkey/15/2006(H5N1) influenza viruses].
[a]Sp2CBMTD (10 μg/mouse) was administered as described in the legend to Table 1b. Three weeks after initial H7N9 virus inoculation and the first use of Sp2CBMTD, the biologic was used the second time and administered to the animals at the same regimens as during the first use. The animals were reinfected with 20 MLD50 of highly pathogenic A/Turkey/15/2006(H5N1) influenza virus (28 days p.i. with the H7N9 virus). Naïve mice did not receive Sp2CBMTD and were not infected with the influenza virus.
[b]HI titers against A/Anhui/1/2013(H7N9) influenza virus were determined 3 weeks after initial H7N9 virus inoculation (expressed as reciprocal values, e.g., 40 versus 1:40) using 0.5% turkey red blood cells.
[c]HI titers against A/Turkey/15/2006(H5N1) influenza virus were determined 3 weeks after initial H5N1 virus inoculation (or 48 days after H7N9 virus inoculation).
[d]Values are means ± SD from 4 mice per group. The fold change in the levels of anti-SpCBM antibodies relative to the mean concentrations of naive animals is shown in parenthesis.
[e]Values are means ± SD from 4 mice per group. The fold change in the levels of anti-SpCBM antibodies relative to the mean concentrations after the first administration is shown in parenthesis.
[f]Days before A/Anhui/1/2013(H7N9) influenza virus inoculation.
*P <0.05,
**P <0.005, by unpaired Student t test as compared to the concentration after the first administration of Sp2CBM References for Example 4

1. World Health Organization. Number of confirmed human cases of avian influenza A(H7N9) reported to WHO. Accessed 25 Sep. 2014.
2. Qi X, Qian Y H, Bao C J, Guo X L, Cui L B, Tang F Y, Ji H, Huang Y, Cai P Q, Lu B, Xu K, Shi C, Zhu F C, Zhou M H, Wang H. 2013. Probable person to person transmission of novel avian influenza A (H7N9) virus in Eastern China, 2013: epidemiological investigation. BMJ 347:f4752. doi: 10.1136/bmj.f4752.
3. Liu T, Bi Z, Wang X, Li Z, Ding S, Bi Z, Wang L, Pei Y, Song S, Zhang S, Wang J, Sun D, Pang B, Sun L, Jiang X, Lei J, Yuan Q, Kou Z, Yang B, Shu Y, Yang L, Li X, Lu K, Liu J, Zhang T, Xu A. 2014. One family cluster of avian influenza A(H7N9) virus infection in Shandong, China. BMC Infect. Dis. 14:98. doi: 10.1186/1471-2334-14-98.
4. Xiao X C, Li K B, Chen Z Q, Di B, Yang Z C, Yuan J, Luo H B, Ye S L, Liu H, Lu J Y, Nie Z, Tang X P, Wang M, Zheng B J. 2014. Transmission of avian influenza A(H7N9) virus from father to child: a report of limited person-to-person transmission, Guangzhou, China, January 2014. Euro Surveill. 19(25):pii=20837.
5. Hu J, Zhu Y, Zhao B, Li J, Liu L, Gu K, Zhang W, Su H, Teng Z, Tang S, Yuan Z, Feng Z, Wu F. 2014. Limited human-to-human transmission of avian influenza A(H7N9) virus, Shanghai, China, March to April 2013. Euro Surveill. 19(25): pii: 20838.
6. van Riel D, Leijten L M, Verdijk R M, GeurtsvanKessel C, van der Vries E, van Rossum A M, Osterhaus A D, Kuiken T. 2013. Novel avian-origin influenza A (H7N9) virus attaches to epithelium in both upper and lower respiratory tract of humans. Am. J. Pathol. 183:1137-1143. doi: 10.1016/j.ajpath.2013.06.011.
7. Zhou J, Wang D, Gao R, Zhao B, Song J, Qi X, Zhang Y, Shi Y, Yang L, Zhu W, Bai T, Qin K, Lan Y, Zou S, Guo J, Dong J, Dong L, Zhang Y, Wei H, Li X, Lu J, Liu L, Zhao X, Li X, Huang W, Wen L, Bo H, Xin L, Chen Y, Xu C, Pei Y, Yang Y, Zhang X, Wang S, Feng Z, Han J, Yang W, Gao G F, Wu G, Li D, Wang Y, Shu Y. 2013. Biological features of novel avian influenza A (H7N9) virus. Nature 499(7459):500-503. doi: 10.1038/nature12379.
8. Chan M C, Chan R W, Chan L L, Mok C K, Hui K P, Fong J H, Tao K P, Poon L L, Nicholls J M, Guan Y, Peiris J S. 2013. Tropism and innate host responses of a novel avian influenza A H7N9 virus: an analysis of ex-vivo and in-vitro cultures of the human respiratory tract. Lancet Respir. Med. 1(7):534-542. doi: 10.1016/S2213-2600(13) 70138-3.
9. Belser J A, Gustin K M, Pearce M B, Maines T R, Zeng H, Pappas C, Sun X, Carney P J, 458 Villanueva J M, Stevens J, Katz J M, Tumpey T M. 2013. Pathogenesis and transmission of avian influenza A (H7N9) virus in ferrets and mice. Nature 501(7468):556-559. doi: 10.1038/nature12391.
10. Watanabe T, Kiso M, Fukuyama S, Nakajima N, Imai M, Yamada S, Murakami S, Yamayoshi S, Iwatsuki-Horimoto K, Sakoda Y, Takashita E, McBride R, Noda T, Hatta M, Imai H, Zhao D, Kishida N, Shirakura M, de Vries R P, Shichinohe S, Okamatsu M, Tamura T, Tomita Y, Fujimoto N, Goto K, Katsura H, Kawakami E, Ishikawa I, Watanabe S, Ito M, Sakai-Tagawa Y, Sugita Y, Uraki R, Yamaji R, Eisfeld A J, Zhong G, Fan S, Ping J, Maher E A, Hanson A, Uchida Y, Saito T, Ozawa M, Neumann G, Kida H, Odagiri T, Paulson J C, Hasegawa H, Tashiro M, Kawaoka Y. 2013. Characterization of H7N9 influenza A viruses isolated from humans. Nature 501(7468):551-555. doi: 10.1038/nature12392.
11. Xu L, Bao L, Deng W, Dong L, Zhu H, Chen T, Lv Q, Li F, Yuan J, Xiang Z, Gao K, Xu Y, Huang L, Li Y, Liu J, Yao Y, Yu P, Li X, Huang W, Zhao X, Lan Y, Guo J, Yong W, Wei Q, Chen H, Zhang L, Qin C. 2014. Novel avian-origin human influenza A(H7N9) can be transmitted between ferrets via respiratory droplets. J. Infect. Dis. 209:551-556. doi: 10.1093/infdis/jit474.
12. Zhang Q, Shi J, Deng G, Guo J, Zeng X, He X, Kong H, Gu C, Li X, Liu J, Wang G, Chen Y, Liu L, Liang L, Li Y, Fan J, Wang J, Li W, Guan L, Li Q, Yang H, Chen P, Jiang L, Guan Y, Xin X, Jiang Y, Tian G, Wang X, Qiao C, Li C, Bu Z, Chen H. 2013. H7N9 influenza viruses are transmissible in ferrets by respiratory droplet. Science 341(6144):410-414. doi: 10.1126/science.
13. Osterholm M T, Ballering K S, Kelley N S. 2013. Major challenges in providing an effective and timely pandemic vaccine for influenza A(H7N9). JAMA 309:2557-2558. doi: 10.1001/jama.2013.6589.
14. De Groot A S, Ardito M, Terry F, Levitz L, Ross T, Moise L, Martin W. 2013. Low immunogenicity predicted for emerging avian-origin H7N9: implication for influenza vaccine design. Hum. Vaccin. Immunother. 9:950-956. doi: 10.4161/hv.24939.
15. Li Q, Zhou L, Zhou M, Chen Z, Li F, Wu H, Xiang N, Chen E, Tang F, Wang D, Meng L, Hong Z, Tu W, Cao Y, Li L, Ding F, Liu B, Wang M, Xie R, Gao R, Li X, Bai T, Zou S, He J, Hu J, Xu Y, Chai C, Wang S, Gao Y, Jin L, Zhang Y, Luo H, Yu H, He J, Li Q, Wang X, Gao L, Pang X, Liu G, Yan Y, Yuan H, Shu Y, Yang W, Wang Y, Wu F, Uyeki T M, Feng Z. 2014. Epidemiology of human infections with avian influenza A(H7N9) virus in China. N. Engl. J. Med. 370(6):520-532. doi: 10.1056/NEJ-Moa1304617.
16. Gao R, Cao B, Hu Y, Feng Z, Wang D, Hu W, Chen J, Jie Z, Qiu H, Xu K, Xu X, Lu H, Zhu W, Gao Z, Xiang N, Shen Y, He Z, Gu Y, Zhang Z, Yang Y, Zhao X, Zhou L, Li X, Zou S, Zhang Y, Li X, Yang L, Guo J, Dong J, Li Q, Dong L, Zhu Y, Bai T, Wang S, Hao P, Yang W, Zhang Y, Han J, Yu H, Li D, Gao G F, Wu G, Wang Y, Yuan Z, Shu Y. 2013. Human infection with a novel avian-origin influenza A (H7N9) virus. N. Engl. J. Med. 368 (20):1888-1897. doi: 10.1056/NEJMoa1304459.
17. Hu Y, Lu S, Song Z, Wang W, Hao P, Li J, Zhang X, Yen H L, Shi B, Li T, Guan W, Xu L, Liu Y, Wang S, Zhang X, Tian D, Zhu Z, He J, Huang K, Chen H, Zheng L, Li X, Ping J, Kang B, Xi X, Zha L, Li Y, Zhang Z, Peiris M, Yuan Z. 2013. Association between adverse clinical outcome in human disease caused by novel influenza A H7N9 virus and sustained viral shedding and emergence of antiviral resistance. Lancet 381(9885):2273-2279. doi: 10.1016/S0140-6736(13)61125-3.
18. Clinical Trials gov Identifier NCT00527865. Accessed 25 Sep. 2014.
19. Malakhov M P, Aschenbrenner L M, Smee D F, Wandersee M K, Sidwell R W, Gubareva L V, Mishin V P, Hayden F G, Kim D H, Ing A, Campbell E R, Yu M, Fang F. 2006. Sialidase fusion protein as a novel broad-spectrum inhibitor of influenza virus infection. Antimicrob. Agents Chemother. 50:1470-1479.
20. Connaris H, Crocker P R, and Taylor G L. 2009. Enhancing the receptor affinity of the sialic acid-binding domain of *Vibrio cholerae* sialidase through multivalency. J. Biol. Chem. 284(11):7339-7351. doi: 10.1074/jbc.M807398200.
21. Connaris H, Govorkova E A, Ligertwood Y, Dutia B M, Yang L, Tauber S, Taylor M A, Alias N, Hagan R, Nash A A, Webster R G, Taylor G L. 2014. Prevention of influenza by targeting host receptors using engineered proteins. Proc. Natl. Acad. Sci. U.S.A. 111(17):6401-6406. doi: 10.1073/pnas.1404205111.
22. Ilyushina N A, Bovin N V, Webster R G, Govorkova E A. 2006. Combination chemotherapy, a potential strategy for reducing the emergence of drug-resistant influenza A variants. Antiviral. Res.70:121-131.
23. Baranovich T, Burnham A J, Marathe B M, Armstrong J, Guan Y, Shu Y, Peiris J M, Webby R J, Webster R G, Govorkova E A. 2014. The neuraminidase inhibitor oseltamivir is effective against A/Anhui/1/2013 (H7N9) influenza virus in a mouse model of acute respiratory distress syndrome. J. Infect. Dis. 209:1343-1353. doi: 10.1093/infdis/jit554.
24. Webster R G and Govorkova E A. 2014. Continuing challenges in influenza. Ann. N.Y. Acad. Sci. 1323(1): 115-139. doi: 10.1111/nyas.12462.
25. Marjuki H, Mishin V P, Chesnokov A P, De La Cruz J A, Fry A M, Villanueva J, Gubareva L V. 2014. An investigational antiviral drug, DAS181, effectively inhibits replication of zoonotic influenza A virus subtype H7N9 and protects mice from lethality. J. Infect. Dis. 210:435-440. doi: 10.1093/infdis/jiu105.
26. Guan Y, Shortridge K F, Krauss S, Webster R G. 1999. Molecular characterization of H9N2 influenza viruses: were they the donors of the "internal" genes of H5N1 viruses in Hong Kong? Proc. Natl. Acad. Sci. U.S.A. 96:9363-9367.

The invention claimed is:

1. A method of modulating or priming an immune response in a subject, the method comprising administering an immunomodulatory amount or quantity of Sp2CBMTD to a healthy subject in need thereof in more than one dose prior to an infection or a likely infection caused or contributed to by a pathogen.

2. The method of claim 1, wherein the Sp2CBMTD is administered at a dose of about 0.1, 1, 10, or 100 µg of the Sp2CBMTD/subject/day.

* * * * *

UNITED STATES PATENT AND TRADEMARK OFFICE
CERTIFICATE OF CORRECTION

PATENT NO. : 10,363,298 B2
APPLICATION NO. : 15/113672
DATED : July 30, 2019
INVENTOR(S) : Taylor et al.

It is certified that error appears in the above-identified patent and that said Letters Patent is hereby corrected as shown below:

In the Specification

Column 9, Line 11: Please correct "PA0579" to read -- PAO579 --

Column 17, Line 26: Please correct "IL-1R (B),11-6" to read -- IL-1β (B), II-6 --

Column 17, Line 31: Please correct "μg/mL" to read -- pg/mL --

Column 23, Line 49: Please correct "IL-1 p" to read -- IL-1β --

Column 37, Table 4a, Line 50: Please correct "31" to read -- 32 --

Column 41, Line 12: Please correct "μg/mL" to read -- pg/mL --

Signed and Sealed this
Twelfth Day of November, 2019

Andrei Iancu
*Director of the United States Patent and Trademark Office*

SEQUENCE LISTING

```
<160> NUMBER OF SEQ ID NOS: 28

<210> SEQ ID NO 1
<211> LENGTH: 781
<212> TYPE: PRT
<213> ORGANISM: Vibrio cholerae

<400> SEQUENCE: 1

Met Arg Phe Lys Asn Val Lys Lys Thr Ala Leu Met Leu Ala Met Phe
1               5                   10                  15

Gly Met Ala Thr Ser Ser Asn Ala Ala Leu Phe Asp Tyr Asn Ala Thr
            20                  25                  30

Gly Asp Thr Glu Phe Asp Ser Pro Ala Lys Gln Gly Trp Met Gln Asp
        35                  40                  45

Asn Thr Asn Asn Gly Ser Gly Val Leu Thr Asn Ala Asp Gly Met Pro
    50                  55                  60

Ala Trp Leu Val Gln Gly Ile Gly Gly Arg Ala Gln Trp Thr Tyr Ser
65                  70                  75                  80

Leu Ser Thr Asn Gln His Ala Gln Ala Ser Ser Phe Gly Trp Arg Met
```

```
                    85                  90                  95
Thr Thr Glu Met Lys Val Leu Ser Gly Gly Met Ile Thr Asn Tyr Tyr
                100                 105                 110

Ala Asn Gly Thr Gln Arg Val Leu Pro Ile Ile Ser Leu Asp Ser Ser
            115                 120                 125

Gly Asn Leu Val Val Glu Phe Glu Gly Gln Thr Gly Arg Thr Val Leu
        130                 135                 140

Ala Thr Gly Thr Ala Thr Glu Tyr His Lys Phe Glu Leu Val Phe
145                 150                 155                 160

Leu Pro Gly Ser Asn Pro Ser Ala Ser Phe Tyr Phe Asp Gly Lys Leu
                165                 170                 175

Ile Arg Asp Asn Ile Gln Pro Thr Ala Ser Lys Gln Asn Met Ile Val
                180                 185                 190

Trp Gly Asn Gly Ser Ser Asn Thr Asp Gly Val Ala Ala Tyr Arg Asp
                195                 200                 205

Ile Lys Phe Glu Ile Gln Gly Asp Val Ile Phe Arg Gly Pro Asp Arg
                210                 215                 220

Ile Pro Ser Ile Val Ala Ser Ser Val Thr Pro Gly Val Val Thr Ala
225                 230                 235                 240

Phe Ala Glu Lys Arg Val Gly Gly Gly Asp Pro Gly Ala Leu Ser Asn
                245                 250                 255

Thr Asn Asp Ile Ile Thr Arg Thr Ser Arg Asp Gly Gly Ile Thr Trp
                260                 265                 270

Asp Thr Glu Leu Asn Leu Thr Glu Gln Ile Asn Val Ser Asp Glu Phe
                275                 280                 285

Asp Phe Ser Asp Pro Arg Pro Ile Tyr Asp Pro Ser Ser Asn Thr Val
            290                 295                 300

Leu Val Ser Tyr Ala Arg Trp Pro Thr Asp Ala Ala Gln Asn Gly Asp
305                 310                 315                 320

Arg Ile Lys Pro Trp Met Pro Asn Gly Ile Phe Tyr Ser Val Tyr Asp
                325                 330                 335

Val Ala Ser Gly Asn Trp Gln Ala Pro Ile Asp Val Thr Asp Gln Val
                340                 345                 350

Lys Glu Arg Ser Phe Gln Ile Ala Gly Trp Gly Gly Ser Glu Leu Tyr
                355                 360                 365

Arg Arg Asn Thr Ser Leu Asn Ser Gln Gln Asp Trp Gln Ser Asn Ala
                370                 375                 380

Lys Ile Arg Ile Val Asp Gly Ala Ala Asn Gln Ile Gln Val Ala Asp
385                 390                 395                 400

Gly Ser Arg Lys Tyr Val Val Thr Leu Ser Ile Asp Glu Ser Gly Gly
                405                 410                 415

Leu Val Ala Asn Leu Asn Gly Val Ser Ala Pro Ile Ile Leu Gln Ser
                420                 425                 430

Glu His Ala Lys Val His Ser Phe His Asp Tyr Glu Leu Gln Tyr Ser
                435                 440                 445

Ala Leu Asn His Thr Thr Thr Leu Phe Val Asp Gly Gln Gln Ile Thr
            450                 455                 460

Thr Trp Ala Gly Glu Val Ser Gln Glu Asn Asn Ile Gln Phe Gly Asn
465                 470                 475                 480

Ala Asp Ala Gln Ile Asp Gly Arg Leu His Val Gln Lys Ile Val Leu
                485                 490                 495

Thr Gln Gln Gly His Asn Leu Val Glu Phe Asp Ala Phe Tyr Leu Ala
            500                 505                 510
```

```
Gln Gln Thr Pro Glu Val Glu Lys Asp Leu Glu Lys Leu Gly Trp Thr
            515                 520                 525

Lys Ile Lys Thr Gly Asn Thr Met Ser Leu Tyr Gly Asn Ala Ser Val
        530                 535                 540

Asn Pro Gly Pro Gly His Gly Ile Thr Leu Thr Arg Gln Gln Asn Ile
545                 550                 555                 560

Ser Gly Ser Gln Asn Gly Arg Leu Ile Tyr Pro Ala Ile Val Leu Asp
            565                 570                 575

Arg Phe Phe Leu Asn Val Met Ser Ile Tyr Ser Asp Asp Gly Gly Ser
            580                 585                 590

Asn Trp Gln Thr Gly Ser Thr Leu Pro Ile Pro Phe Arg Trp Lys Ser
            595                 600                 605

Ser Ser Ile Leu Glu Thr Leu Glu Pro Ser Glu Ala Asp Met Val Glu
            610                 615                 620

Leu Gln Asn Gly Asp Leu Leu Leu Thr Ala Arg Leu Asp Phe Asn Gln
625                 630                 635                 640

Ile Val Asn Gly Val Asn Tyr Ser Pro Arg Gln Gln Phe Leu Ser Lys
            645                 650                 655

Asp Gly Gly Ile Thr Trp Ser Leu Leu Glu Ala Asn Asn Ala Asn Val
            660                 665                 670

Phe Ser Asn Ile Ser Thr Gly Thr Val Asp Ala Ser Ile Thr Arg Phe
            675                 680                 685

Glu Gln Ser Asp Gly Ser His Phe Leu Leu Phe Thr Asn Pro Gln Gly
            690                 695                 700

Asn Pro Ala Gly Thr Asn Gly Arg Gln Asn Leu Gly Leu Trp Phe Ser
705                 710                 715                 720

Phe Asp Glu Gly Val Thr Trp Lys Gly Pro Ile Gln Leu Val Asn Gly
            725                 730                 735

Ala Ser Ala Tyr Ser Asp Ile Tyr Gln Leu Asp Ser Glu Asn Ala Ile
            740                 745                 750

Val Ile Val Glu Thr Asp Asn Ser Asn Met Arg Ile Leu Arg Met Pro
            755                 760                 765

Ile Thr Leu Leu Lys Gln Lys Leu Thr Leu Ser Gln Asn
            770                 775                 780

<210> SEQ ID NO 2
<211> LENGTH: 192
<212> TYPE: PRT
<213> ORGANISM: Vibrio cholerae

<400> SEQUENCE: 2

Ala Leu Phe Asp Tyr Asn Ala Thr Gly Asp Thr Glu Phe Asp Ser Pro
1               5                   10                  15

Ala Lys Gln Gly Trp Met Gln Asp Asn Thr Asn Gly Ser Gly Val
            20                  25                  30

Leu Thr Asn Ala Asp Gly Met Pro Ala Trp Leu Val Gln Gly Ile Gly
            35                  40                  45

Gly Arg Ala Gln Trp Thr Tyr Ser Leu Ser Thr Asn Gln His Ala Gln
        50                  55                  60

Ala Ser Ser Phe Gly Trp Arg Met Thr Thr Glu Met Lys Val Leu Ser
65                  70                  75                  80

Gly Gly Met Ile Thr Asn Tyr Tyr Ala Asn Gly Thr Gln Arg Val Leu
            85                  90                  95

Pro Ile Ile Ser Leu Asp Ser Ser Gly Asn Leu Val Val Glu Phe Glu
```

```
                    100                 105                 110
Gly Gln Thr Gly Arg Thr Val Leu Ala Thr Gly Thr Ala Ala Thr Glu
            115                 120                 125

Tyr His Lys Phe Glu Leu Val Phe Leu Pro Gly Ser Asn Pro Ser Ala
130                 135                 140

Ser Phe Tyr Phe Asp Gly Lys Leu Ile Arg Asp Asn Ile Gln Pro Thr
145                 150                 155                 160

Ala Ser Lys Gln Asn Met Ile Val Trp Gly Asn Gly Ser Ser Asn Thr
                165                 170                 175

Asp Gly Val Ala Ala Tyr Arg Asp Ile Lys Phe Glu Ile Gln Gly Asp
            180                 185                 190

<210> SEQ ID NO 3
<211> LENGTH: 1035
<212> TYPE: PRT
<213> ORGANISM: Streptococcus pneumoniae

<400> SEQUENCE: 3

Met Ser Tyr Phe Arg Asn Arg Asp Ile Asp Ile Glu Arg Asn Ser Met
1               5                   10                  15

Asn Arg Ser Val Gln Glu Arg Lys Cys Arg Tyr Ser Ile Arg Lys Leu
            20                  25                  30

Ser Val Gly Ala Val Ser Met Ile Val Gly Ala Val Val Phe Gly Thr
        35                  40                  45

Ser Pro Val Leu Ala Gln Glu Gly Ala Ser Glu Gln Pro Leu Ala Asn
    50                  55                  60

Glu Thr Gln Leu Ser Gly Glu Ser Ser Thr Leu Thr Asp Thr Glu Lys
65                  70                  75                  80

Ser Gln Pro Ser Ser Glu Thr Glu Leu Ser Gly Asn Lys Gln Glu Gln
                85                  90                  95

Glu Arg Lys Asp Lys Gln Glu Glu Lys Ile Pro Arg Asp Tyr Tyr Ala
            100                 105                 110

Arg Asp Leu Glu Asn Val Glu Thr Val Ile Glu Lys Glu Asp Val Glu
        115                 120                 125

Thr Asn Ala Ser Asn Gly Gln Arg Val Asp Leu Ser Ser Glu Leu Asp
    130                 135                 140

Lys Leu Lys Lys Leu Glu Asn Ala Thr Val His Met Glu Phe Lys Pro
145                 150                 155                 160

Asp Ala Lys Ala Pro Ala Phe Tyr Asn Leu Phe Ser Val Ser Ser Ala
                165                 170                 175

Thr Lys Lys Asp Glu Tyr Phe Thr Met Ala Val Tyr Asn Asn Thr Ala
            180                 185                 190

Thr Leu Glu Gly Arg Gly Ser Asp Gly Lys Gln Phe Tyr Asn Asn Tyr
        195                 200                 205

Asn Asp Ala Pro Leu Lys Val Lys Pro Gly Gln Trp Asn Ser Val Thr
    210                 215                 220

Phe Thr Val Glu Lys Pro Thr Ala Glu Leu Pro Lys Gly Arg Val Arg
225                 230                 235                 240

Leu Tyr Val Asn Gly Val Leu Ser Arg Thr Ser Leu Arg Ser Gly Asn
                245                 250                 255

Phe Ile Lys Asp Met Pro Asp Val Thr His Val Gln Ile Gly Ala Thr
            260                 265                 270

Lys Arg Ala Asn Asn Thr Val Trp Gly Ser Asn Leu Gln Ile Arg Asn
        275                 280                 285
```

-continued

```
Leu Thr Val Tyr Asn Arg Ala Leu Thr Pro Glu Glu Val Gln Lys Arg
    290                 295                 300

Ser Gln Leu Phe Lys Arg Ser Asp Leu Glu Lys Lys Leu Pro Glu Gly
305                 310                 315                 320

Ala Ala Leu Thr Glu Lys Thr Asp Ile Phe Glu Ser Gly Arg Asn Gly
                325                 330                 335

Lys Pro Asn Lys Asp Gly Ile Lys Ser Tyr Arg Ile Pro Ala Leu Leu
                340                 345                 350

Lys Thr Asp Lys Gly Thr Leu Ile Ala Gly Ala Asp Glu Arg Arg Leu
                355                 360                 365

His Ser Ser Asp Trp Gly Asp Ile Gly Met Val Ile Arg Arg Ser Glu
370                 375                 380

Asp Asn Gly Lys Thr Trp Gly Asp Arg Val Thr Ile Thr Asn Leu Arg
385                 390                 395                 400

Asp Asn Pro Lys Ala Ser Asp Pro Ser Ile Gly Ser Pro Val Asn Ile
                405                 410                 415

Asp Met Val Leu Val Gln Asp Pro Glu Thr Lys Arg Ile Phe Ser Ile
                420                 425                 430

Tyr Asp Met Phe Pro Glu Gly Lys Gly Ile Phe Gly Met Ser Ser Gln
            435                 440                 445

Lys Glu Glu Ala Tyr Lys Lys Ile Asp Gly Lys Thr Tyr Gln Ile Leu
450                 455                 460

Tyr Arg Glu Gly Glu Lys Gly Ala Tyr Thr Ile Arg Glu Asn Gly Thr
465                 470                 475                 480

Val Tyr Thr Pro Asp Gly Lys Ala Thr Asp Tyr Arg Val Val Val Asp
                485                 490                 495

Pro Val Lys Pro Ala Tyr Ser Asp Lys Gly Asp Leu Tyr Lys Gly Asn
                500                 505                 510

Gln Leu Leu Gly Asn Ile Tyr Phe Thr Thr Asn Lys Thr Ser Pro Phe
            515                 520                 525

Arg Ile Ala Lys Asp Ser Tyr Leu Trp Met Ser Tyr Ser Asp Asp Asp
530                 535                 540

Gly Lys Thr Trp Ser Ala Pro Gln Asp Ile Thr Pro Met Val Lys Ala
545                 550                 555                 560

Asp Trp Met Lys Phe Leu Gly Val Gly Pro Gly Thr Gly Ile Val Leu
                565                 570                 575

Arg Asn Gly Pro His Lys Gly Arg Ile Leu Ile Pro Val Tyr Thr Thr
                580                 585                 590

Asn Asn Val Ser His Leu Asn Gly Ser Gln Ser Ser Arg Ile Ile Tyr
            595                 600                 605

Ser Asp Asp His Gly Lys Thr Trp His Ala Gly Glu Ala Val Asn Asp
610                 615                 620

Asn Arg Gln Val Asp Gly Gln Lys Ile His Ser Ser Thr Met Asn Asn
625                 630                 635                 640

Arg Arg Ala Gln Asn Thr Glu Ser Thr Val Val Gln Leu Asn Asn Gly
                645                 650                 655

Asp Val Lys Leu Phe Met Arg Gly Leu Thr Gly Asp Leu Gln Val Ala
                660                 665                 670

Thr Ser Lys Asp Gly Gly Val Thr Trp Glu Lys Asp Ile Lys Arg Tyr
            675                 680                 685

Pro Gln Val Lys Asp Val Tyr Val Gln Met Ser Ala Ile His Thr Met
690                 695                 700

His Glu Gly Lys Glu Tyr Ile Ile Leu Ser Asn Ala Gly Gly Pro Lys
```

```
            705                 710                 715                 720
        Arg Glu Asn Gly Met Val His Leu Ala Arg Val Glu Glu Asn Gly Glu
                        725                 730                 735

Leu Thr Trp Leu Lys His Asn Pro Ile Gln Lys Gly Glu Phe Ala Tyr
                    740                 745                 750

Asn Ser Leu Gln Glu Leu Gly Asn Gly Glu Tyr Gly Ile Leu Tyr Glu
                    755                 760                 765

His Thr Glu Lys Gly Gln Asn Ala Tyr Thr Leu Ser Phe Arg Lys Phe
                770                 775                 780

Asn Trp Asp Phe Leu Ser Lys Asp Leu Ile Ser Pro Thr Glu Ala Lys
        785                 790                 795                 800

Val Lys Arg Thr Arg Glu Met Gly Lys Gly Val Ile Gly Leu Glu Phe
                        805                 810                 815

Asp Ser Glu Val Leu Val Asn Lys Ala Pro Thr Leu Gln Leu Ala Asn
                    820                 825                 830

Gly Lys Thr Ala Arg Phe Met Thr Gln Tyr Asp Thr Lys Thr Leu Leu
                835                 840                 845

Phe Thr Val Asp Ser Glu Asp Met Gly Gln Lys Val Thr Gly Leu Ala
            850                 855                 860

Glu Gly Ala Ile Glu Ser Met His Asn Leu Pro Val Ser Val Ala Gly
        865                 870                 875                 880

Thr Lys Leu Ser Asn Gly Met Asn Gly Ser Glu Ala Ala Val His Glu
                        885                 890                 895

Val Pro Glu Tyr Thr Gly Pro Leu Gly Thr Ser Gly Glu Glu Pro Ala
                    900                 905                 910

Pro Thr Val Glu Lys Pro Glu Tyr Thr Gly Pro Leu Gly Thr Ser Gly
                    915                 920                 925

Glu Glu Pro Ala Pro Thr Val Glu Lys Pro Glu Tyr Thr Gly Pro Leu
                930                 935                 940

Gly Thr Ala Gly Glu Glu Ala Ala Pro Thr Val Glu Lys Pro Glu Phe
        945                 950                 955                 960

Thr Gly Gly Val Asn Gly Thr Glu Pro Ala Val His Glu Ile Ala Glu
                        965                 970                 975

Tyr Lys Gly Ser Asp Ser Leu Val Thr Leu Thr Thr Lys Glu Asp Tyr
                    980                 985                 990

Thr Tyr Lys Ala Pro Leu Ala Gln Gln Ala Leu Pro Glu Thr Gly Asn
                    995                 1000                1005

Lys Glu  Ser Asp Leu Leu Ala  Ser Leu Gly Leu Thr  Ala Phe Phe
                1010                1015                1020

Leu Gly  Leu Phe Thr Leu Gly  Lys Lys Arg Glu Gln
                1025                1030                1035

<210> SEQ ID NO 4
<211> LENGTH: 185
<212> TYPE: PRT
<213> ORGANISM: Streptococcus pneumoniae

<400> SEQUENCE: 4

Val Ile Glu Lys Glu Asp Val Glu Thr Asn Ala Ser Asn Gly Gln Arg
1               5                   10                  15

Val Asp Leu Ser Ser Glu Leu Asp Lys Leu Lys Lys Leu Glu Asn Ala
                20                  25                  30

Thr Val His Met Glu Phe Lys Pro Asp Ala Lys Ala Pro Ala Phe Tyr
            35                  40                  45
```

```
Asn Leu Phe Ser Val Ser Ser Ala Thr Lys Lys Asp Glu Tyr Phe Thr
 50                  55                  60

Met Ala Val Tyr Asn Asn Thr Ala Thr Leu Glu Gly Arg Gly Ser Asp
 65                  70                  75                  80

Gly Lys Gln Phe Tyr Asn Asn Tyr Asn Asp Ala Pro Leu Lys Val Lys
                 85                  90                  95

Pro Gly Gln Trp Asn Ser Val Thr Phe Thr Val Glu Lys Pro Thr Ala
            100                 105                 110

Glu Leu Pro Lys Gly Arg Val Arg Leu Tyr Val Asn Gly Val Leu Ser
        115                 120                 125

Arg Thr Ser Leu Arg Ser Gly Asn Phe Ile Lys Asp Met Pro Asp Val
130                 135                 140

Thr His Val Gln Ile Gly Ala Thr Lys Arg Ala Asn Asn Thr Val Trp
145                 150                 155                 160

Gly Ser Asn Leu Gln Ile Arg Asn Leu Thr Val Tyr Asn Arg Ala Leu
                165                 170                 175

Thr Pro Glu Glu Val Gln Lys Arg Ser
            180                 185

<210> SEQ ID NO 5
<211> LENGTH: 438
<212> TYPE: PRT
<213> ORGANISM: Pseudomonas aeruginosa

<400> SEQUENCE: 5

Met Asn Thr Tyr Phe Asp Ile Pro His Arg Leu Val Gly Lys Ala Leu
 1               5                  10                  15

Tyr Glu Ser Tyr Tyr Asp His Phe Gly Gln Met Asp Ile Leu Ser Asp
                20                  25                  30

Gly Ser Leu Tyr Leu Ile Tyr Arg Arg Ala Thr Glu His Val Gly Gly
            35                  40                  45

Ser Asp Gly Arg Val Val Phe Ser Lys Leu Glu Gly Gly Ile Trp Ser
 50                  55                  60

Ala Pro Thr Ile Val Ala Gln Ala Gly Gln Asp Phe Arg Asp Val
 65                  70                  75                  80

Ala Gly Gly Thr Met Pro Ser Gly Arg Ile Val Ala Ala Ser Thr Val
                85                  90                  95

Tyr Glu Thr Gly Glu Val Lys Val Tyr Val Ser Asp Asp Ser Gly Val
            100                 105                 110

Thr Trp Val His Lys Phe Thr Leu Ala Arg Gly Gly Ala Asp Tyr Asn
        115                 120                 125

Phe Ala His Gly Lys Ser Phe Gln Val Gly Ala Arg Tyr Val Ile Pro
130                 135                 140

Leu Tyr Ala Ala Thr Gly Val Asn Tyr Glu Leu Lys Trp Leu Glu Ser
145                 150                 155                 160

Ser Asp Gly Gly Glu Thr Trp Gly Glu Gly Ser Thr Ile Tyr Ser Gly
                165                 170                 175

Asn Thr Pro Tyr Asn Glu Thr Ser Tyr Leu Pro Val Gly Asp Gly Val
            180                 185                 190

Ile Leu Ala Val Ala Arg Val Gly Ser Ala Gly Gly Ala Leu Arg
        195                 200                 205

Gln Phe Ile Ser Leu Asp Asp Gly Gly Thr Trp Thr Asp Gln Gly Asn
210                 215                 220

Val Thr Ala Gln Asn Gly Asp Ser Thr Asp Ile Leu Val Ala Pro Ser
225                 230                 235                 240
```

Leu Ser Tyr Ile Tyr Ser Glu Gly Gly Thr Pro His Val Val Leu Leu
                245                 250                 255

Tyr Thr Asn Arg Thr Thr His Phe Cys Tyr Tyr Arg Thr Ile Leu Leu
            260                 265                 270

Ala Lys Ala Val Ala Gly Ser Ser Gly Trp Thr Glu Arg Val Pro Val
        275                 280                 285

Tyr Ser Ala Pro Ala Ala Ser Gly Tyr Thr Ser Gln Val Val Leu Gly
    290                 295                 300

Gly Arg Arg Ile Leu Gly Asn Leu Phe Arg Glu Thr Ser Ser Thr Thr
305                 310                 315                 320

Ser Gly Ala Tyr Gln Phe Glu Val Tyr Leu Gly Val Pro Asp Phe
                325                 330                 335

Glu Ser Asp Trp Phe Ser Val Ser Ser Asn Ser Leu Tyr Thr Leu Ser
            340                 345                 350

His Gly Leu Gln Arg Ser Pro Arg Arg Val Val Glu Phe Ala Arg
        355                 360                 365

Ser Ser Ser Pro Ser Thr Trp Asn Ile Val Met Pro Ser Tyr Phe Asn
370                 375                 380

Asp Gly Gly His Lys Gly Ser Gly Ala Gln Val Glu Val Gly Ser Leu
385                 390                 395                 400

Asn Ile Arg Leu Gly Thr Gly Ala Ala Val Trp Gly Thr Gly Tyr Phe
                405                 410                 415

Gly Gly Ile Asp Asn Ser Ala Thr Thr Arg Phe Ala Thr Gly Tyr Tyr
            420                 425                 430

Arg Val Arg Ala Trp Ile
        435

<210> SEQ ID NO 6
<211> LENGTH: 106
<212> TYPE: PRT
<213> ORGANISM: Pseudomonas aeruginosa

<400> SEQUENCE: 6

Val Pro Asp Phe Glu Ser Asp Trp Phe Ser Val Ser Ser Asn Ser Leu
1               5                   10                  15

Tyr Thr Leu Ser His Gly Leu Gln Arg Ser Pro Arg Arg Val Val Val
            20                  25                  30

Glu Phe Ala Arg Ser Ser Ser Pro Ser Thr Trp Asn Ile Val Met Pro
        35                  40                  45

Ser Tyr Phe Asn Asp Gly Gly His Lys Gly Ser Gly Ala Gln Val Glu
    50                  55                  60

Val Gly Ser Leu Asn Ile Arg Leu Gly Thr Gly Ala Ala Val Trp Gly
65                  70                  75                  80

Thr Gly Tyr Phe Gly Gly Ile Asp Asn Ser Ala Thr Thr Arg Phe Ala
                85                  90                  95

Thr Gly Tyr Tyr Arg Val Arg Ala Trp Ile
            100                 105

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
ggctccatgg cactttttga ctataacgc                                    29

<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
gcacggatcc accaccgtcg ccttgaattt c                                 31

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
ggctggatcc ggtatggtcc cggattttga gtca                              34

<210> SEQ ID NO 10
<211> LENGTH: 31
<212> TYPE: DNA
<213> ORGANISM: Artificial Sequence
<220> FEATURE:
<223> OTHER INFORMATION: Primer

<400> SEQUENCE: 10
ccgactcgag ctaaatccat gctctgaccc g                                 31

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
ggctccatgg cactttttga ctataacgc                                    29

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12
gcacggatcc accaccgtcg ccttgaattt c                                 31

<210> SEQ ID NO 13
<211> LENGTH: 31
<212> TYPE: DNA
<213> ORGANISM: Artificial Sequence
<220> FEATURE:
<223> OTHER INFORMATION: Primer

<400> SEQUENCE: 13
ggctggatcc ggtgcacttt ttgactataa c                                 31

<210> SEQ ID NO 14
<211> LENGTH: 31
<212> TYPE: DNA
<213> ORGANISM: Artificial Sequence

```
<220> FEATURE:
<223> OTHER INFORMATION: Primer

<400> SEQUENCE: 14
gtcccaaagc ttgaccgtcg ccttgaattt c                              31

<210> SEQ ID NO 15
<211> LENGTH: 34
<212> TYPE: DNA
<213> ORGANISM: Artificial Sequence
<220> FEATURE:
<223> OTHER INFORMATION: Primer

<400> SEQUENCE: 15
ctgcaagctt tgggagtccc ggattttgag tcag                           34

<210> SEQ ID NO 16
<211> LENGTH: 31
<212> TYPE: DNA
<213> ORGANISM: Artificial Sequence
<220> FEATURE:
<223> OTHER INFORMATION: Primer

<400> SEQUENCE: 16
ccgactcgag ctaaatccat gctctgaccc g                              31

<210> SEQ ID NO 17
<211> LENGTH: 28
<212> TYPE: DNA
<213> ORGANISM: Artificial Sequence
<220> FEATURE:
<223> OTHER INFORMATION: Primer

<400> SEQUENCE: 17
ggctccatgg tgatagaaaa agaagatg                                  28

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18
accggatcca ccaccactac gttttgtac ctc                             33

<210> SEQ ID NO 19
<211> LENGTH: 34
<212> TYPE: DNA
<213> ORGANISM: Artificial Sequence
<220> FEATURE:
<223> OTHER INFORMATION: Primer

<400> SEQUENCE: 19
ggctggatcc ggtatggtcc cggattttga gtca                           34

<210> SEQ ID NO 20
<211> LENGTH: 31
<212> TYPE: DNA
<213> ORGANISM: Artificial Sequence
<220> FEATURE:
<223> OTHER INFORMATION: Primer

<400> SEQUENCE: 20
ccgactcgag ctaaatccat gctctgaccc g                              31
```

<210> SEQ ID NO 21
<211> LENGTH: 28
<212> TYPE: DNA
<213> ORGANISM: Artificial Sequence
<220> FEATURE:
<223> OTHER INFORMATION: Primer

<400> SEQUENCE: 21
ggctccatgg tgatagaaaa agaagatg                                    28

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22
accggatcca ccaccactac gttttttgtac ctc                              33

<210> SEQ ID NO 23
<211> LENGTH: 32
<212> TYPE: DNA
<213> ORGANISM: Artificial Sequence
<220> FEATURE:
<223> OTHER INFORMATION: Primer

<400> SEQUENCE: 23
ggctggatcc ggtgtgatag aaaaagaaga tg                                32

<210> SEQ ID NO 24
<211> LENGTH: 33
<212> TYPE: DNA
<213> ORGANISM: Artificial Sequence
<220> FEATURE:
<223> OTHER INFORMATION: Primer

<400> SEQUENCE: 24
tcccaaagct tgaccactac gttttttgtgc ctc                              33

<210> SEQ ID NO 25
<211> LENGTH: 34
<212> TYPE: DNA
<213> ORGANISM: Artificial Sequence
<220> FEATURE:
<223> OTHER INFORMATION: Primer

<400> SEQUENCE: 25
ctgcaagctt tgggagtccc ggattttgag tcag                              34

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
ccgactcgag ctaaatccat gctctgaccc g                                 31

<210> SEQ ID NO 27
<211> LENGTH: 5
<212> TYPE: PRT
<213> ORGANISM: Artificial Sequence
<220> FEATURE:
<223> OTHER INFORMATION: Peptide Linker

```
<400> SEQUENCE: 27

Gly Gly Gly Ser Gly
1               5

<210> SEQ ID NO 28
<211> LENGTH: 5
<212> TYPE: PRT
<213> ORGANISM: Artificial Sequence
<220> FEATURE:
<223> OTHER INFORMATION: Peptide Linker

<400> SEQUENCE: 28

Gly Gln Ala Leu Gly
1               5
```